United States Patent

Hemming et al.

[11] Patent Number: 6,134,473
[45] Date of Patent: Oct. 17, 2000

[54] MICROPROCESSOR CAPTURE DETECTION CIRCUIT AND METHOD

[75] Inventors: Michael Todd Hemming, Champlin; Bradley C. Peck, Coon Rapids; Brian A. Blow, Maple Grove; Scott M. Morrison, Lino Lakes; Robert John Schuelke, Lakeville, all of Minn.

[73] Assignee: Medtronic, Inc., Minneapolis, Minn.

[21] Appl. No.: 09/291,514

[22] Filed: Apr. 14, 1999

Related U.S. Application Data

[62] Division of application No. 08/841,064, Apr. 29, 1997, Pat. No. 5,873,898.

[51] Int. Cl.[7] .................................................... A61N 1/37
[52] U.S. Cl. .............................................. 607/28
[58] Field of Search ......................... 607/27, 28

[56] References Cited

U.S. PATENT DOCUMENTS

| | | |
|---|---|---|
| 3,920,024 | 11/1975 | Bowers . |
| 4,055,189 | 10/1977 | Auerbach et al. . |
| 4,088,139 | 5/1978 | Auerbach . |
| 4,114,627 | 9/1978 | Lewyn et al. . |
| 4,144,892 | 3/1979 | Auerbach . |
| 4,228,803 | 10/1980 | Rickards . |
| 4,305,396 | 12/1981 | Wittkampf et al. . |
| 4,343,312 | 8/1982 | Cals et al. . |
| 4,373,531 | 2/1983 | Wittkampf et al. . |
| 4,407,287 | 10/1983 | Herpers . |
| 4,537,201 | 8/1985 | Delle-Vedove et al. . |
| 4,543,956 | 10/1985 | Herscovici . |
| 4,543,963 | 10/1985 | Gessman ................................. 607/27 |
| 4,649,931 | 3/1987 | Beck . |
| 4,665,919 | 5/1987 | Mensink et al. . |
| 4,674,508 | 6/1987 | DeCote . |
| 4,674,509 | 6/1987 | DeCote, Jr. . |
| 4,686,988 | 8/1987 | Sholder . |
| 4,708,142 | 11/1987 | DeCote, Jr. . |
| 4,729,376 | 3/1988 | DeCote, Jr. . |
| 4,759,366 | 7/1988 | Callaghan . |
| 4,759,367 | 7/1988 | Callaghan . |
| 4,766,900 | 8/1988 | Callaghan . |
| 4,766,901 | 8/1988 | Callaghan . |
| 4,811,738 | 3/1989 | Economides et al. . |
| 4,815,475 | 3/1989 | Burger . |

(List continued on next page.)

FOREIGN PATENT DOCUMENTS 0716 864 A2  11/1995  European Pat. Off. .

OTHER PUBLICATIONS

*Thera SR Product Information Manual, Pacemark Models 8940, 8941, 8942*, Medtronic, Inc. 1994.
*Thera D Product Information Manual, Pacemaker Models, 7944, 7945, 7946*, Medtronic, Inc. 1994.

*Primary Examiner*—William E. Kamm
*Attorney, Agent, or Firm*—Girma Wolde-Michael; Harold R. Patton

[57] ABSTRACT

A software programmable microprocessor discriminates between evoked response signals and post-pace polarization signals sensed by an implantable medical device. The polarity of the positive or negative change in voltage in respect of time (or dv/dt) of the waveform incident on the lead electrodes is monitored during a short period of time immediately following a paced event. It has been discovered that the post-pace polarization signal exhibits a relatively constant polarity during the capture detect window, and that the evoked response signal may cause the polarity of post-pace polarization signal to reverse during the capture detect window. The sign of the post-pace polarization polarity, either positive or negative, is determined by the design of the specific output circuitry. The evoked response signal may reverse the polarity of the sensed signal in either case, from positive to negative or from negative to positive, during the time window of interest. In another embodiment, when the magnitude of the post-pace polarization is so great that the evoked response does not reverse the polarity of the waveform, discrimination of the evoked response is achieved by noting an acceleration (or increasing magnitude of dv/dt) in the sensed signal or waveform.

5 Claims, 38 Drawing Sheets

U.S. PATENT DOCUMENTS

| | | |
|---|---|---|
| 4,858,610 | 8/1989 | Callaghan et al. . |
| 4,878,497 | 11/1989 | Callaghan et al. . |
| 4,895,152 | 1/1990 | Callaghan et al. . |
| 4,903,700 | 2/1990 | Whigham et al. . |
| 4,964,411 | 10/1990 | Johnson et al. . |
| 4,969,467 | 11/1990 | Callaghan et al. . |
| 4,979,507 | 12/1990 | Heinz et al. . |
| 4,996,986 | 3/1991 | Thomassen . |
| 5,018,523 | 5/1991 | Bach, Jr. et al. . |
| 5,086,774 | 2/1992 | Duncan . |
| 5,105,810 | 4/1992 | Collins et al. . |
| 5,127,401 | 7/1992 | Grevious et al. . |
| 5,143,081 | 9/1992 | Young et al. . |
| 5,161,529 | 11/1992 | Stotts et al. . |
| 5,184,615 | 2/1993 | Nappholz et al. . |
| 5,222,493 | 6/1993 | Sholder . |
| 5,233,985 | 8/1993 | Hudrlik . |
| 5,265,601 | 11/1993 | Mehra . |
| 5,265,603 | 11/1993 | Hudrlik . |
| 5,271,393 | 12/1993 | Callaghan . |
| 5,312,446 | 5/1994 | Holschbach et al. . |
| 5,330,512 | 7/1994 | Hauck et al. . |
| 5,350,410 | 9/1994 | Kleks et al. . |
| 5,391,192 | 2/1995 | Lu et al. . |
| 5,405,365 | 4/1995 | Hoegnelid et al. ............. 607/28 |
| 5,417,718 | 5/1995 | Kleks et al. . |
| 5,431,693 | 7/1995 | Schroeppel . |
| 5,443,485 | 8/1995 | Housworth et al. . |
| 5,476,485 | 12/1995 | Weinberg et al. . |
| 5,476,487 | 12/1995 | Sholder . |
| 5,522,855 | 6/1996 | Hoegnelid . |
| 5,571,144 | 11/1996 | Schroeppel . |
| 5,584,299 | 12/1996 | Saka et al. . |

SMOOTHED DERIVATIVE DETECTION OF CAPTURE

MICROPROCESSOR CAPTURE DETECTION CIRCUIT AND METHOD

CROSS-REFERENCE TO RELATED APPLICATION

This application is a divisional application of U.S. patent application Ser. No. 08/841,064, filed Apr. 29, 1997 now U.S. Pat. No. 5,873,898 entitled "Microprocessor Capture Detection Circuit and Method" to Hemming et al.

This patent application incorporates by reference herein, in its entirety, U.S. patent application Ser. No. 08/841,095 filed Apr. 29, 1997 to Peck et al. entitled "Peak Tracking Capture Detection Circuit and Method" now U.S. Pat. No. 5,861,013.

FIELD OF THE INVENTION

This invention relates generally to the field of implantable medical devices, and more particularly relates to sense amplifier circuitry for an implantable pulse generator system.

BACKGROUND OF THE INVENTION

Implantable pulse generators (or IPGs) are well known in the prior art. Most demand pacemakers include sense amplifier circuitry for detecting intrinsic cardiac electrical activity so that the devices may be inhibited from generating unnecessary output stimulating pulses when a heart is functioning properly.

Dual-chamber cardiac pacemakers typically have separate sense amplifiers for atrial and ventricular sensing. The sense amplifiers detect the presence of intrinsic signals, that is P-waves occurring naturally in the atrium and R-waves occurring naturally in the ventricle. Upon detecting an intrinsic signal, sense amplifier circuitry generates a digital signal for output to other components which inhibit the delivery of a pacing pulse to the corresponding chamber.

It is desirable to accurately and reliably measure the response of the heart to an electrical stimulation pulse. Measuring such a response permits the determination of a patient's stimulation threshold, or the minimum energy a stimulating pulse must contain for a cardiac response to be evoked. Once a patient's stimulation threshold is determined, the energy content of stimulating pulses may be adjusted to avoid delivering pulses having unnecessarily high energy content. Minimizing the energy content of stimulating pulses is believed to have physiological benefits, and additionally reduces power consumption, a key concern in the context of battery-powered implantable devices.

Detection and measurement of the response of the heart to an electrical stimulating pulse may also be useful in controlling a pacemaker's pacing rate, for ascertaining the physiological effect of drugs or for diagnosing abnormal cardiac conditions.

Immediately following delivery of a pacing pulse to cardiac tissue, a residual post-pace polarization signal (or polarization signal) is generated by the charge induced in the tissue by delivery of a pacing pulse. If the pacing pulse causes an evoked response in the cardiac tissue, then an evoked response signal is superimposed atop the typically much larger amplitude polarization signal. As a result, conventional pacemakers or pacemaker-cardioverter-defibrillators (PCDs) either cannot differentiate, or have difficulty differentiating, between post-pacing pulse polarization signals and evoked response signals. This problem is further complicated and exacerbated by the fact that residual polarization signals typically have high amplitudes even when evoked response signals do occur. Consequently, it becomes difficult, if not impossible, to detect an evoked response signal using a conventional pacemaker or PCD sense amplifier employing linear frequency filtering techniques. As a result, most pacemakers cannot discern between polarization signals and evoked response signals.

Most pacemakers employ sensing and timing circuits that do not attempt to detect evoked response signals until the polarization signal is no longer present or has subsided to some minimal amplitude level; only then is sensing considered reliable. In respect of capture detection, however, such sensing typically occurs a significant period of time after the evoked response signal has already occurred. As a result, most pacemakers cannot detect evoked response signals with any degree of confidence.

The generation and delivery of an electrical heart stimulating pulse gives rise to the storage of charge in body tissues. Such stimulation polarization artifacts, "after potentials," or polarization signals typically have much larger amplitudes than those corresponding to electrical signals arising from an intrinsic heartbeat or a stimulated response. Polarization signals may also interfere with the detection and analysis of a stimulated or evoked response to a pacing pulse. Thus, a need exists in the medical arts for determining reliably whether or not an evoked response signal has occurred in a pacing environment.

Polarization signals typically arise due to the tissue-electrode interface storing energy after a pacing stimulus has been delivered. There are typically two tissue-electrode interfaces in a pacing circuit: one for the tip electrode, and one for the ring (or canister) electrode. The stored energy dissipates after the pace event, creating the after-potential.

In respect of the impedance sensed by a pacemaker's internal circuitry, the total load of the pacing circuit comprises the impedance of the lead itself, the tissue-electrode interface impedances, and the impedance of the body tissue bulk. The impedances of the body tissue and the lead may be modeled as a simple series bulk resistance, leaving the tissue-electrode interfaces as the reactive energy absorbing/discharging elements of the total load. The tip electrode is the primary after-potential storage element in comparison to the case and ring electrodes. In a pacing circuit, a ring electrode typically stores more energy than does a case electrode due to differences in electrode areas.

Several methods have been proposed in the prior art for improving an implantable device's ability to detect and measure evoked responses. is For example, U.S. Pat. No. 5,172,690 to Nappholz et al., entitled "Automatic Stimulus Artifact Reduction for Accurate Analysis of the Heart's Stimulated Response," hereby incorporated by reference herein-its entirety, proposes a tri-phasic stimulation waveform consisting of precharge, stimulus, and postcharge segments. The duration of the precharge segment is varied until the amplitude of the stimulation artifact is small compared to the evoked response.

U.S. Pat. No. 5,431,693 to Schroeppel, entitled "Method of Verifying Capture of the Heart by a Pacemaker," hereby incorporated by reference herein its entirety, discloses a pacemaker that low-pass filters a sensed signal to remove noise and pass frequencies characteristic of the evoked cardiac signal. The filtered signal is processed to render a waveform signal representing the second derivative of the filtered signal. The second derivative filtered signal is further analyzed to detect minimum and maximum amplitude excursions during selected first and second time windows.

The amplitude differences measured during the two time windows are compared to one another to determine whether capture has occurred.

U.S. Pat. No. 5,571,144 to Schroeppel, entitled "Method of Verifying Capture of the Heart by a Cardiac Stimulator," hereby incorporated by reference herein its entirety, discloses a pacer that U.S. Pat. No. 4,114,627 to Lewyn et al., entitled "Cardiac Pacer System and Method with Capture Verification Signal," hereby incorporated by reference herein its entirety, discloses a pacer that delivers output stimulating pulses through an output coupling capacitor. During delivery of a stimulating pulse, the sense amplifier is uncoupled from the cardiac electrode. When the stimulating pulse terminates, the output coupling capacitor is coupled to ground through a discharge resistor, thereby discharging electrode polarization.

German Patent No. 4,444,144 to Hauptmann entitled "Pacemaker with Improved Sensing Circuit for Electrical Signals," hereby incorporated by reference herein in its entirety, discloses a pacemaker having a sensing circuit which records intracardiac heart signals. An adaptive nonlinear noise filter transforms those signals. A matched filter correlates the transformed signals to a pulse pattern and creates an output indicative of heart pulse signals. The sensing circuit reduces faulty signal detection caused by noise filtering by permitting external noise to be distinguished noise associated with true heart signals.

As those of ordinary skill in the art will appreciate readily upon reading the Summary of the Invention, Detailed Description of the Preferred Embodiments and claims set forth below, many of the devices and methods disclosed in the above-noted patents may be modified advantageously by using the teachings of the present invention. What is needed is an implantable pulse generator that is capable of reliably and consistently detecting capture of the heart.

SUMMARY OF THE INVENTION

In the present invention, it was discovered that the potential sensed at the tip electrode immediately following the delivery of a pacing pulse to cardiac tissue tends to move in a negative direction (dV/dt<0). A short period of time thereafter, the sensed signal typically reaches a minimum slope value (dV/dt=0), then moves in a positive direction (dV/dt>0), and finally eventually assumes a zero-amplitude or low-level profile. This behavior was observed to occur in the case of both captured and non-captured pacing pulses; provided, however, that very large pacing energies are not employed. It was further discovered that the rate of change of captured events may be much larger than that corresponding to non-captured events. That is, $dV/dt_{capture} >> dV/dt_{no\ capture}$ in at least some cases.

The circuit and method of the present invention relate to an adaptive nonlinear filtering technique where contributions to the sensed signal relating to a residual polarization signal are rejected, and contributions to the sensed signal relating to an evoked response signal are passed, but only when the evoked response signal has a certain minimum amplitude.

In one embodiment of the present invention, a reference voltage in a capture detection circuit is continuously updated and decreased in value as the sense amplifier tracks the sensed signal provided that dV/dt of the sensed signal is less than zero or substantially less than zero. When or if dV/dt of the sensed signal becomes equal to zero or substantially equal to zero, that reference voltage is held to the minimum value, or "negative peak," it attained during the period of time when dV/dt of the sensed signal was less negative. When or if dV/dt becomes positive or substantially positive thereafter, the difference between the sensed signal and the minimum value attained and tracked previously is amplified. In one embodiment of the present invention the term "negative peak tracking" is used to describe the operation of the foregoing circuit and method.

Once the capture detection circuit of the present invention determines that a "negative peak" has been reached, an output signal corresponding or proportional to the difference between the largest amplitude signal sensed after the "negative peak" and the "negative peak" value itself is amplified and passed into a linear frequency filter circuit for further discrimination. If the pacing pulse did not cause capture of the myocardium, little or no signal is passed by the linear frequency filter circuit to trip one or a series of threshold level comparators. Conversely, if the pacing pulse did cause the myocardium to contract (or capture), a relatively large amplitude signal is passed by the linear frequency filter circuit to trip the one or more threshold comparators. By properly selecting a threshold level for those comparators, the circuit of the present invention may discriminate between captured and non-captured pacing pulses with a high degree of accuracy and reliability.

The present invention includes an adaptive nonlinear filtering technique referred to as "Negative Peak Tracking" (or "NPT") that removes the initial residual polarization signal, and then passes only that portion of the sensed signal where a change in the sign of the slope occurs. The magnitude of the polarization signal has been observed to vary from lead to lead and from patient to patient. Consequently, the amount of polarization existing in a given patient having a given lead must be compensated for. It has been discovered, however, that the magnitude and frequency content of the signal passed by the filter of the present invention depends primarily on the magnitude of the change in the sign of the slope, and not on the degree or amount of polarization. Once the circuit of the present invention detects a change in the sign of the slope, an output signal is passed into a linear frequency filter for further discrimination. If capture has not occurred, the signal passed by the filter and circuit of the present invention is insufficient-in magnitude to trip one or more comparator circuits. Conversely, if capture has occurred, the signal passed by the filter and circuit does trip the one or more comparator circuits. The present invention thus discriminates between captured and non-captured pacing pulses. Judicious selection of comparator threshold levels by a user improves the reliability of event discrimination in the present invention.

The present invention has certain objects. That is, the present invention provides solutions to problems existing in the prior art. It is an object of the present invention to provide an implantable pulse capable of determining reliably and consistently if a given pacing pulse has captured the myocardium and subsequently induced a contraction. It is another object of the present invention to provide an implantable pulse generator having such capture detection capabilities in both unipolar and bipolar lead configurations. It is a further object of the present invention to provide an implantable pulse generator having such capture detection capabilities for both atrial and ventricular applications. It is another object of the present invention to provide an implantable pulse generator having the foregoing characteristics and that is reasonably economical to manufacture.

The present invention has certain advantages. More particularly, the present invention: (a) effectively, reliably and consistently differentiates between post-pace polarizations and evoked potentials; (b) may be employed with unipolar or bipolar implantable pulse generators; (c) may be employed in atrial or ventricular applications; (d) may be employed in implantable pulse generators (IPGs), pacemakers, (PCDs), external pulse generators (EPGs), implantable cardioverter-defibrillators (ICDs), implantable defibrillators, and implantable cardioverters; (e) is economical to manufacture; (f) helps reduce health care costs, and (o) increases patient safety owing to increased reliability and consistency in differentiating evoked responses and post-pace polarizations.

In one embodiment of the present invention, discrimination between evoked response and the post-pace polarization is achieved by noting the polarity of the positive or negative change in voltage in respect of time (or dV/dt) of the waveform incident on the lead electrodes during a short period of time immediately following the paced event (hereinafter referred to as a "capture detect window" or "CDW"). More particularly, the post-pace polarization signal exhibits a constant polarity during the capture detect window, and the evoked response may cause the polarity of that signal to reverse during the CDW. The sign of the post-pace polarization polarity, either positive or negative, is determined by the design of the specific output circuitry. The evoked response may reverse the polarity of the sensed signal in either case, from positive to negative or from negative to positive, during the window of interest.

In another embodiment of the present invention, and when the magnitude of the post-pace polarization is so great that the evoked response cannot reverse the polarity of the waveform, discrimination of the evoked response is achieved by noting an acceleration (or increasing magnitude of dv/dt) in the sensed signal or waveform. During the capture detect window, the polarization of that signal will not only exhibit a constant polarity, but also a continuous deceleration (or decreasing magnitude of dv/dt). The evoked response thus creates an "acceleration" in the sensed signal or incident waveform that is detected by the circuitry and method of the present invention.

In accordance with the foregoing concepts, a peak-tracking circuit may be employed in the present invention which detects a reversal in the input waveform polarity (which in turn is an artifact of post-pacing electrode polarization), and thus filters out the post-pace polarization artifact while permitting the evoked response to propagate through the sense amplifier. In addition, a secondary peak tracking circuit may be employed which detects an acceleration in the input waveform by monitoring the feedback current in the first peak tracking circuit.

Other objects, features and advantages of the present invention will become apparent upon referring to the appended drawings, detailed description of the preferred embodiments and the claims.

DETAILED DESCRIPTION OF THE PREFERRED EMBODIMENTS

The term "capture" as used in the specification and claims hereof means the successful evocation of a stimulated response in cardiac tissue by a pacing pulse. Conversely, the term "non-capture" as used in the specification and claims hereof means the delivery of a pacing pulse to cardiac tissue that evokes an insufficient or weak stimulated response, or that evokes no stimulated response at all.

The terms "peak tracking circuit," "capture detect circuit," "capture detection circuit" and "capture detector" as used in the specification and claims hereof are synonymous with one another and mean any of a number of various embodiments of the circuit of the present invention, incorporated into an implantable medical device, that detects capture (or an evoked response or contraction) of the heart caused by the delivery of an electrical stimulus to cardiac tissue provided by a pacemaker, an implantable pulse generator (IPG), a pacemaker-cardiodefibrillator (PCD) or any other cardiac stimulator.

Figure 1:
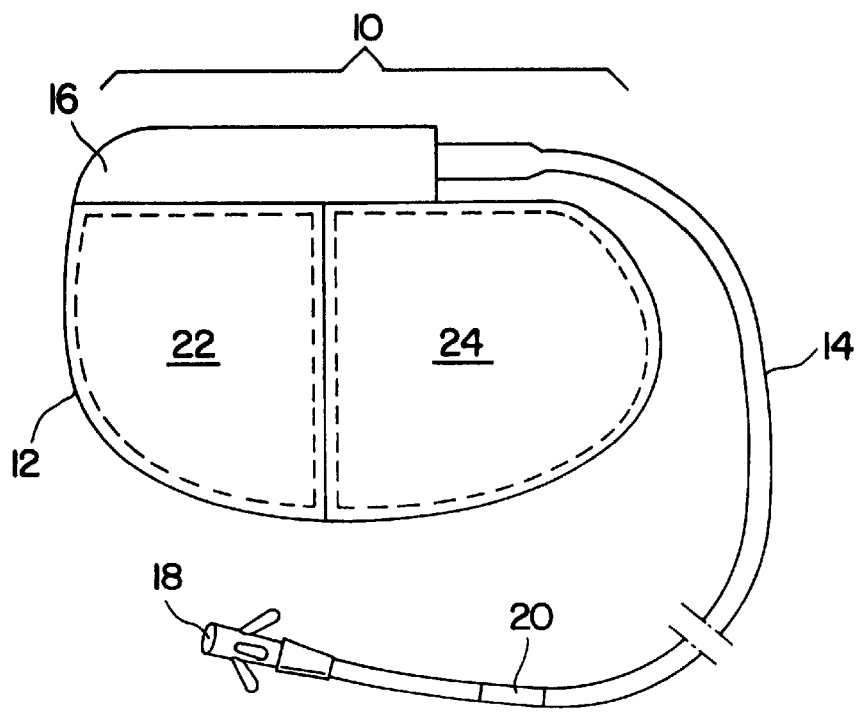
FIG. 1 shows an implantable pacemaker system constructed in accordance with one embodiment of the present invention.

FIG. 1 shows implantable pacemaker system 10 constructed in accordance with one embodiment of the present invention. Pacemaker system 10 includes a pulse generator housed within a hermetic enclosure 12, and a flexible, elongate lead 14 coupled to a header or connector block assembly 16 attached or coupled to pulse generator enclosure 12. Enclosure 12 is preferably formed of titanium or any other suitable biocompatible material or metal. Header 16 is preferably formed of polyurethane or any other suitable biocompatible material or metal. In accordance with conventional practice, lead 14 comprises one or more electrical conductors insulated with a flexible outer sheath formed of biocompatible silastic, silicone rubber, polyurethane or the like. Lead 14 generally has one or more electrodes disposed at or near the distal end thereof. FIG. 1 shows lead 14 as a bipolar lead having tip electrode 18 and ring electrode 20. Other types of leads such as unipolar leads may be employed in conjunction with the present invention.

Header 16 encases one or more hermetic feedthrough elements (not shown in the Figures) for enabling electrical signals to be communicated between the conductors of lead 14 and electronic stimulation and control circuitry 22 disposed within hermetic enclosure 12. Also disposed within hermetic enclosure 12 is a battery 24 for providing power to the various electronic components of pacemaker system 10.

Figure 2:
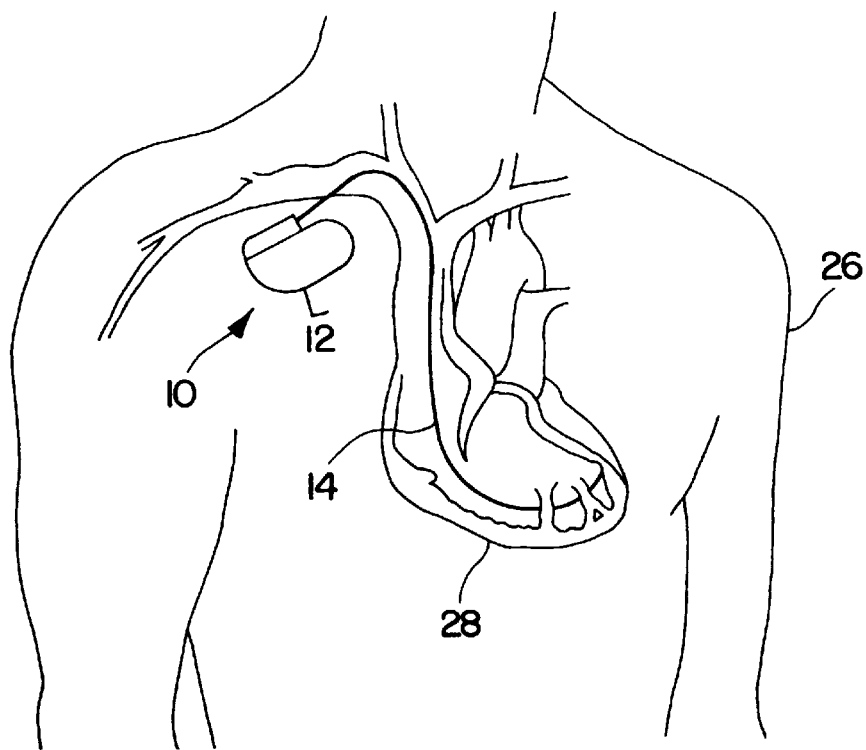
FIG. 2 shows the pacemaker system of FIG. 1 implanted in a human being.

FIG. 2 shows a conventional lateral transvenous implantation of pacemaker system 10 within the body of patient 26. Hermetic enclosure 12 is disposed within a small subcutaneous pocket inferior to the patient's clavicle. Lead 14 extends transvenously from enclosure 12 such that its distal end is disposed within heart 28 of patient 26.

Figure 3:
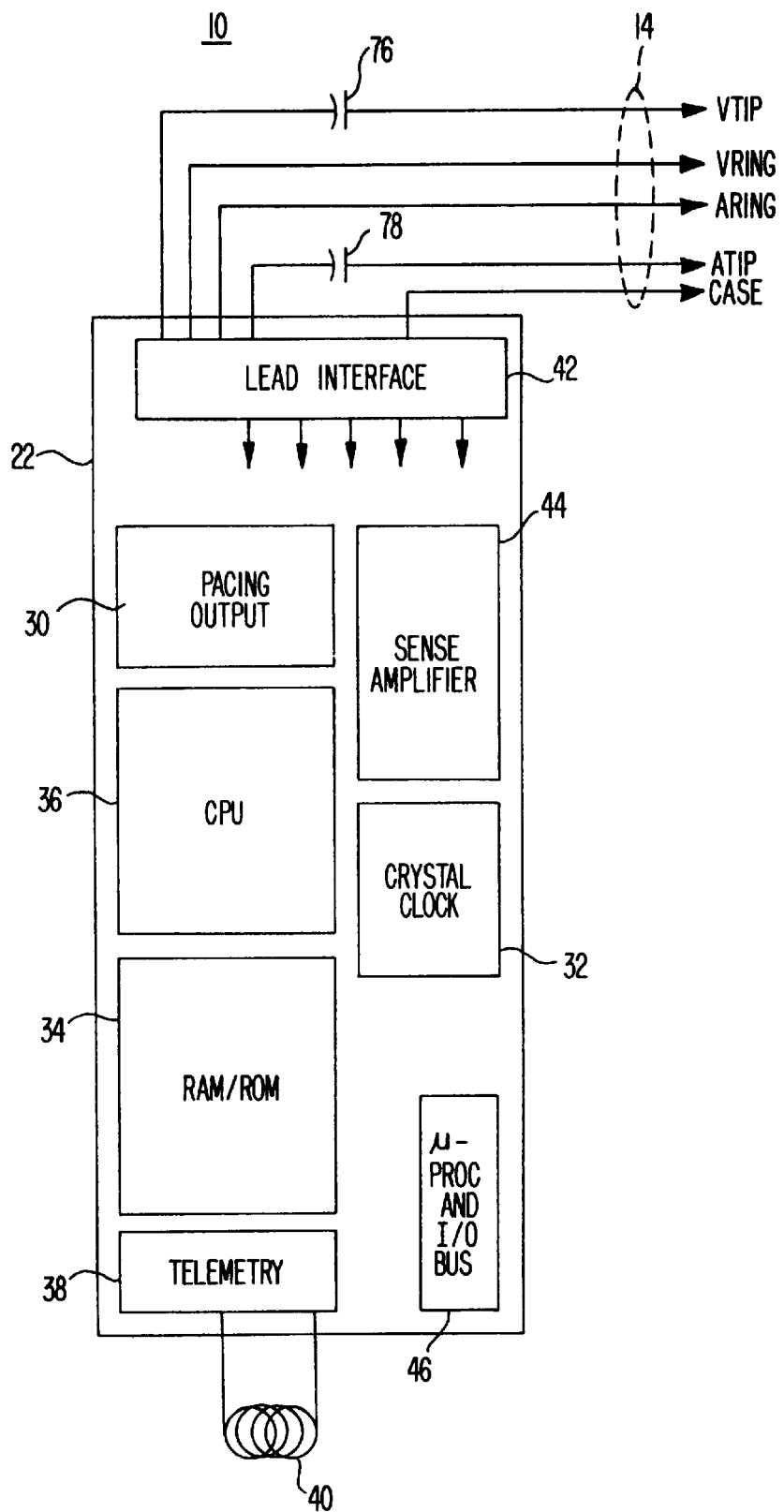
FIG. 3 shows a functional block diagram corresponding to the pacemaker circuitry of the pacemaker system of FIG. 1.

FIG. 3 shows a functional block diagram of pacemaker system 10 having one embodiment of electronic stimulation and control circuit 22 for controlling pacing and sensing functions. Stimulation and control circuit 22 may be of conventional design such as that disclosed in U.S. Pat. No. 5,052,388 to Sivula et al., entitled "Method and Apparatus for Implementing Activity Sensing in a Pulse Generator", which patent is hereby incorporated by reference herein in its entirety. To the extent certain components of pacemaker system 10 are conventional in their design and operation, those components are not described here in great detail as the design and implementation of such components is well known to those of ordinary skill in the art. For example, stimulation and control circuit 22 in FIG. 3 includes stimulating pulse output circuitry or pacing output circuit 30, crystal clock or oscillator 32, random-access memory and read-only memory (RAM/ROM) unit 34, telemetry unit 38, lead interface unit 42 and central processing unit (CPU) 36, all of which are well-known in the art.

Pacemaker system 10 includes internal communication and telemetry circuit 38 that permits system 10 to communicate with an external programming and control unit that is not shown in the Figures. Associated with communication circuit 38 is radio-frequency antenna 40 for facilitating the receipt and transmission of radio-frequency signals, in accordance with conventional practice and as exemplified by the teachings of U.S. Pat. No. 4,374,382 to Markowitz, entitled "Marker Channel Telemetry System for a Medical Device," U.S. Pat. No. 5,127,404 to Wyborny et al., entitled "Telemetry Format for Implanted Medical Device," and U.S. Pat. No. 4,556,063 to Thompson et al., entitled "Telemetry System for a Medical Device." The foregoing '382, '404 and '063 patents are hereby incorporated by reference herein in their respective entireties.

In one embodiment of the invention, CPU 36 is a custom microprocessor adapted to fetch and execute instructions stored in RAM/ROM unit 34 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of CPU 36. Furthermore, while we describe the present invention here in the context of an automatic, implantable pacemaker system, it is contemplated that the present invention may find beneficial application in automatic medical device systems other than pacemakers such as external and implantable defibrillators, tachycardia conversion devices, and other devices.

FIG. 3 further shows stimulation and control circuit 22 coupled to one or more leads 14 that upon implantation extend transvenously between the implant site of pulse generator system 10 and heart 28. Physical connections between lead 14 and the various internal components of circuitry 22 are established and facilitated by conventional connector block assembly 16 shown in FIG. 2. Electrical connections between the conductor or conductors of lead 14 and stimulation and control circuit 22 are established and facilitated by lead interface circuit 42.

Circuit 42 typically functions in a multiplexer-like manner to selectively and dynamically establish electrical connections between and to various conductors in leads 14. For example, electrical connections to atrial tip or ring electrode conductors ATIP and ARING, or ventricular tip or ring electrode conductors VTIP and VRING, may be established through lead 14 by lead interface circuit 42.

For the sake of clarity specific connections between the conductors of lead 14 and the various components of stimulation and control circuitry 22 are not shown in FIG. 3.

Those of ordinary skill in the art will understand, however, that conductors in lead 14 must be coupled directly or indirectly to sense amplifier circuit 44 and stimulating pulse output circuit 30 to permit the routing of sensed cardiac electrical signals to sensing circuit 44, and the delivery of stimulating pulses to cardiac tissue via lead 14.

Stimulation and control circuit 22 contains central processing unit (CPU) 36, which may comprise an off-the-shelf programmable microprocessor or microcontroller. In a preferred embodiment of the present invention, CPU 36 is a custom integrated circuit. Although specific connections between CPU 36 and other components of stimulation and control circuit 22 are not shown in FIG. 3, CPU 36 controls the timed operation of stimulating pulse output circuit 30 and sense amplifier circuit 44 under the control of programming stored in RAM/ROM unit 34.

Crystal oscillator or clock 32 provides main timing clock signals to stimulation and control circuit 22, and is most preferably a 32,768-Hz crystal-controlled oscillator. The specific lines over which clocking signals are provided to the various timing components of stimulation and control circuitry 22 such as CPU 36 are omitted from FIG. 3 for the sake of clarity.

Other interconnections between the individual components of stimulation and control circuit 22 are represented by microprocessor and I/O bus block 46 in FIG. 3. For example, a connection between CPU 36 and pacing output circuit 30 is preferred such that CPU 36 provides triggering or inhibiting signals to output circuit 30 for controlling the delivery of stimulating pulses to heart 28. For the sake of clarity, those interconnections are not shown in FIG. 3.

The various electrical and electronic components of pacemaker system 10 shown in FIG. 3 are powered electrically by battery 24 (shown in FIG. 1, but not shown in FIG. 3). As depicted in FIG. 1, battery 24 is contained within hermetic enclosure 12 of pacemaker system 10. FIGS. 1 and 2 do not show the specific connections between battery 24 and other components of pacemaker system 10.

Stimulating pulse output circuit 30 generates cardiac stimuli in response to control signals originating in CPU 36, and may be of the type disclosed in U.S. Pat. No. 4,476,868 to Thompson, entitled "Body Stimulator Output Circuit," which patent is hereby incorporated by reference herein in its entirety. Many other types of pacing output circuits are suitable when practicing the present invention.

Sense amplifier circuit 44 receives electrical cardiac signals from lead 14 and processes those signals to derive event-indicating signals that mark the occurrence of specific cardiac electrical events such as atrial contractions (P-waves) and ventricular contractions (R-waves). Those event-indicating signals are provided to CPU 36 for use in controlling the synchronous stimulating operations of pacemaker system 10. Additionally, the event-indicating signals may be communicated by uplink RF transmission to an external programming unit for visual display to a physician.

Pacemaker system 10 may include numerous other components and subsystems such as, for example, activity sensors and associated circuitry. The presence or absence of those additional components in pacemaker system 10, however, is not highly pertinent to the present invention which relates primarily to the implementation and operation of sense amplifier circuit 44.

Figure 4:
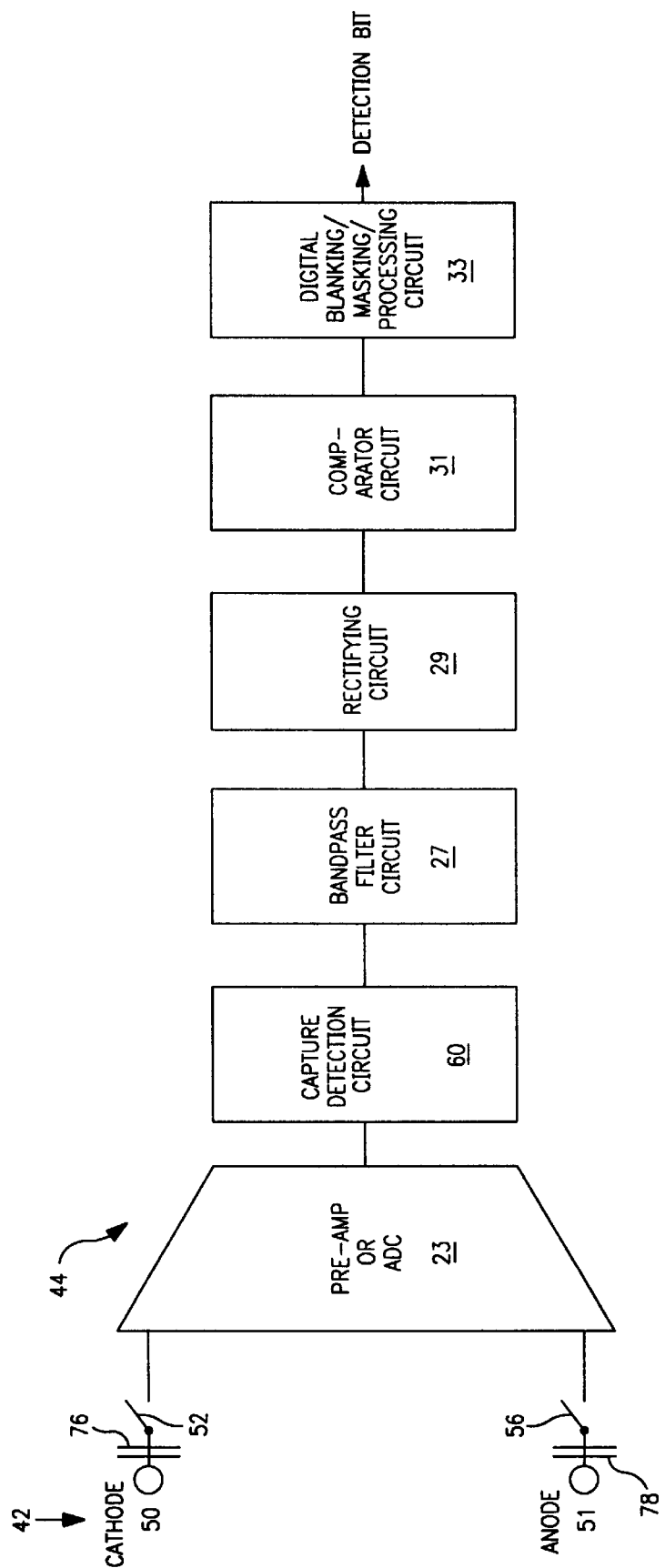
FIG. 4 shows a functional block diagram of one embodiment of the capture detection circuit of the present invention.

FIG. 4 shows a functional block diagram of sense amplifier circuit 44 comprising anode 51 and cathode 50 of lead 14, pre-amp circuit 23, capture detection or peak tracking circuit 60, band-pass filter circuit 27, rectifier circuit 64, comparator circuit 31 and digital blanking/masking/processing circuit 33. Cardiac signals senses by lead 14 progress from left to right through circuit 44 from anode 51 and cathode 50 to digital blanking/masking/processing circuit 33.

In a preferred embodiment of the present invention, largely or wholly analog components comprise pre-amp circuit 23, band-pass filter 27, rectifier circuit 64 and comparator circuit 31. Completely or partially digital implementations of circuit 44 are equally tenable, however, where, for example, an analog-to-digital converter may be substituted for pre-amp circuit 23.

Anode 51 and cathode 50 are preferably ac-coupled to body tissue, thereby permitting the automatic rejection filtering of any DC bias shifts in body potential that may occur. Blanking is typically provided to prevent pacing pulse energy from saturating sense amplifier circuit 44.

Peak tracking circuit 60 is an important component of the present invention and is described below in greater detail. Peak tracking circuit 60 may be implemented using wholly digital circuitry and components, wholly analog circuitry and components, or some mixture of analog and digital circuitry and components.

Band-pass filter circuit 27 is not required to practice the present invention, but is desirable to include in circuit 44 because it rejects undesired low- and high-frequency components of input signals, and also increases the signal-to-noise ratio (SNR) of coherent components of those input signals. Band-pass filter circuit 27 may be implemented in analog form or digitally. For example, in an analog implementation band-pass filter circuit 27 may comprise one or more switched capacitors, and in a digital implementation may comprise any one of several widely and commercially available digital signal processing chips (DSPs).

Rectifier circuit 64 is not required to practice the present invention. When used, however, rectifier circuit 64 simplifies the design and complexity of comparator circuit 31. The rectifier circuit of the present invention may be implemented in analog or digital embodiments.

Depending on the particular embodiment of the present invention in use, significant digital signal processing of signals received from rectifier circuit 64, band-pass filter circuit 27 or capture detection circuit 60 may be accomplished in digital blanking/masking/processing circuit 31 before an output signal or detection bit is generated.

Figure 5A:
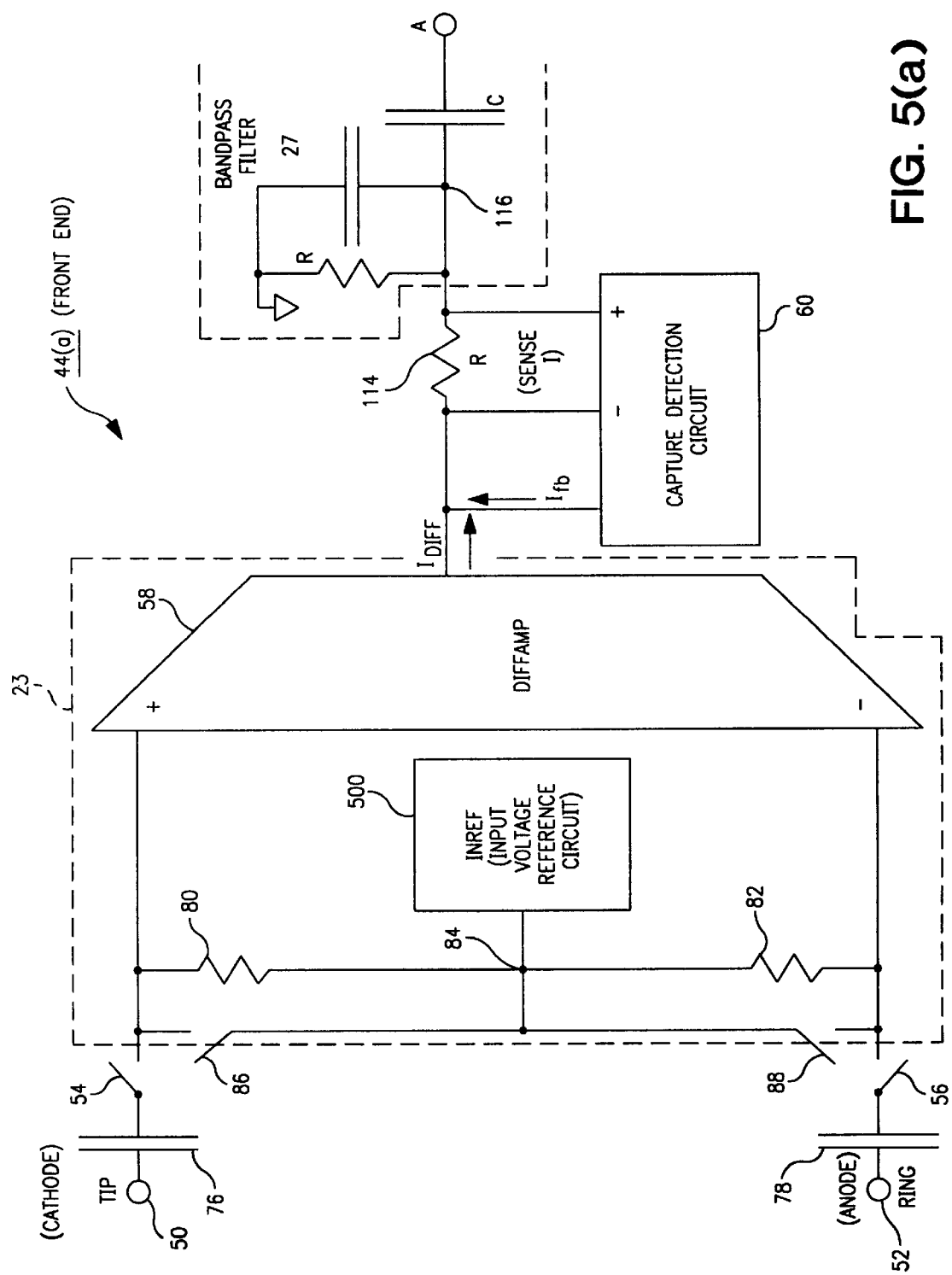
FIG. 5(a) shows a general schematic functional block diagram of the front end of one embodiment of the sense amplifier of the present invention.
Figure 5B:
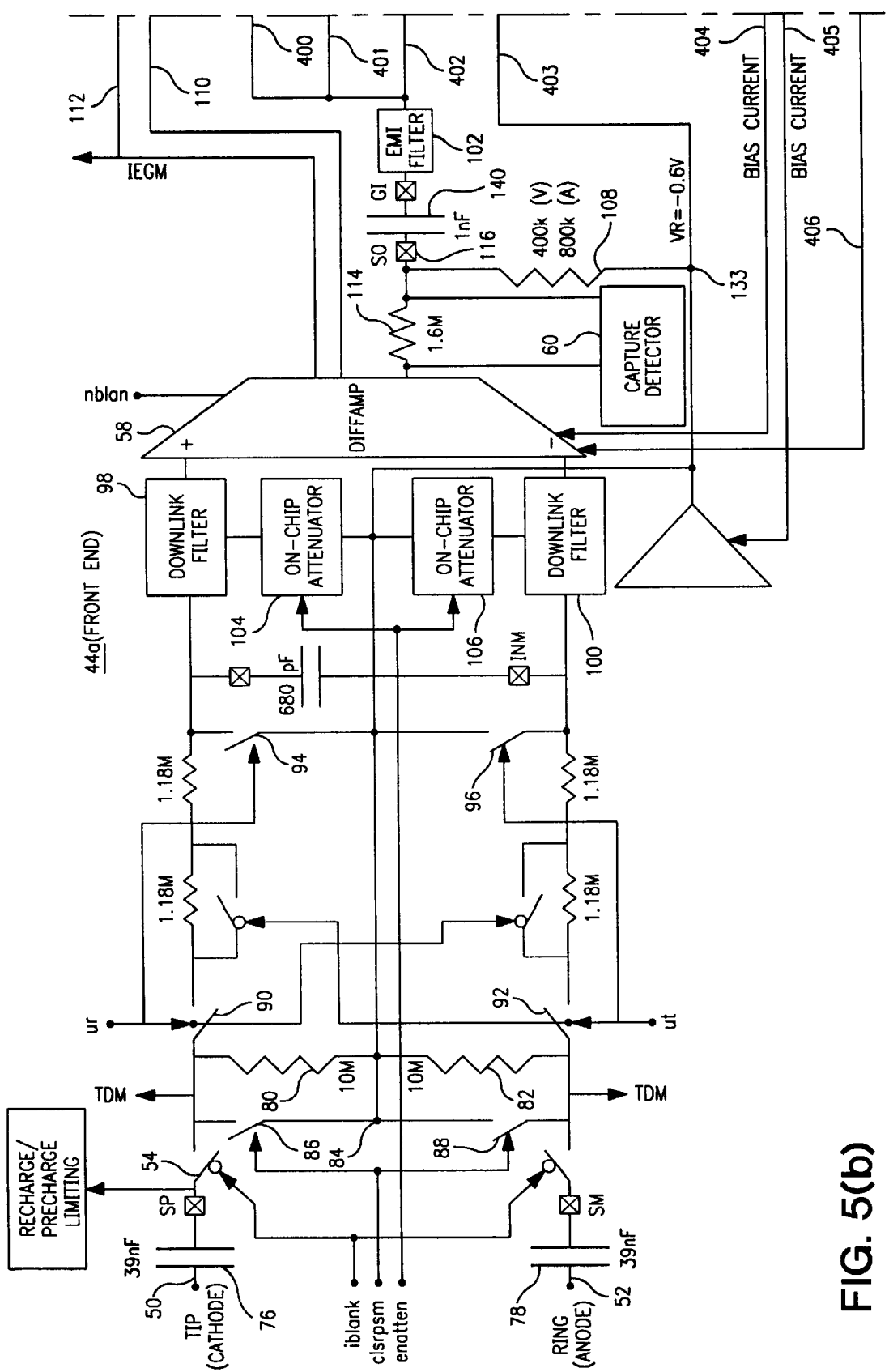
FIG. 5(b) shows a circuit diagram of one particular embodiment of the front end shown in FIG. 5(a)
Figure 6A:
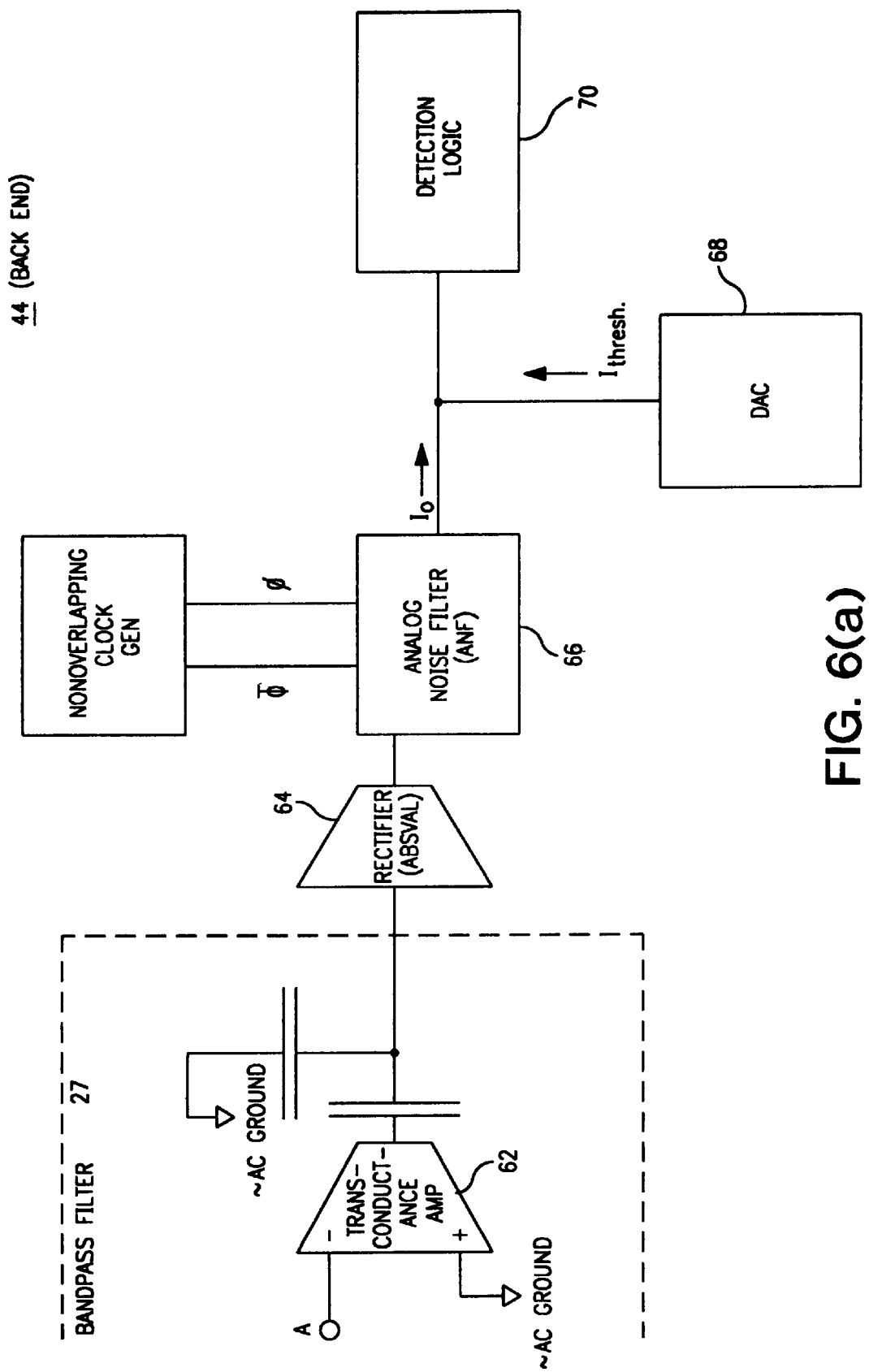
FIG. 6(a) shows a general schematic functional block diagram of the back end of one embodiment of the sense amplifier of the present invention.
Figure 6B:
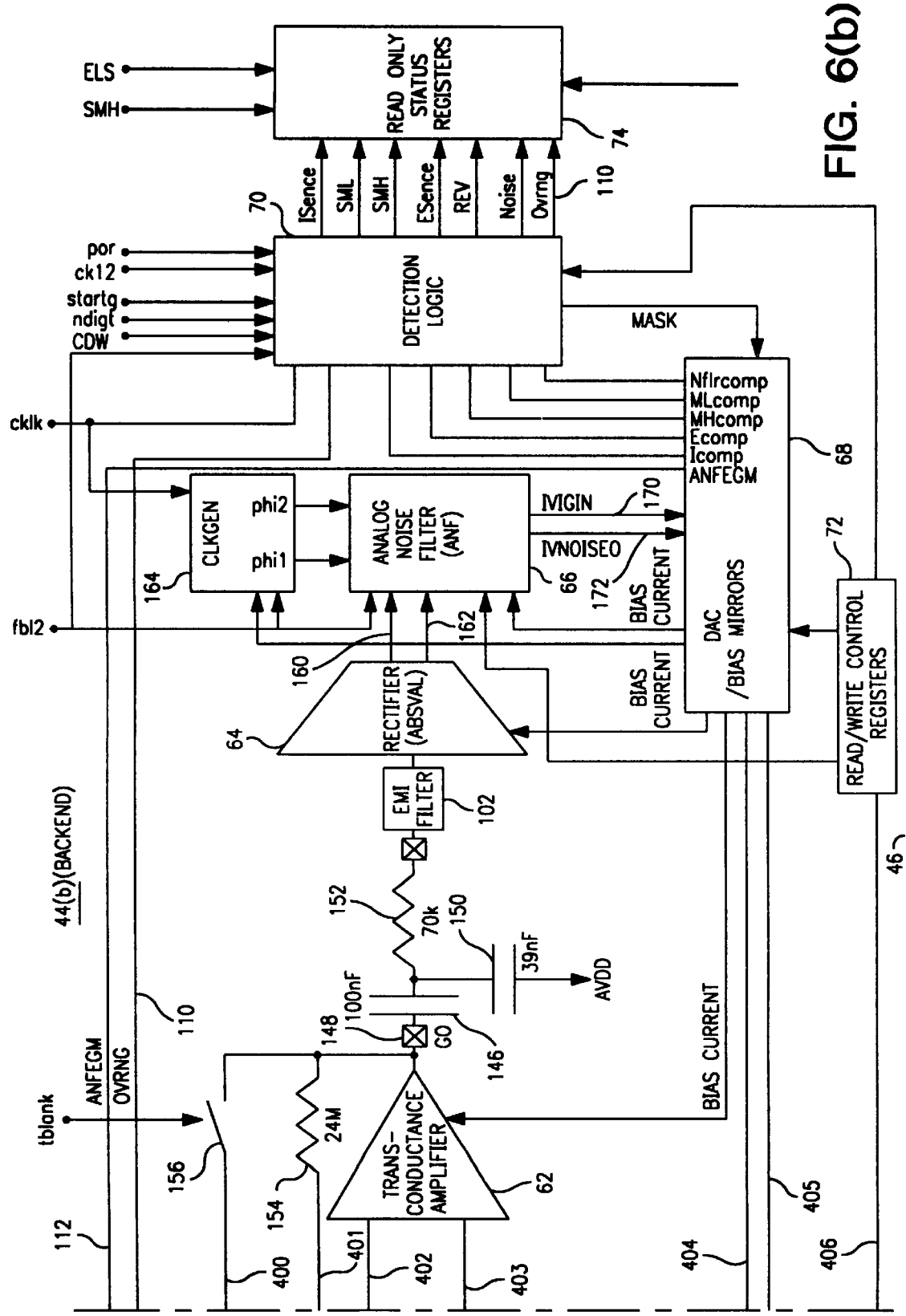
FIG. 6(b) shows a circuit diagram of one particular embodiment of the back end shown in FIG. 5(a)

FIG. 5(a) shows a general schematic functional block diagram of front end 44(a) of one embodiment of sense amplifier 44 of the present invention. FIG. 5(b) shows a circuit diagram of one particular embodiment of front end circuit 44(a) shown in FIG. 5(a). FIG. 6(a) shows a general schematic functional block diagram of back end 44(b) of one embodiment of sense amplifier circuit 44 of the present invention. FIG. 6(b) shows a circuit diagram of one particular embodiment of back end 44(b) shown in FIG. 6(a). FIGS. 5(a) and 6(b) together represent a complete general schematic functional block diagram of a preferred embodiment of sense amplifier circuit 44. FIGS. 5(b) and 6(b) together comprise a complete circuit diagram of a preferred, particular embodiment of the present invention. The following discussion refers to FIGS. 5(a), 5(b), 6(a) and 6(b).

Sense amplifier circuit 44 detects the presence of cardiac signals. In a preferred embodiment of the present invention, sense amplifier circuit 44 comprises separate, substantially identical atrial and ventricular sense amplifiers; for purposes of clarity, only one of those sense amplifier circuits is shown in FIGS. 5(a) through 6(b). Sense amplifier circuit 44 is preferably configured to detect the presence of intrinsic atrial and ventricular signals. Upon detecting such an intrinsic signal, sense amplifier 44 generates at least one digital output signal that is conveyed to CPU 36, which in turn delivers an output for inhibiting the delivery of a pacing pulse or generating appropriate pacing therapy.

In accordance with one aspect of the present invention, and as described below in further detail, sense amplifier circuit 44 is further capable of detecting the presence of a cardiac evoked response (or an electrical signal arising from atrial or ventricular cardiac tissue contracting in response to the delivery of a pacing pulse). Upon detecting such an evoked response, sense amplifier circuit 44 provides an output of at least one digital logic signal for indicating the detection of an evoked signal. Sense amplifier circuit 44 may be configured to detect either an intrinsic signal or an evoked response signal, or both. It is an advantage of the present invention that the additional circuitry required in circuit 44 for evoked response signal detection is minimally more than that required for intrinsic signal detection capabilities alone.

In a preferred embodiment of the present invention, sense amplifier circuit 44 may be powered down and have its logical output enabled or disabled. No output logic signals indicating intrinsic signal detection are preferably generated by circuit 44 when the sense amplifier output is disabled, or when sense amplifier 44 is powered down. The evoked response signal detection capability of sense amplifier 44 is also preferably programmable such that when logical outputs are disabled or circuit 44 is powered down, no output indicating evoked response signal detection is generated.

Sense amplifier circuit 44 preferably has the capability of sensing, evoked response and intrinsic signals when lead 14 has any one of the following configurations: single electrode configuration (i.e., tip-to-case or ring-to-case electrode configuration), dual electrode configuration (i.e., tip-to-ring electrode configuration), or configurations having more than two electrodes. Sense amplifier circuit 44 preferably senses both positive and negative polarity input signals.

In a preferred embodiment of the present invention, a minimum signal duration of one millisecond and a predetermined minimum signal amplitude are required before an input signal may be considered as a potential detected intrinsic or evoked response signal. The predetermined minimum signal amplitude is generally determined by the sensitivity threshold of the sense amplifier, and is preferably a programmable parameter of pacemaker system 10. The sensitivity threshold is preferably applied to any polarity signal when any electrode configuration is employed. The status of intrinsic or evoked response signal detection may be ascertained by reading via telemetric means the contents of status registers contained in CPU 36.

To permit external, non-invasive observation of electrical signals arising in the heart (e.g., the observation of electrograms or EGMs), sense amplifier circuit 44 preferably provides an output analog signal that is digitized and subsequently telemetered to an external apparatus via telemetry system 38. EGMs preferably have an array of different programmable gain settings associated with them. Generation of EGMs in pacemaker system 10 is preferably enabled and disabled by writing to appropriate control registers in CPU 36.

FIGS. 5(a) and 5(b) together show the front end of sense amplifier circuit 44. TIP (or cathode) and RING (or anode) inputs 50 and 52, respectively are coupled to the tip and ring electrodes, respectively, of lead 14. (Again, it is to be-understood that preferably there are separate atrial and ventricular sense amplifier circuits 44 in pacemaker system 10; the front end of atrial sense amplifier circuit 44 is coupled to ATIP and ARING conductors of lead 14, and the front end of ventricular sense amplifier circuit 44 is coupled to VTIP and VRING conductors of lead 14.)

Front end circuit 44(a) and back end circuit 44(b) of sense amplifier circuit 44 preferably include the following components: (a) switches 54 and 56 for blanking sense amplifier circuit 44 in response to receipt of an IBLANK input signal; (b) differential amplifier (DIFFAMP) circuit 58 for converting the differential electrode signals to a single-ended signal; (c) capture (or evoked response) detection circuit 60; (d) band-pass filter circuit 27 comprising TRANSAMP 62 for rejecting unwanted signals; (e) rectifier circuit 64 for rectifying the signal, which in a preferred embodiment of the present invention is an ABSVAL processor or op-amp circuit; (f) analog noise filter (ANF) circuit 66 for rejecting continuous wave noise; (g) a series of amplitude comparators (DAC) 68; and (h) detection logic (DETLOGIC) circuit 70. Sense amplifier circuit 44 is controlled through read/write registers 72 accessible by CPU 36 over microprocessor and I/O bus 46. Similarly, digital logic output signals from sense amplifier 44 are accessible through read-only registers 74 which are also connected to bus 46.

TIP and RING inputs 50 and 52 are preferably coupled to sense amplifier 44 through 39 nF capacitors 76 and 78, respectively. Two 10 MΩ resistors 80 and 82 provide a predetermined reference bias voltage at node 84, and further form a 0.4 Hz high-pass filter in conjunction with capacitors 76 and 78. Reference bias node 84 is held at approximately 600 mV below analog ground (AVDD).

In one embodiment of the present invention, switches 54 and 56 are P-channel transistors; any other type of suitable solid-state transistor or switch may be employed. Switches 54 and 56 are preferably controlled by input signal IBLANK, and in response to receiving such a signal decouple sense amplifier circuit 44 from inputs TIP and RING prior to the onset of a pacing sequence. Following delivery of a pacing pulse, switches 54 and 56 recouple the TIP and RING inputs to circuit 44. It is preferred that switches 86 and 88 be controlled by input signal CLRSPSM and short the inputs of sense amplifier circuit 44 to reference bias node 84 during blanking. This prevents the generation or output of extraneous signals. Switches 54, 56, 86 and 88 preferably open and close in a sequence coordinated to reestablish a predetermined DC reference bias voltage for coupling capacitors 76 and 78 after those capacitors have been recharged or precharged. The predetermined DC reference bias voltage is generated by connecting capacitors 76 and 78 directly to reference bias node 84 in an appropriate manner and sequence. This switching and biasing technique minimizes the generation of recoupling artifacts after pacing pulses have been delivered.

The sensing configuration of sense amplifier circuit 44 is preferably determined by another set of P-channel switches 90, 92, 94 and 96 controlled by signals UR and UT and disposed in the front end of sense amplifier circuit 44. In accordance with known pacing practices, those switches effect bipolar sensing between the tip and ring electrodes of lead 14, or effect unipolar sensing between the tip and case electrodes (where the conductive canister of the implanted device functions as a common or indifferent electrode) or between the ring and case electrodes. In all three electrode configurations the case is grounded. The case becomes a floating ground only when a-bipolar sensing configuration is employed and when precharge, pace and recharge operations are being executed. The three possible electrode sensing configurations combined with the two control signals UR and UT create four binary logical combinations. The remaining (and otherwise unused) fourth logical combination is preferably employed to control powering down of sense amplifier circuit 44.

Downlink filters 98 and 100 reduce the opportunity for pacemaker system 10 to become inhibited due to downlink bursts of RF energy, and are disposed in the front end of sense amplifier 44. Filters 98 and 100 preferably comprise a cascade of two low-pass filters formed of on-chip resistors and capacitors. Similar filters 102 are preferably placed at the input of each circuit block of sense amplifier circuit 44.

The testability of sense amplifier circuit 44 is enhanced by on-chip attenuators 104 and 106 that permit large-amplitude, high SNR input test signals to be attenuated by a predetermined amount. Attenuators 104 and 106 are formed by resistive voltage divider circuits, each such circuit comprising a series-connected downlink filter resistor element and a shunt resistor element connected to the input voltage reference. Attenuators 104 and 106 are enabled by signal ENAT-TEN which turns on a P-channel switch in series with a shunt resistance. In the presently preferred embodiment of the invention, the attenuation ratio is 20:1, or about 26 dB.

Input signals to sense amplifier circuit 44 are converted from differential to single-ended signals in DIFFAMP 58. Most preferably, DIFFAMP 58 is a transconductance amplifier whose transconductance is inversely proportional to the value of a high-precision CrSi resistor. The transconductance of DIFFAMP 58 preferably has two different values corresponding to 5/R, where R=[lo_gain, hi_gain]. The specific value of R is preferably selected in conjunction with the sensitivity setting of digital-to-analog converter (DAC) 68.

The output of DIFFAMP 58 is loaded by resistor 108 (most preferably a high-precision CrSi resistor) having a resistance of about 400 kΩ for sense amplifier 44 in the ventricle channel and about 800 kΩ for sense amplifier 44 in the atrial channel. This output loading works in conjunction with the transconductance selection to set the voltage gain of DIFFAMP 58. Because the matching tolerance of the CrSi resistors is relatively good, the voltage gain of DIFFAMP 58 is quite consistent.

An over-range detect signal (OVRNG) on line 110 prevents sense amplifier 44 from outputting a detect signal in the event a common mode over-range condition exists. When an over-range condition does occur, the condition is recorded in a sense status register included in read-only status register block 74. The corresponding over-range status bit is cleared when the register is read. DIFFAMP block 58 also has an additional current output (IEGM) which is sent on line 112 to the measurement system as an EGM signal. This current is scaled to match the input range of a delta-mod converter. Most preferably, the converter may select four different full-scale ranges. Through programmable control the IEGM signal can be substituted with the current signal input to DAC 68, thereby permitting a user to observe the actual post-processed signal that the sense amplifier employs using to determine capture detection.

Capture detection is the determination of whether or not a delivered pacing stimulus causes the myocardium to contract. In accordance with an important aspect of the present invention, capture detection is accomplished by circuitry that includes sense amplifier 44 and capture detection circuit (CDC) 60. Additional output circuitry may be employed to enhance capture detection capabilities by reducing the effects of after potential signals.

One challenge of capture detection is to discriminate successfully between an evoked response signal and an after-potential artifact signal created by the tissue-electrode interface. In accordance with one aspect of the present invention, after-potential artifact signal rejection is accomplished by peak tracking the pacing electrode potential with respect to $V_{DD}$. During the capture detect window, the operation of the output circuitry and the nature of the tissue-electrode interface are such that the after-potential generally presents itself as a negatively pseudo-exponentially decaying artifact across the pacing electrode and indifferent electrode.

CDC circuit 60, therefore, is most preferably a negative peak tracking (NPT) circuit which peak tracks the current output of DIFFAMP 58 through a 1.6 MΩ resistor 114 and subtracts the peak-tracked after-potential signal from the sense signal output by DIFFAMP circuit 58. In other words, CDC circuit 60 detects changes in the polarity of the output of DIFFAMP circuit 58, where the term "polarity" refers here to the sign of the derivative (dv/dt) of the output signal provided by DIFFAMP circuit 58. Because the after-potential signal typically Manifests itself as a pseudo-exponentially decaying artifact, any change in the polarity of the output provided by DIFFAMP circuit 58 may be attributed to an evoked response signal. By filtering out or subtracting the evoked response signal from the output of DIFFAMP circuit 58, the only current entering sense-output (SO) node 116 relates to signal deflections that are in a direction opposite to that of the tracking signal. Any artifact substantially attributable to the post-pace electrode polarization signal is thus filtered out.

FIGS. 6(a) and 6(b) show band-pass filter circuit 27 as having two poles. High-pass pole corner frequencies are determined by the values of series capacitor 140 between nodes SO 114 and GI 142, and series capacitor 146 connected to node GO 148. Low-pass pole corner frequencies are determined by the values of the front-end differential capacitor discussed previously and the shunt capacitor connected to the output of TRANSAMP 62. Filtering provided by capacitors 146 and 150 at the output of TRANSAMP 62 is characterized in having corner frequencies determined predominantly by high accuracy 70 kΩ off-chip resistor 152. Capacitors 140, 148 and 150 are selected to create a two-pole band-pass filter with corner frequencies of 18.5 Hz and 58.5 Hz. Identical or substantially similar filter circuit topologies may be employed for both atrial and ventricular amplifiers 44. Feedback resistor 154 of TRANSAMP 62 is shunted by P-channel switch 156 as part of the sense amplifier blanking circuit. P-channel switch 156 is controlled by a signal TBLANK, and effectively attenuates the signal through the band-pass filter when enabled.

The output current provided by band-pass filter circuit 27 and TRANSAMP 62 is connected to the input of a low input impedance current rectifier circuit 64 (ABSVAL) through off-chip 70 KΩ resistor 152. The main purpose of rectifier circuit 64 is to convert its input to a single ended signal and to thereby remove or reduce sensitivity to signal polarity. Two separate rectified output signals are provided by rectifier circuit 64 on lines 160 and 162. These output signals are routed to analog noise filter (ANF) circuit 66 for subsequent processing.

The rectified output from ABSVAL circuit 64 appearing on line 160 is fed directly into the input of ANF circuit 66. ANF circuit 66 is a current mode peak tracking circuit whose output is filtered through a low-pass switched-capacitor filter circuit. CLKGEN circuit 164 supplies a 1 kHz nonoverlapping clock signal (PHI1 and PHI2) for the low-pass switched-capacitor filter circuit. ANF circuit 66 produces a DC current whose magnitude is proportional to the peak signal amplitude of any continuous incoming noise. This continuous noise floor signal is then subtracted from the second output of ABSVAL circuit 64 appearing on line 162, thereby eliminating that portion of the signal due to the continuous noise signal. The result of this subtraction process is fed into the input of comparator circuit 68 on IVIGIN line 170. In accordance with this aspect of the present invention, only spontaneous events whose magnitudes exceed those of the noise source (e.g., spontaneous cardiac events) are passed along to threshold comparator 68.

In addition to the IVIGIN signal appearing on line 170, continuous noise floor signal (IVNOISE0) is also input to comparator circuit on line 172. The IVNOISE0 signal is compared against a multiple of a current sensitivity setting to provide a means of determining whether an excessively noisy signal is present. If so, any automatic adjustment of the sensing threshold by control circuitry in pacemaker 10 is preferably suspended until a more reliable, less noisy signal is obtained.

DAC circuit 68 contains a set of bias mirrors for scaling the main sense amplifier bias current and for supplying bias current to other circuit blocks within the sense amplifier. DAC 68 comprises five separate current comparators for determining the signal amplitude thresholds corresponding to a plurality of different sensed events. Intrinsic sensed events are indicated by assertion of signal ICOMP. Sense margin low amplitude events are indicated by assertion of signal MLCOMP. Sense margin high amplitude events are indicated by assertion of signal MHCOMP. Evoked response events are indicated by assertion of signal ECOMP. Noise floor exceeded conditions are indicated by assertion of signal NFLRCOMP. The first four of the foregoing comparisons are made relative to the IVIGIN signal. The last of the foregoing comparisons is made with respect to the IVNOISE0 signal.

The threshold level for the intrinsic comparator determines the sensitivity of the sense amplifier and is preferably a programmable parameter of pacemaker 10. The margin high and margin low comparators have additional threshold levels that are multiples of the basic intrinsic comparator threshold. The values of those multiples are preferably programmable parameters of pacemaker 10. The margin low threshold is always greater than the basic threshold, but less than the margin high threshold. The margin comparators determine the degree to which an incoming signal exceeds basic thresholds. The evoked response comparator determines when an evoked response signal has been detected, and has a threshold level that is preferably independently programmable.

The outputs of the comparators are routed to detection logic (DETLOGIC) 70 circuit for final screening of the logical outputs from DAC 68. DETLOGIC circuit 70 is subdivided into two sections that deal with the evoked response comparator output and the intrinsic comparator output. The first operation DETLOGIC circuit 70 performs on the intrinsic response signal is to determine that the signal persists for a minimum duration of 1 millisecond. A 1 kHz clock signal is used to accomplish this processing. The occurrence of an intrinsic event of sufficient duration is indicated by the rising edge of an ISENSE signal. The ISENSE signal will remain high as long as the comparator is asserted. In a manner similar to that of intrinsic event detection provided by the present invention, DETLOGIC circuit 70 determines whether an evoked signal persists for at least 1 mS. Evoked response indications may be detected only during the Capture Detect Window (CDW). The CDW is a window that follows the delivery of a pacing pulse or stimulus, and that is generated by stimulation and control circuitry 22.

As noted above, in one embodiment of the present invention after-potential rejection of sensed signals is achieved by negative peak-tracking the sensed signal. In this embodiment of the present invention, an assumption is made that the after-potential signal appears as a negative, substantially exponentially decaying artifact between the pacing electrode and the indifferent electrode. Thus, according to this embodiment of the present invention, any change in polarity of the sensed signal may be attributed to the presence of an evoked response signal.

Figure 7A:
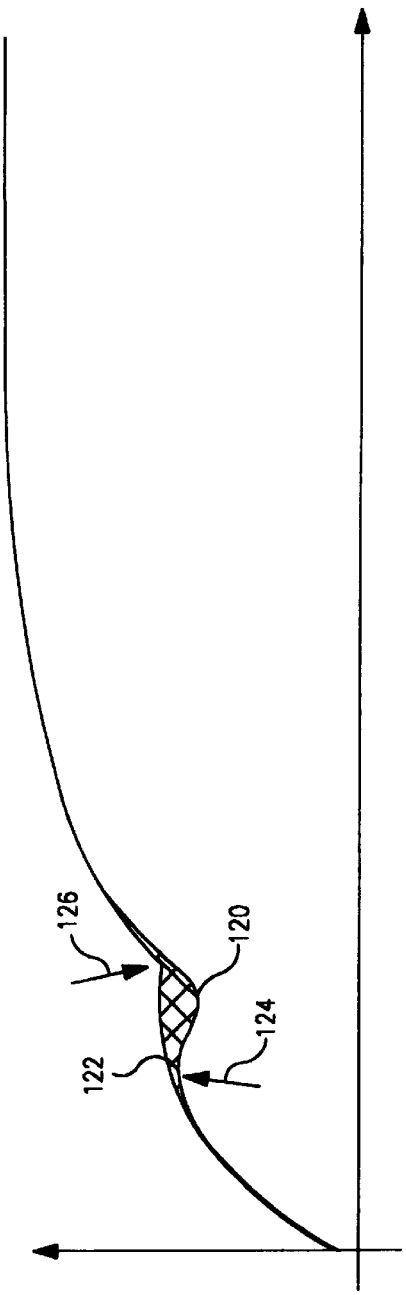
FIGS. 7(a) and 7(b) show, respectively, waveforms representing the input to, and output from, the sense amplifier circuitry of FIGS. 5(a), 5(b), 6(a) and 6(b)
Figure 7B:
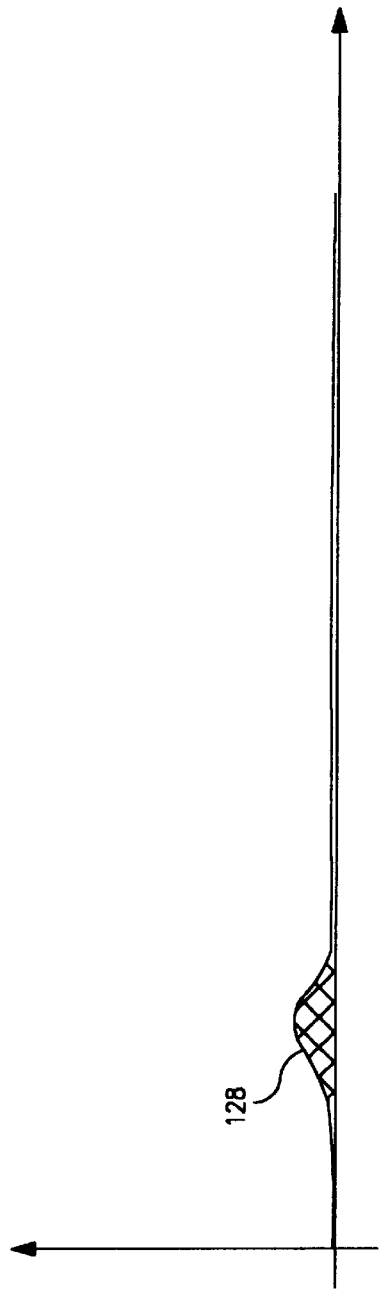

In FIG. 7(a), lower waveform 120 represent the output of DIFFAMP circuit 58, while upper waveform 122 represents a "peak-tracked" version of waveform 120. That is, waveform 122 tracks waveform 120 in one direction only. When waveform 120 begins to change direction (i.e., when the polarity of the rate of change of waveform 120 begins to change), waveform 122 no longer tracks waveform 120. A change in direction of waveform 120 is indicated by arrow 124 in FIG. 7(a). Waveform 122 begins tracking waveform 120 again at the point identified by arrow 126, but only when waveform 120 once again exceeds its previous peak value (denoted by arrow 124). FIG. 7(b) shows waveform 128, or the signal resulting when waveform 120 is subtracted from waveform 122. In other words, waveform 128 results from the subtraction of the output signal provided by DIFFAMP circuit 58 from the peak-tracked signal. Waveform 128 is the signal that appears at SO node 116 in FIG. 5(a).

Figure 8:
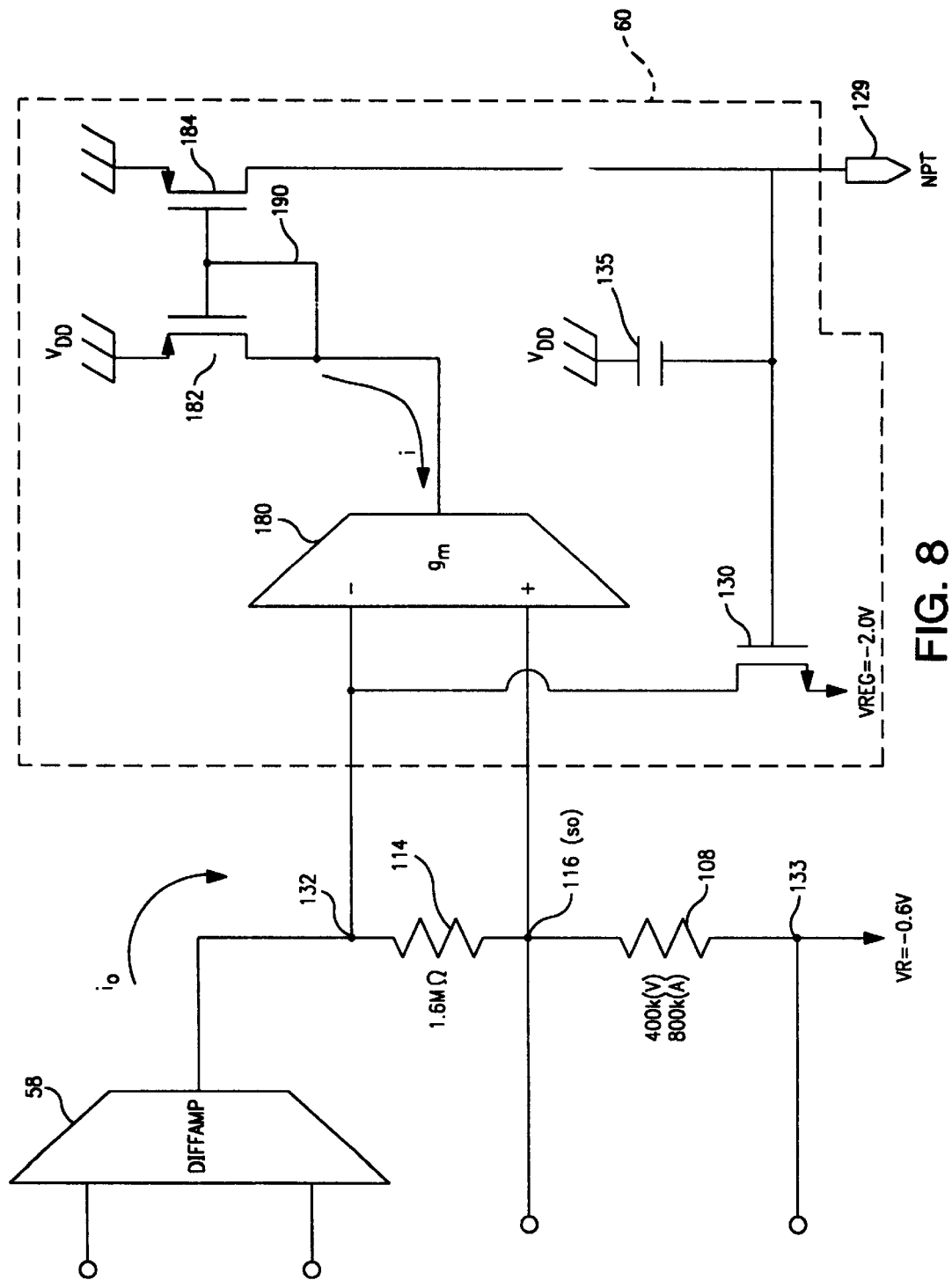
FIG. 8 shows a schematic functional block diagram of one embodiment of a capture detection circuit of the present invention.

FIG. 8 shows a more detailed functional block diagram of negative peak-tracking CDC 60. FIG. 8 shows that CDC 60 may include transconductance differential amplifier 180 and two transistors 182 and 184 that function as a diode between amplifier 180 and $V_{DD}$. As previously noted, CDC 60 monitors the output from DIFFAMP 58 through resistor 114. Like a ratchet that engages in one direction only, the voltage at node VNPT 129 can only increase towards $V_{DD}$, and thus only turn on N-channel transistor 130 to a greater extent. As transistor 130 turns on more fully, more current originating at node 132 from the output of DIFFAMP 58 flows through transistor 130. Thus, only current excursions less than the most recent peak-tracked current are passed to resistor 108. That is, CDC 60 is essentially a feedback loop that attempts to zero the current flowing through resistor 114, and that may only increase the current being subtracted from node 132. Capacitor 135 facilitates this one-way or "ratcheting" effect by preventing the voltage applied to the gate of transistor 130 from falling when the sensed signal (i.e., the output of DIFFAMP 58) increases.

Figure 9A:
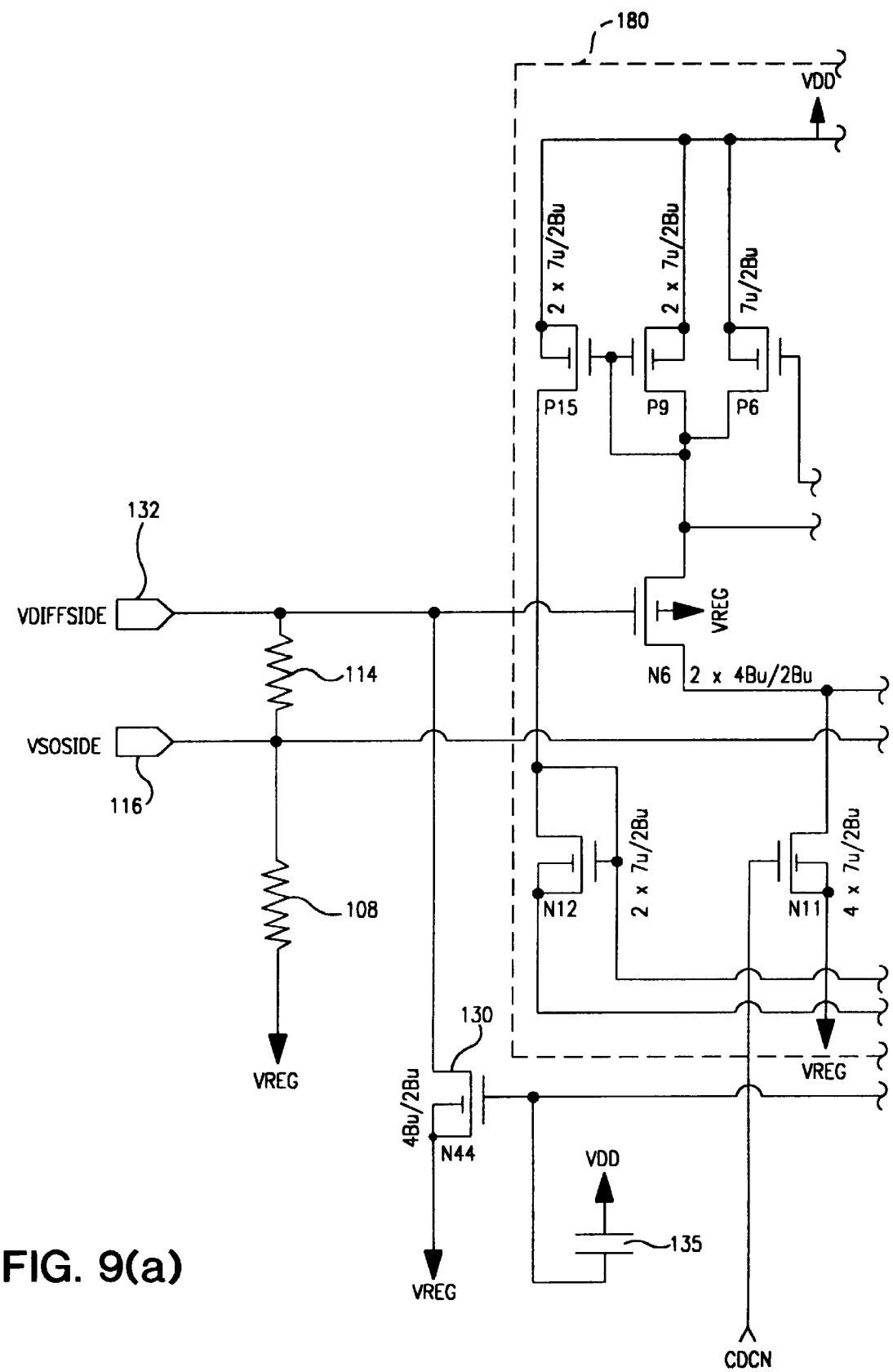
FIG. 9 shows a more detailed circuit diagram of the capture detection circuit shown in FIG. 8.
Figure 9B:
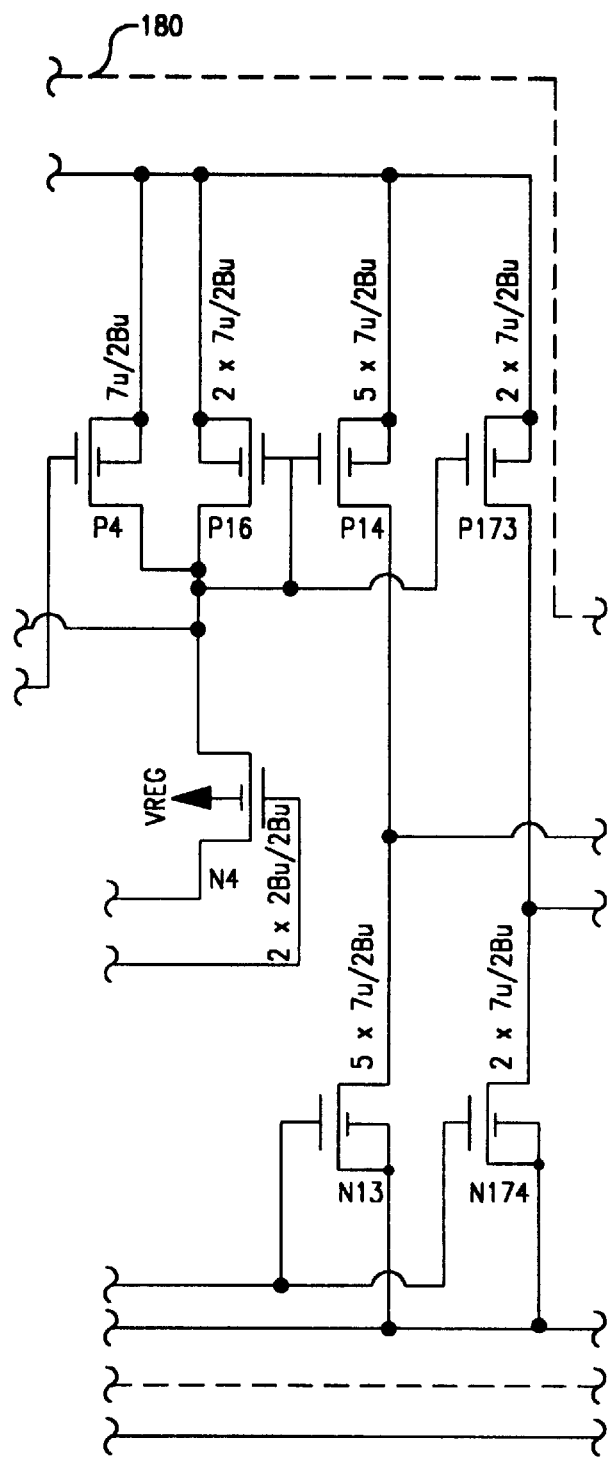
Figure 9C:
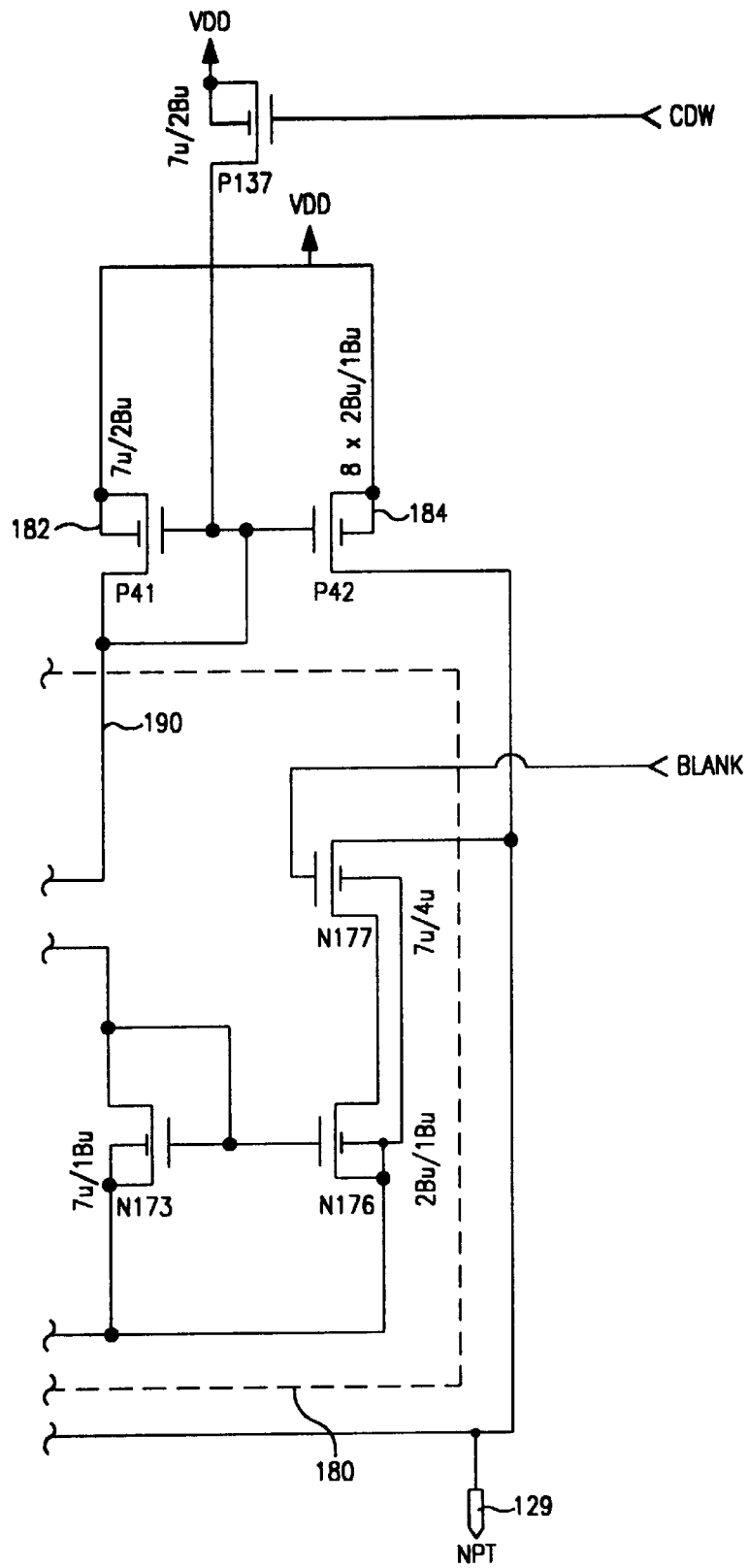

FIG. 9 shows a more detailed schematic circuit diagram of one preferred embodiment of the CDC 60 of the present invention. As in FIG. 8, differential amplifier 58 or DIFFAMP 58 (not shown in FIG. 9) is coupled to CDC 60 at node 132. Sixteen hundred kilo-ohm resistor 114 couples nodes 132 and 116. Four hundred kilo-ohm or 800 kΩ pull-up resistor 108 (corresponding to the ventricular and atrial channels, respectively) is disposed between node 116 and a −0.6 V regulated voltage source. FIG. 9 shows several inputs CDW, CDCN and BLANK not shown in FIG. 7. Inputs CDW (Capture Detect Window) and CDCN (Capture Detect Control) activate CDC 60 when capture detection is desired. Input BLANK is for blanking CDC 60 during pacing, for example.

In respect of a low polarization lead positioned in the ventricle, the embodiments of the present invention described heretofore do not significantly filter the evoked response, and thus result in an acceptable signal-to-noise ratio (SNR) being obtained in the case of evoked response signal detection. For larger pacing energies, high polarization leads, or atrial evoked response detection, a greater SNR may be desirable. This is because in these (and perhaps other) situations, the after-potential artifact may dominate the pacing electrode voltage to such an extent that no positive deflections occur in the sensed signal.

To solve this problem, the capture detection circuitry of one embodiment of the present invention may include additional peak tracking circuitry for peak tracking the-diode current in CDC 60 itself. This additional circuitry is referred to herein as "second order" peak tracking circuitry. This circuitry adds current to node 116 if the tracking current increases. In other words, when the current flowing through transistor 182 on line 190 in FIG. 8 increases, more current is provided at node 116. The increase reflects an "acceleration" or increasing magnitude of the derivative (dv/dt) of the output signal provided by DIFFAMP 58. The "acceleration" occurs when the post-pace after-potential signal dominates the evoked response signal to such an extent that no reversal of polarity in the sensed signal occurs. By detecting acceleration, or an increase in the magnitude of dv/dt, in the sensed signal, it has been discovered that the evoked response may be faithfully detected.

Figure 10:
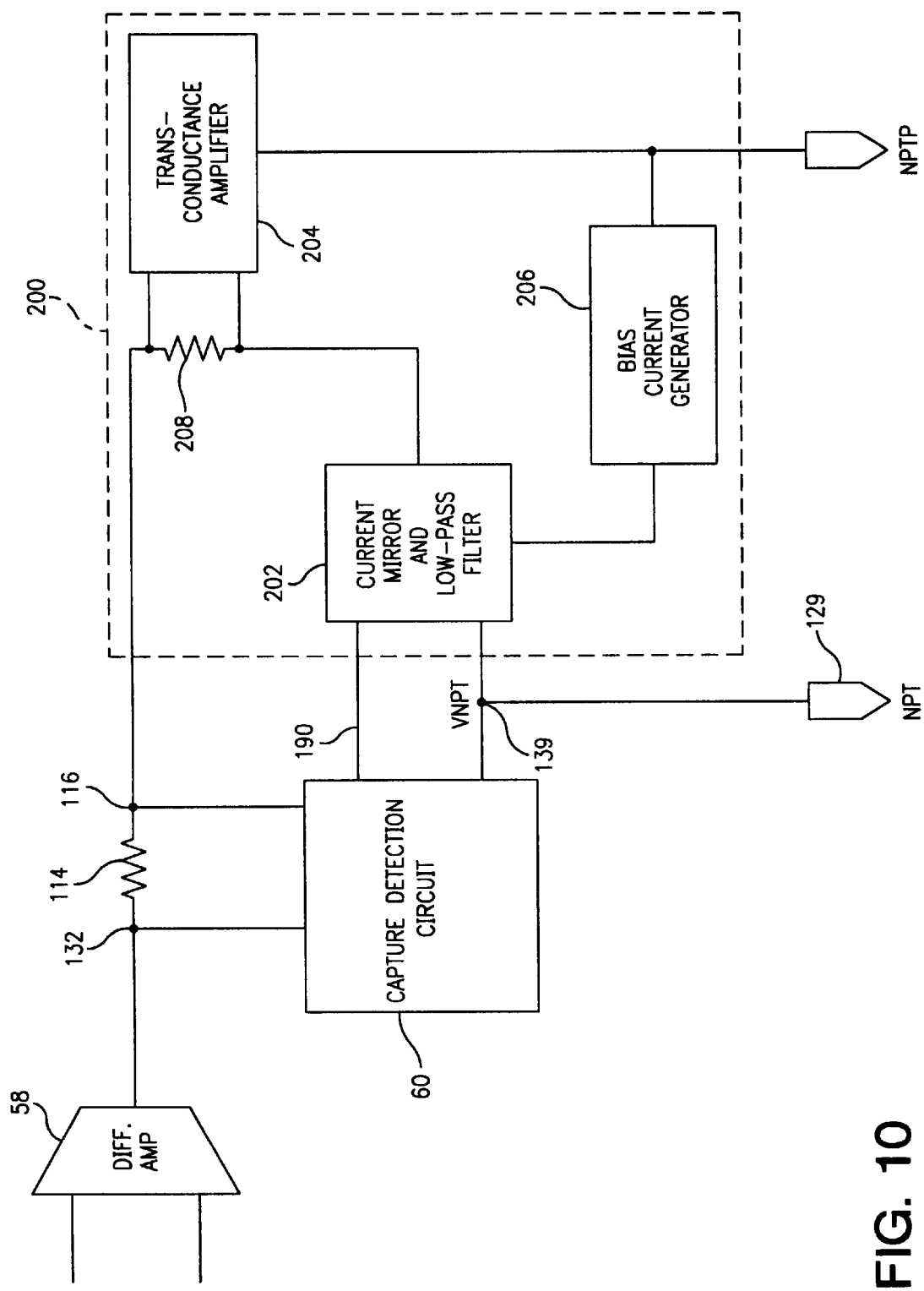
FIG. 10 shows a schematic functional block diagram of another embodiment of the capture detection circuit of the present invention.

FIG. 10 shows a block diagram of a negative peak tracking detector circuit in accordance with an embodiment of the invention. The circuit includes not only CDC 60 previously described, but also a second-order negative peak tracking circuit 200. As shown in FIG. 10, second order peak tracking circuit 200 comprises three main components: a current mirror and low-pass filter circuit 202; a transconductance amplifier 204, and a bias current generator 206. Current mirror and low-pass filter circuit 202 receives a tracking current signal from CDC 60 on line 190, and also receives the NPT output signal VNPT from CDC 60. Current mirror and low-pass filter circuit 202 low-pass filters the tracking current on line 190 from CDC 60 and mirrors that current through 1.6 MΩ resistor 208. The current flowing through resistor 208 is monitored by transconductance amplifier 204. If the tracking current from CDC 60 rises, amplifier 204 adds current to node 116.

Figure 11A:
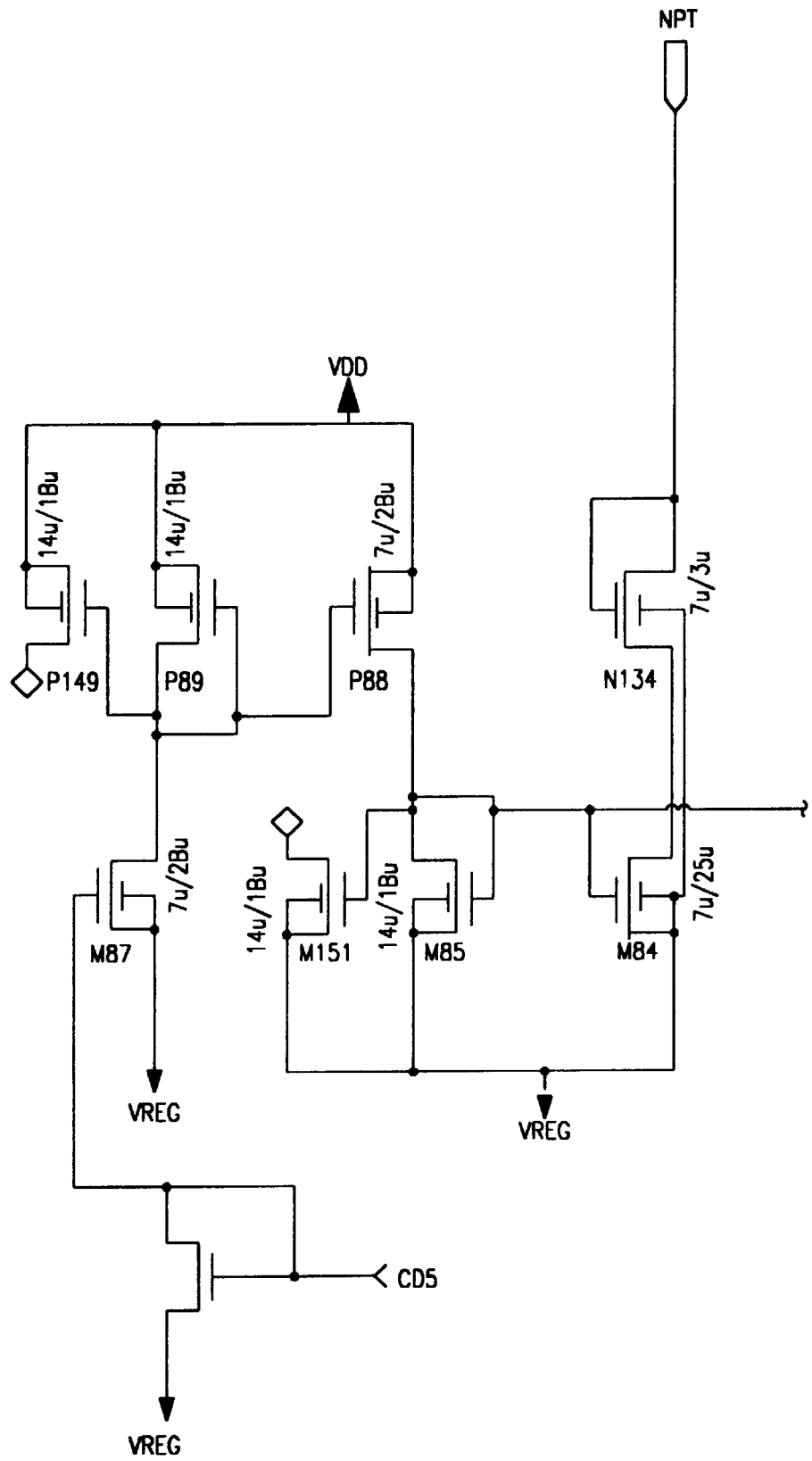
FIG. 11 shows a more detailed circuit diagram of a portion of the capture detection circuitry of FIG. 10.
Figure 11B:
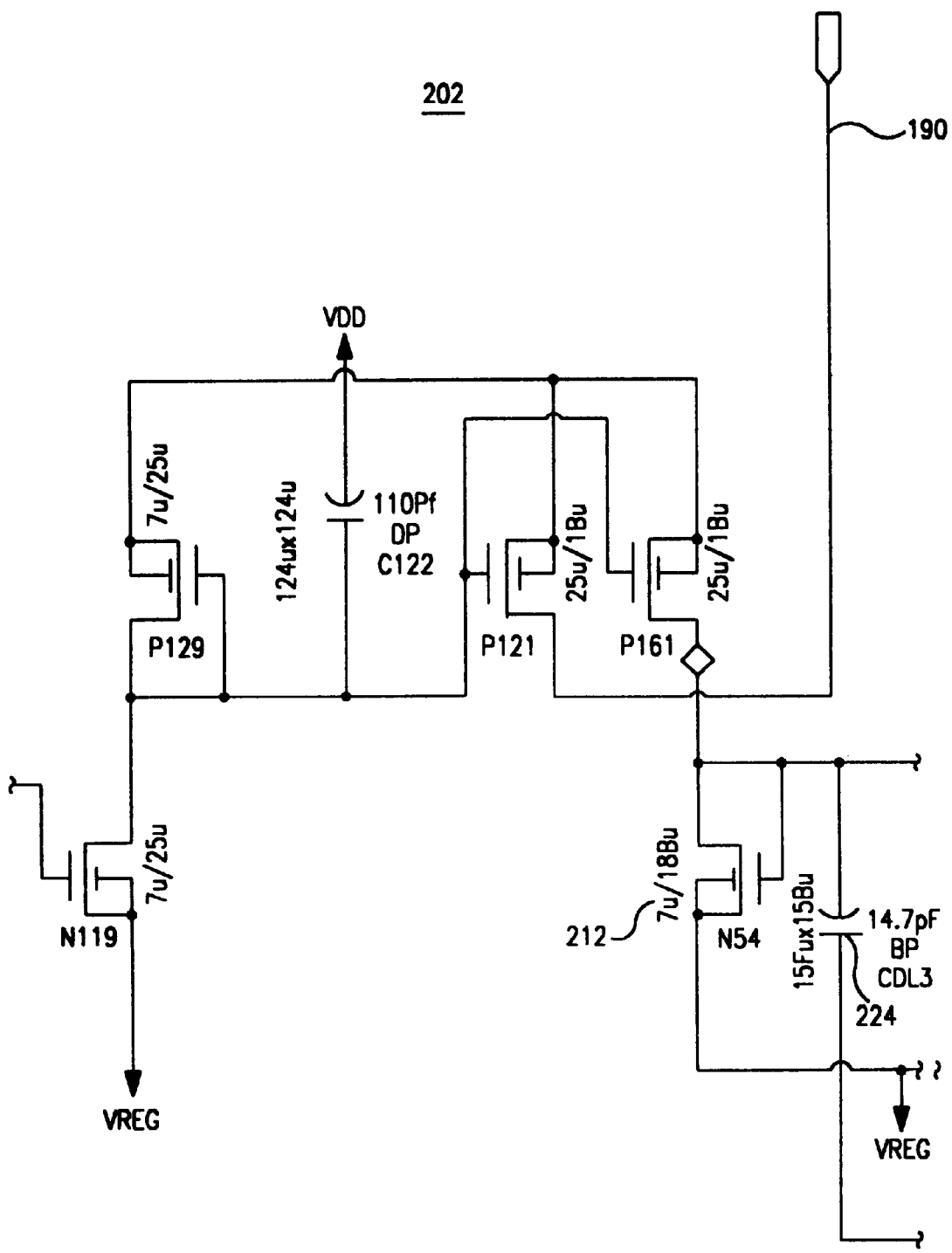
Figure 11C:
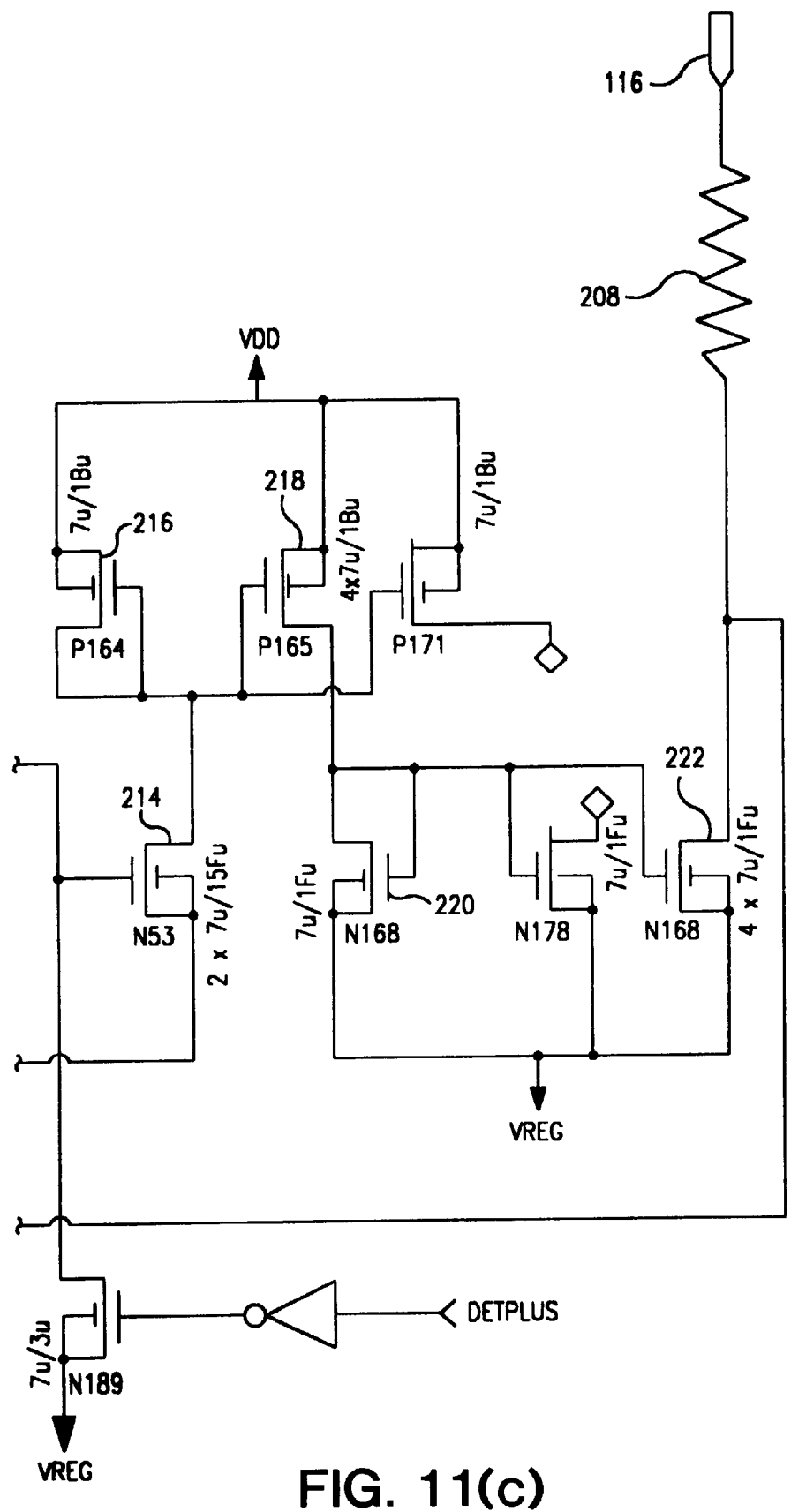
Figure 12A:
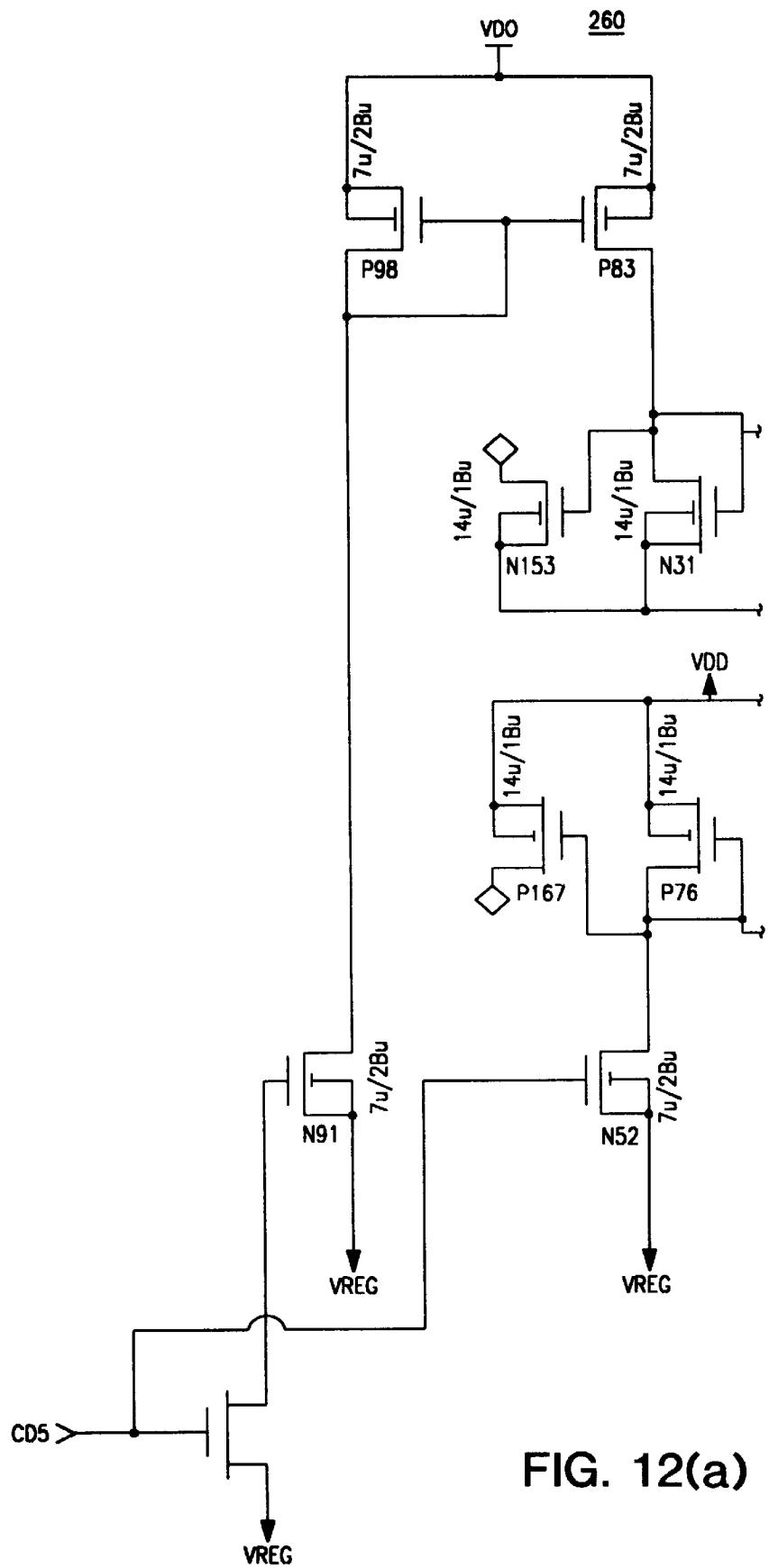
FIG. 12 shows a more detailed circuit diagram of another portion of the capture detection circuitry of FIG. 10.
Figure 12B:
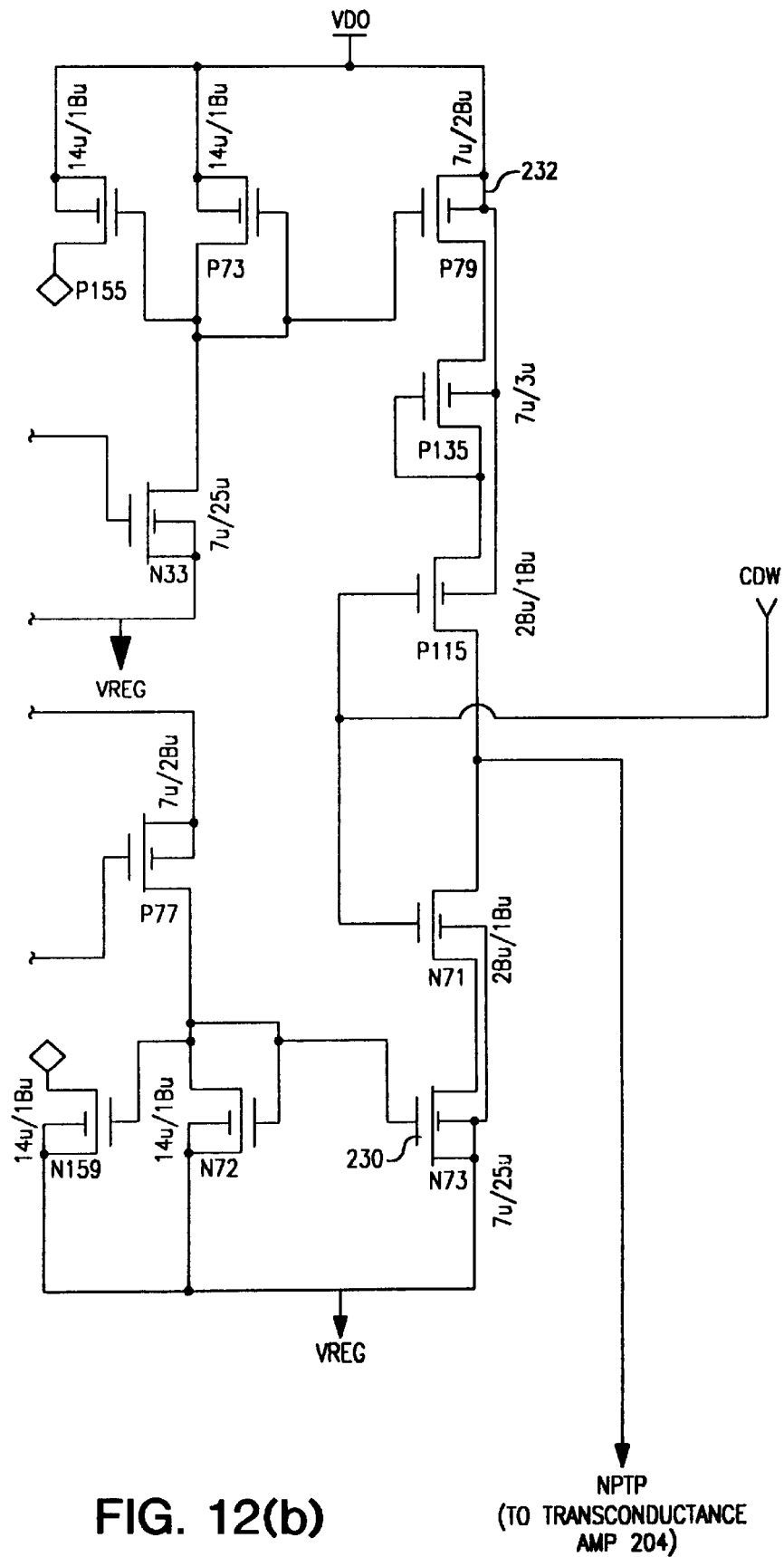
Figure 13A:
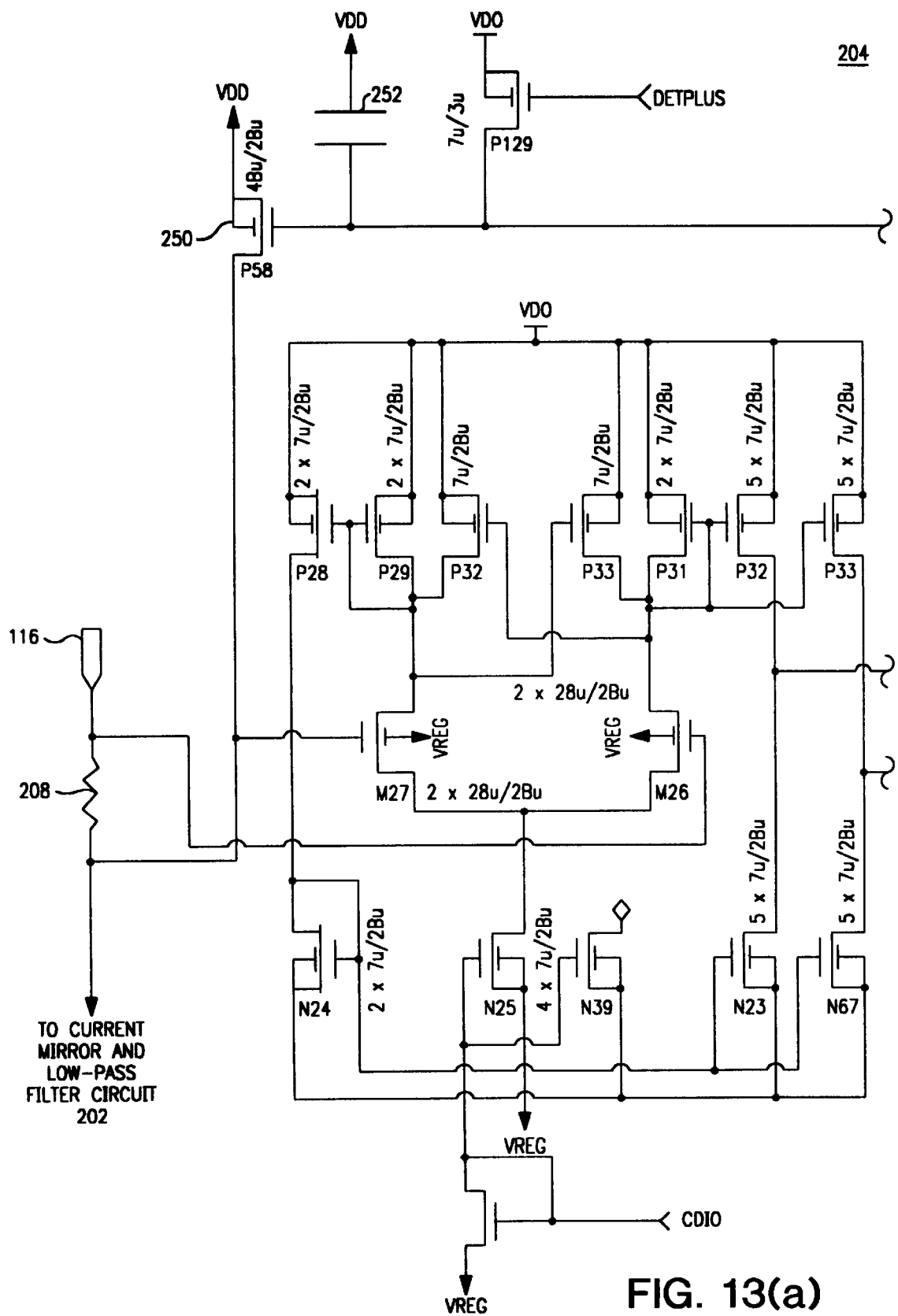
FIG. 13 shows a more detailed circuit diagram of another portion of the capture detection circuitry of FIG. 10.
Figure 13B:
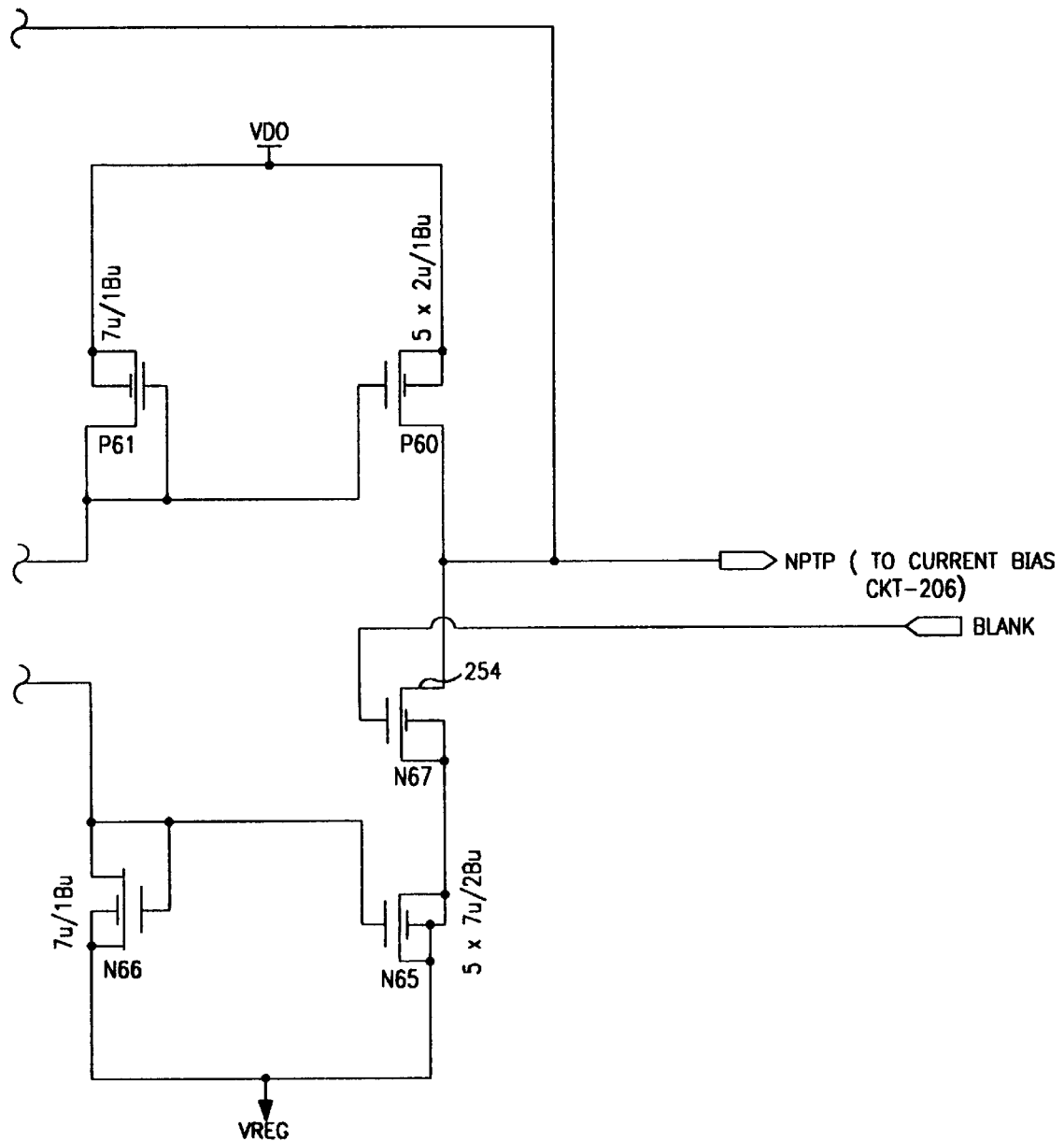

More detailed schematic diagrams of the circuitry comprising second-order tracking circuit 200 in accordance with one embodiment of the invention are shown in FIGS. 11, 12, and 13. FIG. 11 is a schematic diagram of current mirror and low pass filter circuit 202. Current mirroring of the tracking current provided by CDC 60 on line 190 is performed by transistors 212, 214, 216, 218, 220 and 222. The current mirror circuit includes a low pass filter comprising capacitor 224 and the transconductance of transistor 212. The gain of the mirror circuit shown in FIG. 10 is about 32.

FIG. 12 is a schematic diagram of bias current generator 206 shown in FIG. 9. In circuit 206, and during the capture detect window, a weak current (about 60 pA) is generated by transistor 230 to cause a slow increase in the second-order negative peak tracking current. The capture detect window is defined by control circuitry for device 10, and generates signal CDW for application to bias current generator 206. In circuit 206, and after the capture detect window, another weak current is generated by transistor 232 to cause a slow decrease in tracking current. In circuit 206, input signal CD5 represents the current being provided to node VNPTP.

FIG. 13 is a schematic diagram of transconductance amplifier 204 shown in FIG. 10. Transconductance amplifier 204 is substantially similar to transconductance amplifier 180 in the aforementioned first-order negative peak tracking circuit CDC 60, and performs a substantially similar function. That is, amplifier 204 samples or monitors the current flowing through resistor 208 and the feedback current at node 116 to detect any increase in the sensed signal; which is expected to be continuously decreasing. The "ratcheting" effect of the second order negative-peak tracking circuit is caused by transconductance amplifier 204 injecting current into node 116 through P-channel transistor 250 and resistor 208 when an increase in the sensed signal occurs. Capacitor 252, like capacitor 135 in CDC 60, facilitates this "ratcheting" effect by preventing the voltage applied to the gate of transistor 250 from falling when the sensed signal increases; n-channel transistor 254 aids and participates in the aforementioned ratcheting effect.

Figure 14A:
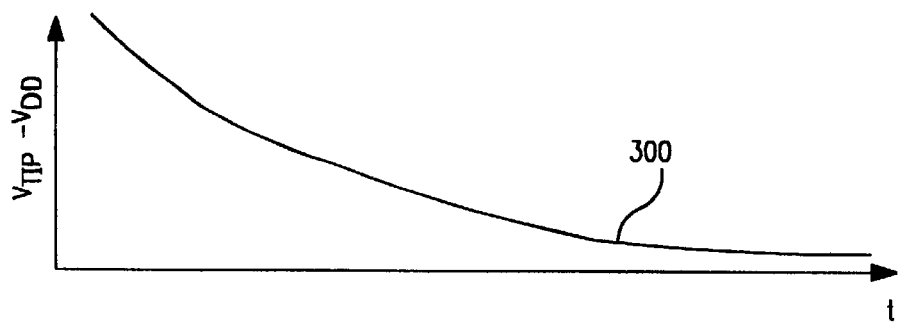
FIGS. 14(a)–14(c) show waveforms corresponding to the signals appearing at various nodes of the capture detection circuitry shown in FIG. 10 after a pacing stimulus is delivered which does not evoke a cardiac response.
Figure 14B:
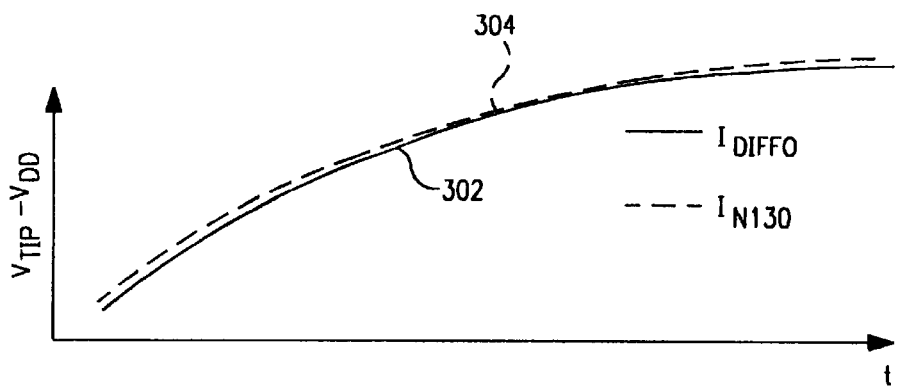
Figure 14C:
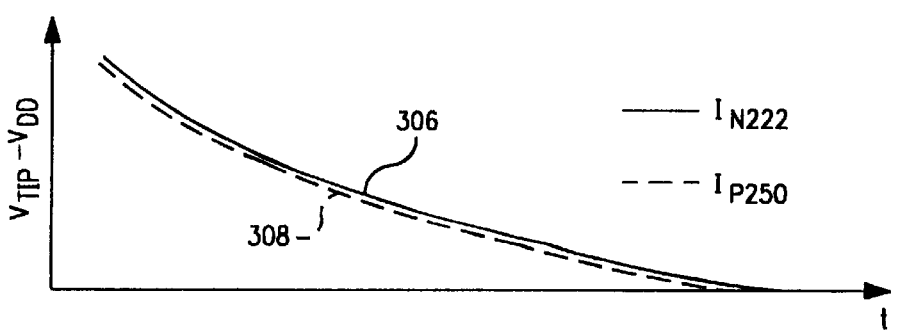

FIGS. 14(a), 14(b), 14(c), 15(a), 15(b), 15(c), 16(a), 16(b) and 16(c) illustrate the operation of negative peak tracking circuit 60 and second-order negative peak tracking circuit 200 according to one embodiment of the present invention. FIG. 14(a) shows the waveform of a signal sensed by tip electrode 18 of lead 14. Waveform 300 represents the intracardic signal appearing between tip electrode 18 and the indifferent electrode during the period of time immediately following delivery of a pacing stimulus. FIGS. 14(a) through 14(c) represent the case where no evoked response signal is generated in response to a pacing stimulus. Thus, FIG. 14(a) shows the tip-to-tissue polarization artifact signal that typically follows a pacing stimulus that does not cause an evoked response. As described above, such an artifact signal is an exponentially decaying signal that exhibits no positive-slope excursions.

The signals shown in FIG. 14(b) correspond to the signals shown in FIG. 14(a). Waveform 302 represents the output current of differential amplifier 58, or the current flowing through resistor 114 that is monitored by CDC 60 when determining the amount of feedback current to be delivered. Waveform 304, represented by a dashed line in FIG. 14(b), represents the current flowing through transistor 130 in CDC 60; that current is the feedback current provided to node 132 in CDC 60. Note that waveforms 302 and 304 in FIGS. 14(b) and 14(c) are inverted in respect of waveform 300 in FIG. 14(a). Signals or waveforms 302 and 304 are inverted by the operation of DIFFAMP 58.

FIG. 14(c) shows waveforms 306 and 308. Waveform 306 represents the current flowing through transistor 222; that current is monitored by second-order negative peak tracking circuit 200 to determine the amount of feedback current to be provided. Waveform 308, shown as a dashed line in FIG. 14(c), represents the current flowing through transistor 250; that current is the feedback current provided to node 116 in response to detected increases in—or "acceleration" of—the output of DIFFAMP 58.

Figure 15A:
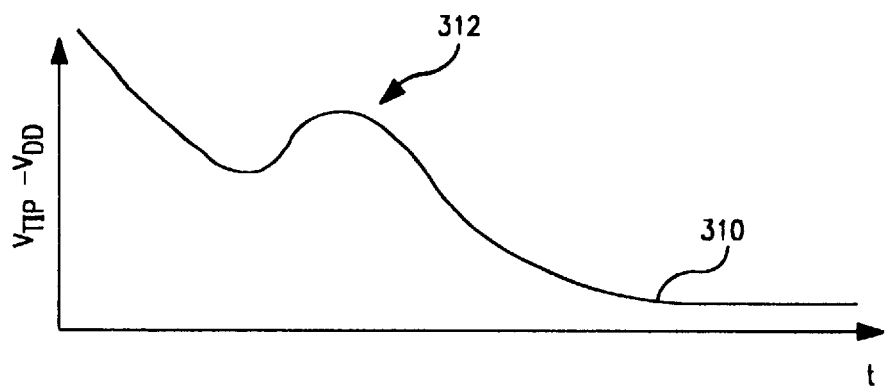
FIGS. 15(a)–15(c) show waveforms corresponding to the signals appearing at various nodes of the capture detection circuitry of FIG. 10 after a pacing stimulus is delivered which does evoke a cardiac response.
Figure 15B:
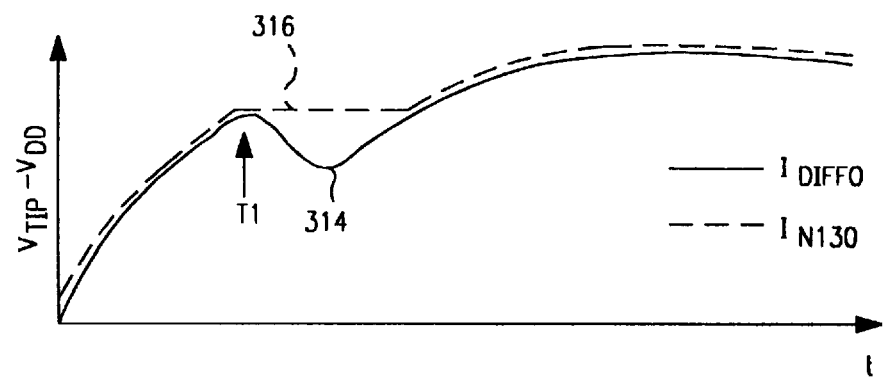
Figure 15C:
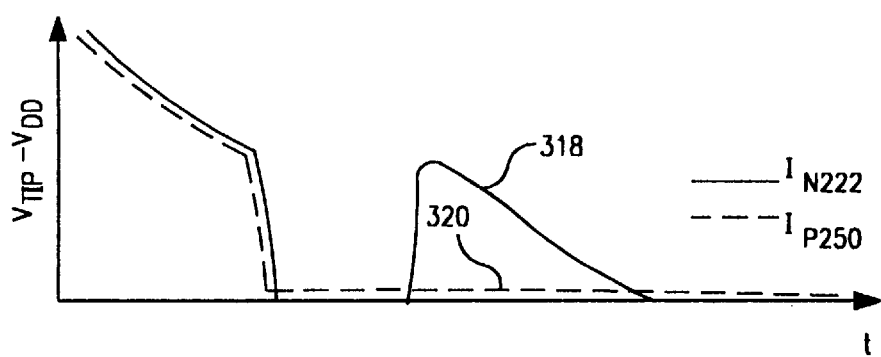

FIGS. 15(a) through 15(c) show waveforms resulting from a prominent evoked response to a pacing stimulus, where those waveforms are otherwise similar to the waveforms illustrated in FIGS. 14(a) through 14(c). First-order CDC 60 is well-suited for detecting evoked responses like those illustrated in FIG. 15(a). Waveform 310 in FIG. 15(a) represents the sensed signal appearing across tip electrode 18 of lead 14 and the indifferent electrode for the period of time immediately following the delivery of a pacing stimulus. The prominent increase or rise in the sensed signal designated generally by reference numeral 312 in FIG. 15(a) represents the evoked response signal.

Like waveform 302 in FIG. 14(b), waveform 314 in FIG. 15(b) represents the output current provided by DIFFAMP 58 (or the current monitored by CDC 60). Like waveform 304 in FIG. 14(b), waveform 316 represents the current flowing through transistor 130 in CDC 60. Time T1 in FIG. 15(b) indicates the onset of an evoked response signal. Despite a decrease in the magnitude or change in polarity of waveform 314 that occurs generally at time T1, the current flowing through transistor 130 does not decrease. This is due to the operation of hold-up capacitor 135 in circuit 60.

In FIG. 15(c), waveform 318 represents the current flowing through transistor 222 in second-order negative peak tracking circuit 200 (or the current that flows through resistor 208 and that is monitored by circuit 200). Waveform 320 denoted by dashed lines represents the current flowing through transistor 250 (or the feedback current provided by circuit 200. FIGS. 15(a) through 15(c) illustrate the concept that first-order CDC 60 is dominant in detecting evoked responses when evoked response signals are large.

Figure 16A:
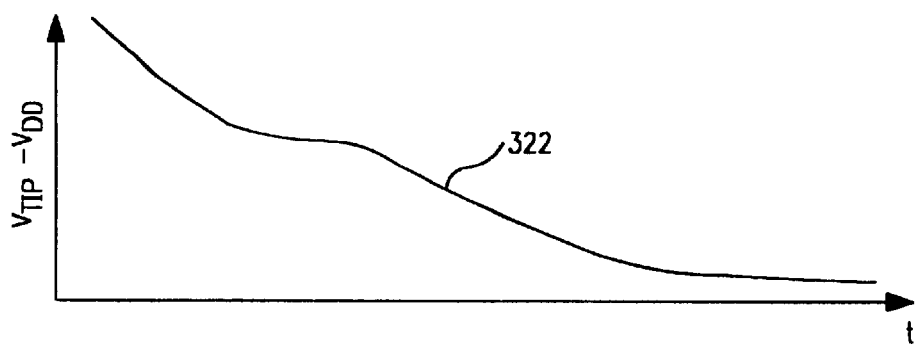
FIGS. 16(a)–16(c) show waveforms corresponding to the signals appearing at various nodes of the capture detection circuitry of FIG. 10 after a pacing stimulus is delivered which evokes a cardiac response weaker than that shown in FIGS. 15(a)–15(c)
Figure 16B:
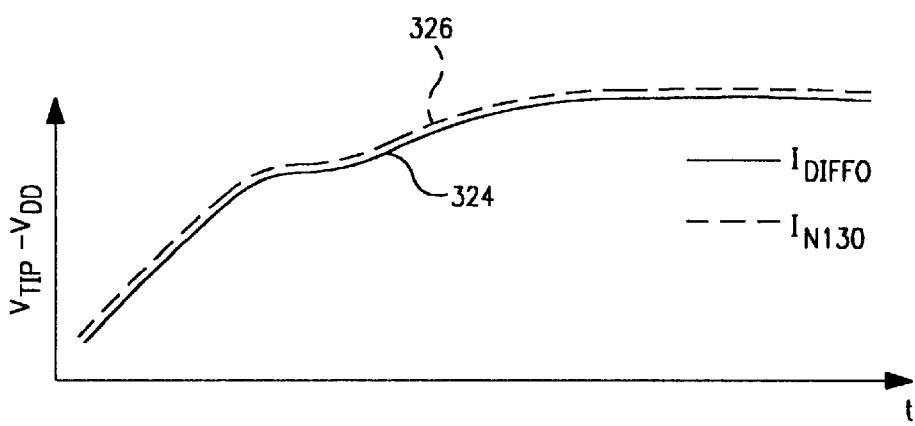
Figure 16C:
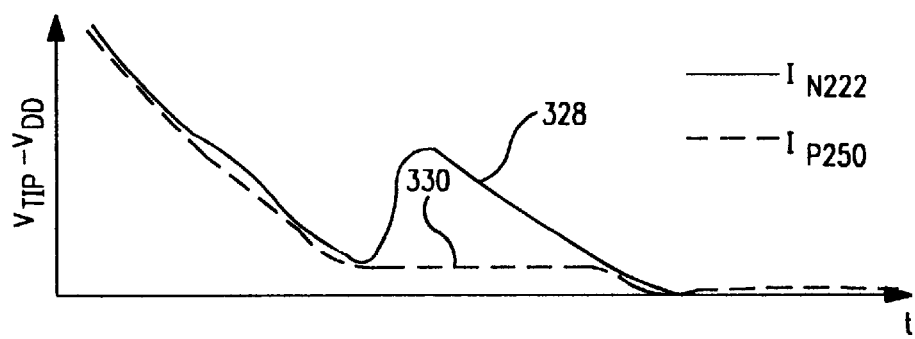

When less prominent evoked response signals must be detected, however, second-order negative peak tracking circuit 200 must be depended upon for evoked response signal detection. FIGS. 16(a) through 16(c) show waveforms illustrating the circumstance where an evoked response signal is not prominent. Waveform 322 in FIG. 16(a) represents the sensed signal appearing between tip electrode 18 and the indifferent electrode when the evoked response signal is weak. FIG. 16(b) corresponds to FIGS. 14(b) and 15(b), and shows that first-order CDC 60 may not be capable of detecting the weak evoked response signal that is superimposed upon the large, dominant after-potential decaying signal.

FIG. 16(b) shows that the output provided by DIFFAMP 58 (waveform 324) and the current through transistor 130 in CDC 60 do not reflect evoked response detection. In FIG. 16(c), on the other hand, it may be seen that second-order negative peak tracking circuit 200 operates to negative peak track the current flowing through transistor 222 (as indicated by waveform 328). That is, the amount of current flowing through transistor 250 (indicated by waveform 330) does not increase as the amount of current flowing through transistor 222 increases. Thus, second-order negative peak tracking circuit 200 detects less prominent evoked response signals than may be detected by first order CDC 60.

Figure 17:
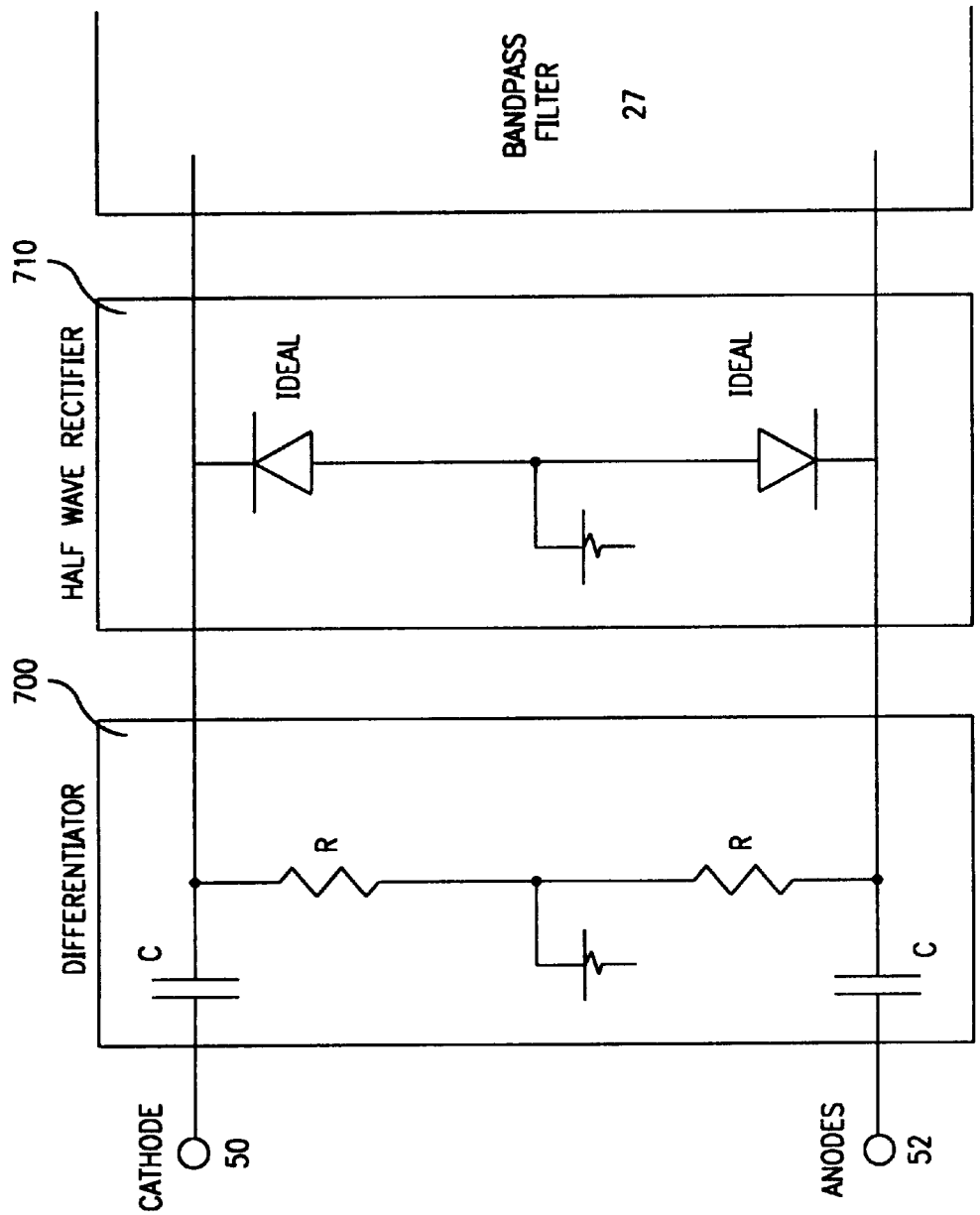
FIG. 17 shows a schematic functional block diagram constructed in accordance with another embodiment of the present invention.
Figure 18A:
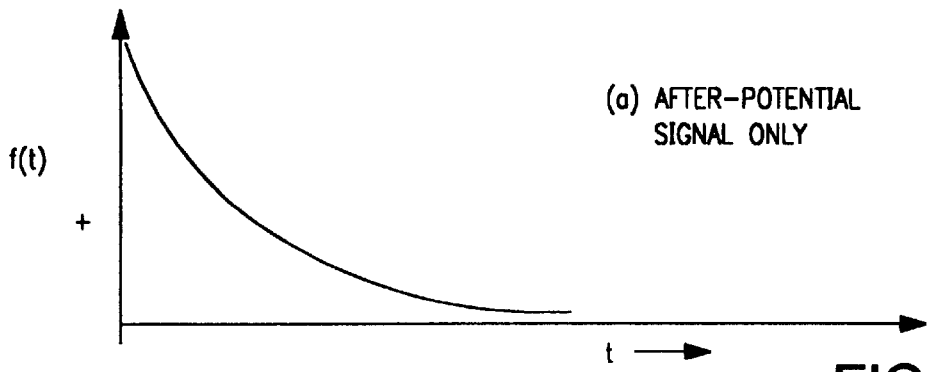
FIGS. 18(a) and 18(b) show waveforms corresponding to the signals appearing at the input and output of the circuit shown in FIG. 17 when the input signal is characterized in having steeply sloping portions.
Figure 18B:
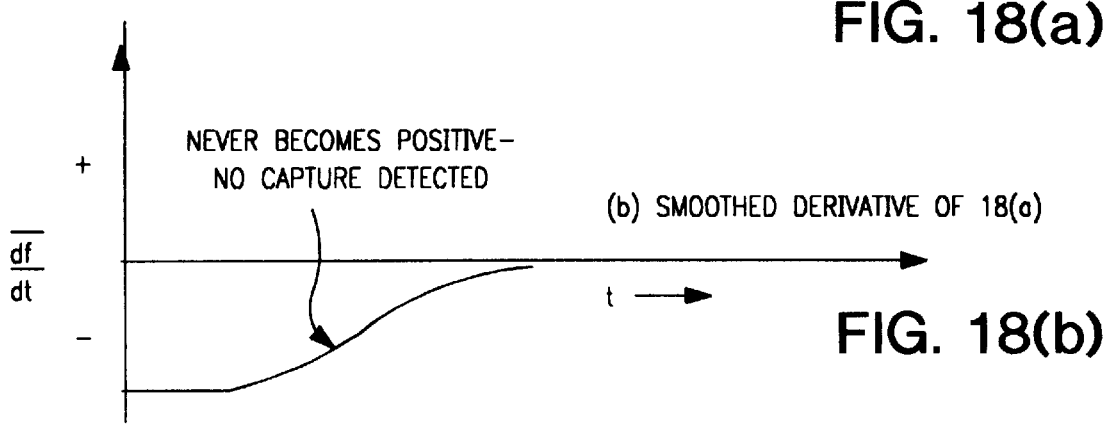
Figure 18C:
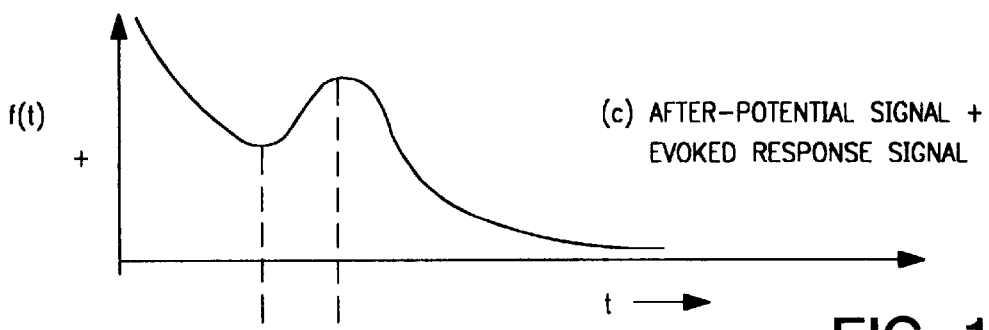
FIGS. 18(c) and 18(d) show waveforms corresponding to the signals appearing it the input and output of the circuit shown in FIG. 17 when the input signal is characterized in having portions less steeply sloping than those illustrated in FIG. 18(a)
Figure 18D:
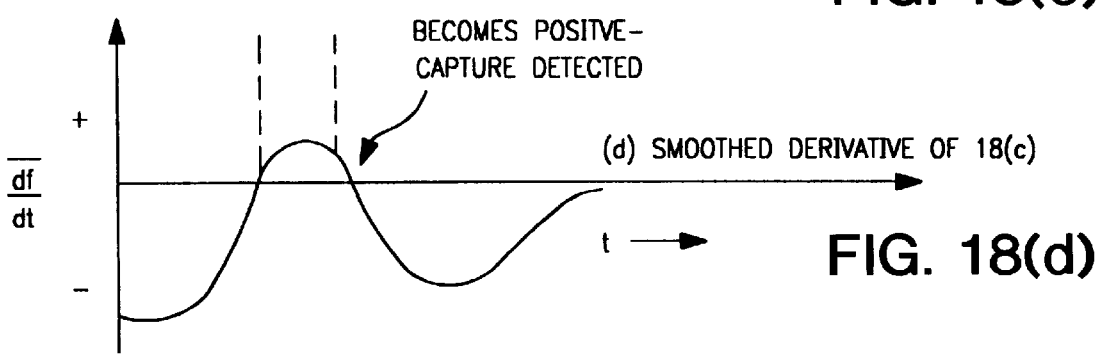

Another embodiment of the present invention is shown partially in FIG. 17, where substitute circuitry preceding the band-pass filter circuitry of FIGS. 4, 5(a) and 5(b) is shown. This embodiment of the invention may be considered a "smoothed derivative capture detection" circuit. In FIG. 17, the input signal is differentiated in differentiator block 700, and then half-wave rectified in half wave rectifier block 710. Differentiation of the input signals, followed by half-wave rectification, results in the ability to monitor the input signal for changes in signal polarity and "velocity" (or slew rate) during the period of time where capture detection is being performed. FIGS. 18(a) through 18(d) show the input and output signals obtained with the differentiation/rectification circuit of the present invention. Where there is no evoked response signal to be detected in the input signal, the differentiated and rectified output signal exhibits no positive-going excursions (see FIGS. 18(a) and 18(b)). Where there is an evoked response signal to be detected in the input signal, the differentiated and rectified output signal exhibits a positive-going excursion that will, in turn, be passed on to the sense amplifier circuit as a detected event (see FIGS. 18(c) and 18(d)).

In accordance with another embodiment of the present invention, the first-order differentiator block of FIG. 17 may be replaced with a second-order differentiator block that acts as a second order smoothed derivative capture detection circuit.

Figure 19:
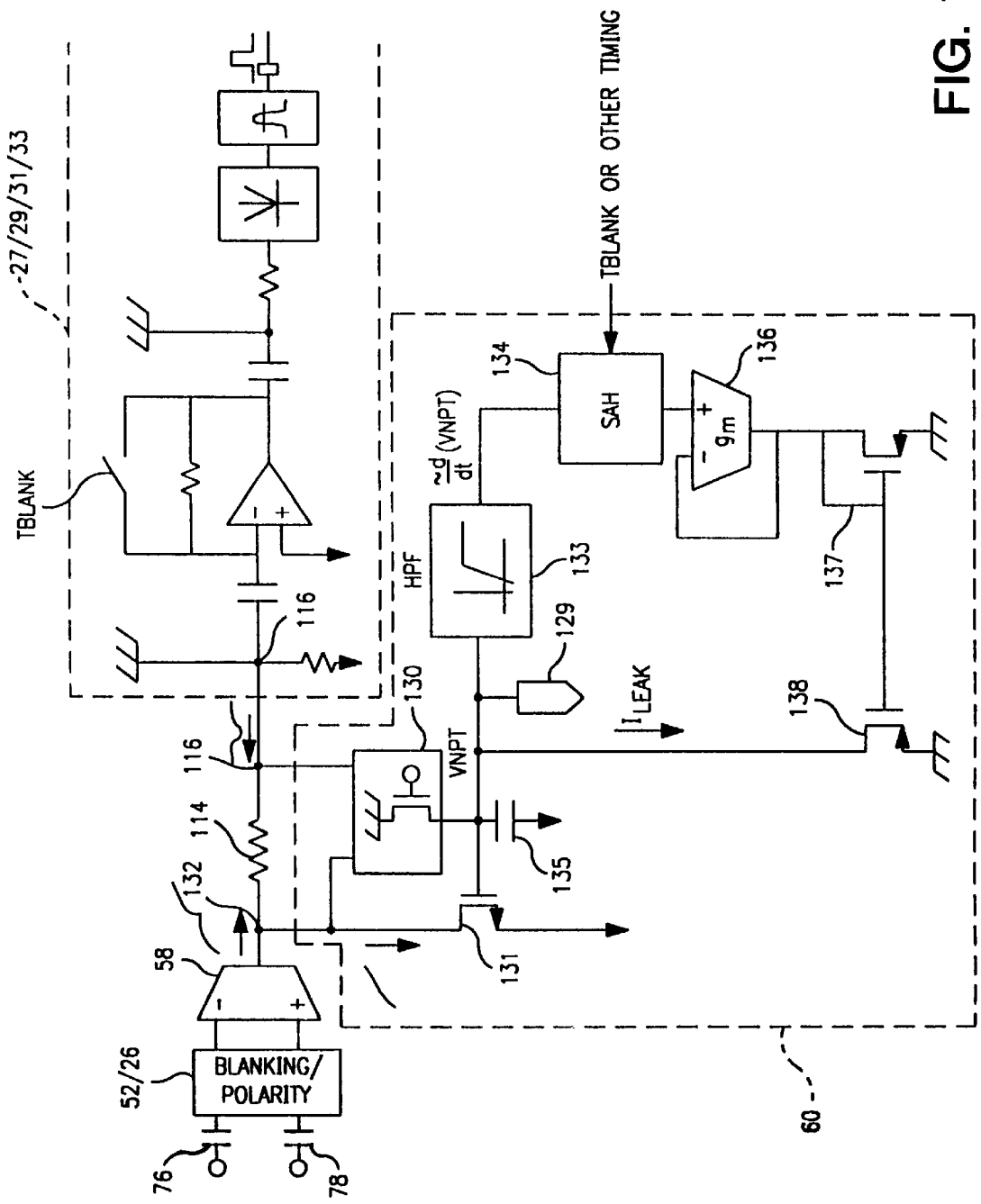
FIG. 19 shows a schematic functional block diagram constructed in accordance with another embodiment of the present invention.

FIG. 19 shows yet another embodiment of the present invention, where substitute circuitry preceding the band-pass filter circuitry of FIGS. 4, 5(a) and 5(b) is shown. This embodiment of the invention may be considered a "smart" or "modified" peak tracking circuit, where the slew rate of the sensed signal (dV(t)/dt), as opposed to the voltage itself (V(t)), may be tracked. Circuit 60 in FIG. 19 tracks the decay rate, or rate of change, of the sensed signal during the period of time immediately following the delivery of a pacing pulse or stimulus. Constant slew rate tracking of the sensed signal occurs at the gate of slew filtering transistor 131 at node 132. Slew filtering capacitor 135, $C_{NPT}$, smoothes the voltage signal present at node 139.

In the circuit of FIG. 19, the sensed signal is sampled immediately after the pacing pulse is delivered but before an evoked response signal may appear. High pass filter block or circuit 133 differentiates or substantially differentiates the sensed signal, and routes it to sample and hold (SAH) block or circuit 134. The sampled voltage output by sample and hold block 134 is fed into transconductance amplifier 136, which in turn produces an output current proportional to the input voltage. This output current is shown in FIG. 19 as $I_{leak}$. When the slew rate of the sensed signal is large, $I_{leak}$ is correspondingly large. When the slew rate of the sensed signal is small, $I_{leak}$ is correspondingly small.

Figure 20A:
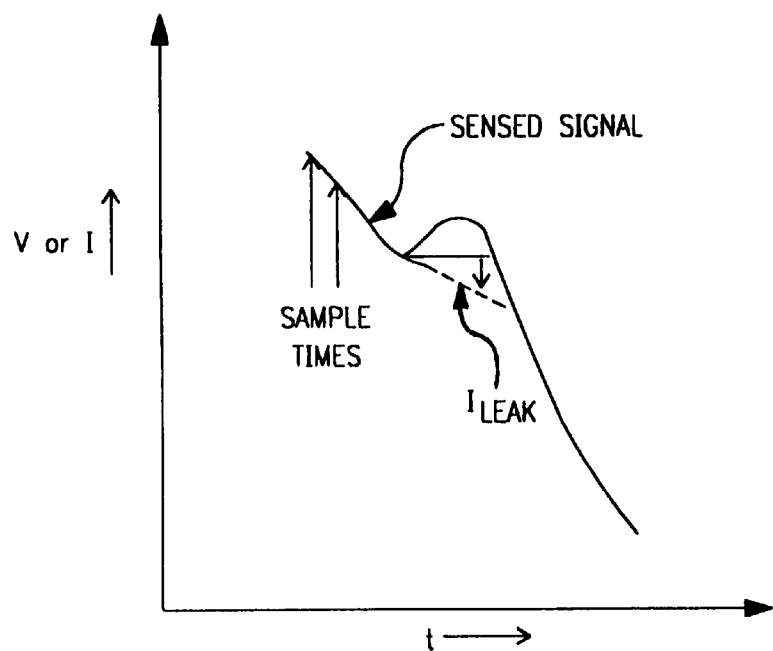
FIG. 20(a) and 20(b) show representative waveforms corresponding to the signals appearing at the input and output of the circuit shown in FIG. 19.
Figure 20B:
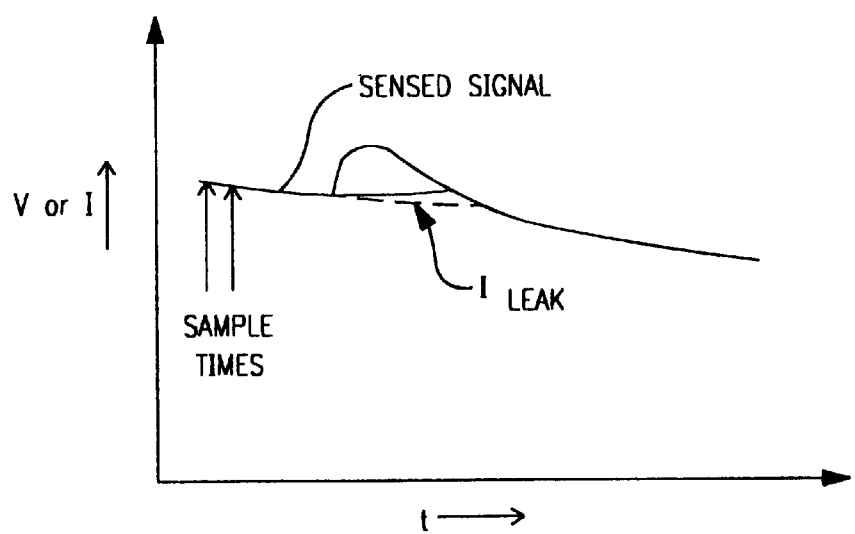

FIGS. 20(a) and 20(b) show how the circuit of FIG. 19 operates when the slew rate of the sensed signal is large (FIG. 20(a)) and small (FIG. 20(b)). The dashed lines in FIGS. 20(a) and 20(b) denote the leakage current, or $I_{leak}$, measured across $C_{NPT}$ 135 of FIG. 19. This leakage current may be seen to be a function of the degree of polarization of the tissue surrounding the electrode, and thus may provide a more accurate means of tracking the sensed signal.

Some embodiments of the circuit of the present invention are compatible with and may be easily inserted in existing circuitry for most THERA®-brand pacemakers manufactured by MEDTRONIC®, INC. For example, THERA Pacemaker Model Nos. 7944, 7945, 7946, 8940, 8941 and 8942 (as further described in the "THERA D Product Information Manual" and the "THERA SR Product Information Manual," both of which manuals are hereby incorporated by reference herein in their respective entireties), have circuitry that may be modified rather easily to include the present invention therein.

Figure 21:
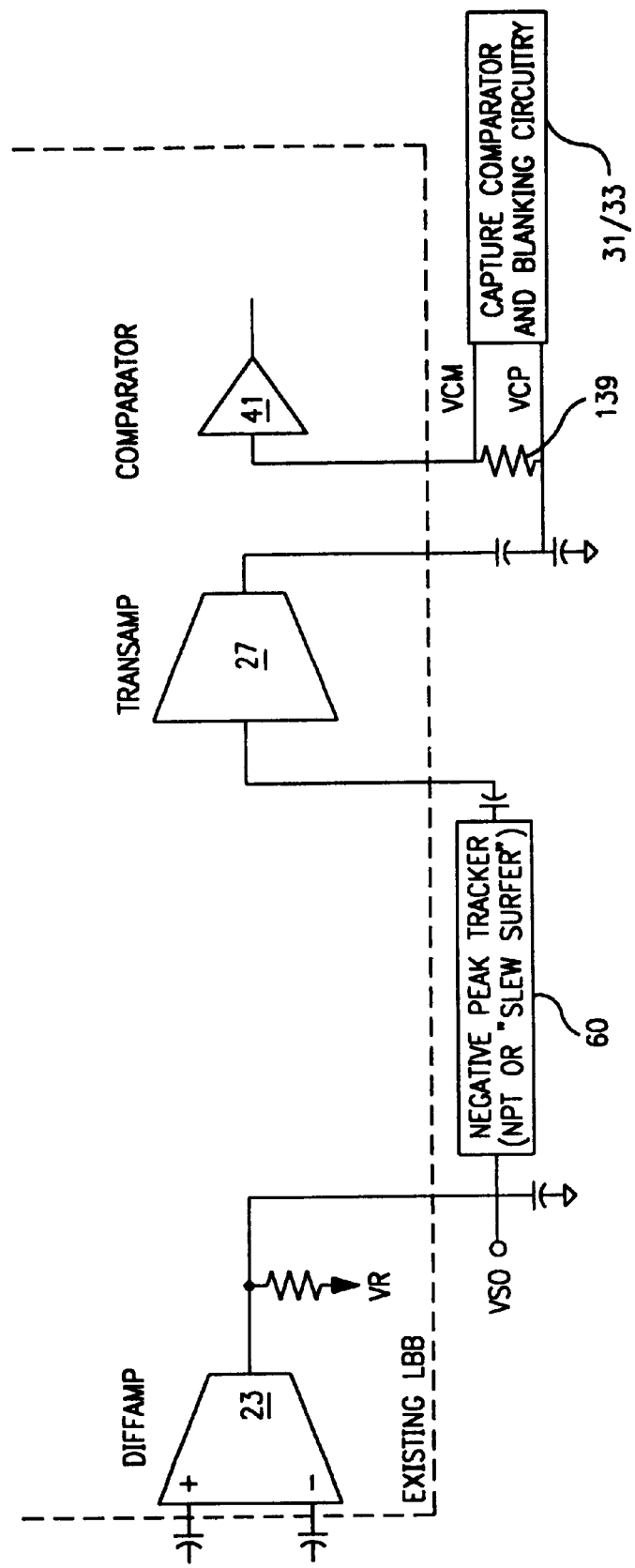
FIG. 21 shows a block diagram of another embodiment of the capture detection circuit of the present invention.

FIG. 21 depicts block diagrams for circuitry of the present invention inserted into the sense amplifier signal path of conventional THERA-brand pacemaker circuitry disposed on a prototype breadboard. CDC 60 is shown as being located between the low pass output of the sense amplifier differential output (i.e., VSO) and the high pass input to band-pass filter 27. The off-chip hybrid capacitors at the input and output of CDC 60 already exist on THERA brand IPGs. Thus, appropriate nodes for the circuit of the present invention were readily accessible. CDC 60 subtracts any residual polarization that is recovered by DIFFAMP 23 and prevents it from exciting band-pass filter 27. Only when there is a sufficient deflection in output of DIFFAMP 23 due to the occurrence of an evoked potential signal will band-pass filter 27 be excited and the signal passed along to the sense amplifier comparator 41 and threshold comparators 31/33 for level detection.

FIG. 21 further shows capture comparator and blanking circuit 31/33 attached across 70 kΩ resistor 139, which is disposed in-line with the input to sense amplifier comparator 41. The voltage generated across resistor 139 is proportional to the current signal present at the input to sense amplifier comparator 41. This differential voltage is measured between VCP and VCM and is referred to hereinafter as VSI. VSI is compared to a threshold level during a period of time after a pacing stimulus or pulse is delivered. If the amplitude of VSI is of sufficient magnitude to trip comparator 31/33 during a predetermined window of time or CDW following delivery of the pacing pulse, then capture is deemed to have occurred. An external comparator most preferably generates logical capture signals when blanking of internal comparator 31/33 is masked during the CDW.

Figure 22:
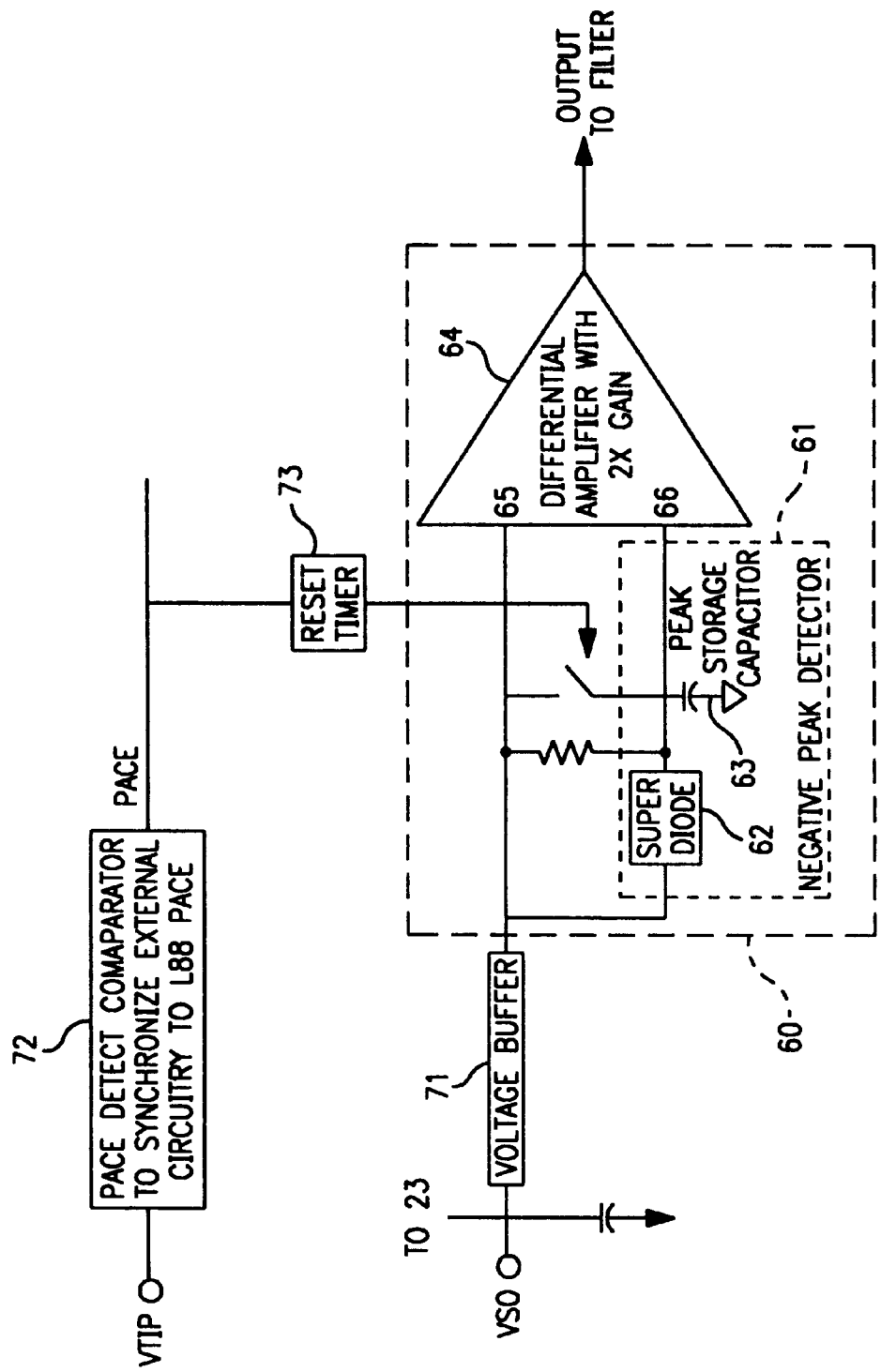
FIG. 22 shows a more detailed block diagram of the circuit shown in FIG. 21.

FIG. 22 shows a more detailed block diagram of the circuit of FIG. 21. The circuit of FIG. 22 is connected to VTIP and synchronizes the operation of CDC 60 and blanking circuitry with the timing of pacing pulse delivery. CDC 60 includes negative peak tracking detector circuit 61 (NPT 61). Voltage buffer 71 isolates CDC 60 from the output of DIFFAMP 23. The output signal provided by voltage buffer 71 is routed into CDC 60 and input 65 of differential amplifier 64. The output of negative peak tracking detector circuit 61 is routed to input 66 of differential amplifier 64. The two inputs to differential amplifier 64 cause amplifier 64 to track the signal sensed at VTIP when an initial negative excursion results from post-pace polarization (the excursion sensed at VSO is actually positive). Difference amplifier 64 prevents any portion of the polarization signal sensed at VRIP from propagating into filter circuit 27 and thereby prevents comparators 31/33 or 41 from erroneously detecting the polarization as an evoked response.

If the signal sensed at VTIP begins to assume a positive slope because an evoked response signal is present or because the polarization signal begins to relax, difference amplifier 64 begins passing an output signal to filter circuit 27. Depending on the amount of the change in slope present in the sensed signal, filter circuit 27 either responds to the change or filters the change out completely and provides no output signal. That is, small changes in the amount of the change in slope of the sensed signal are filtered out completely by filter circuit 27, and large changes in the amount of the change in slope of the sensed signal are passed by filter circuit 27 as an evoked response signal.

Most preferably, a user may adjust the sensitivity of either or both amplifier 64 and filter circuit 27 to provide optimum capture detection in a given patient or implantable medical device. The magnitude of the signal passed by filter circuit 27 and its timing relative to the pacing stimulus are criteria generally employed to determine whether or not the capture has occurred.

As shown in FIG. 22, the output signal provided by pace pulse synchronization circuit block 72 is referred to as PACE and triggers the operation of several different circuits. The PACE signal triggers a reset signal provided by the output of reset timer circuit block 73. The reset signal in turn resets the last negative peak voltage stored by peak detector storage capacitor 63 to a starting potential equivalent to the bias voltage determined by VSO. Most preferably, the bias voltage provided at VSO is −600 mV when the input to sense amplifier 23 is blanked during the period of time when a pacing pulse is being delivered. Block 72 may alternatively be implemented in an integrated circuit.

CDC 60 and NPT 61 were observed to operate optimally when the reset signal provided by reset timer 73 extended into the beginning of the clearing period that typically follows recharge of the pacing pulse output capacitors. CDC 60 is capable of resetting itself to individually negative peak track the post-pace signal sensed after each pacing pulse is delivered. Thus CPC 60 and NPT 61 adapt and respond accurately and quickly to variations in lead type, patient condition and pacing stimulus energies.

Figure 23A:
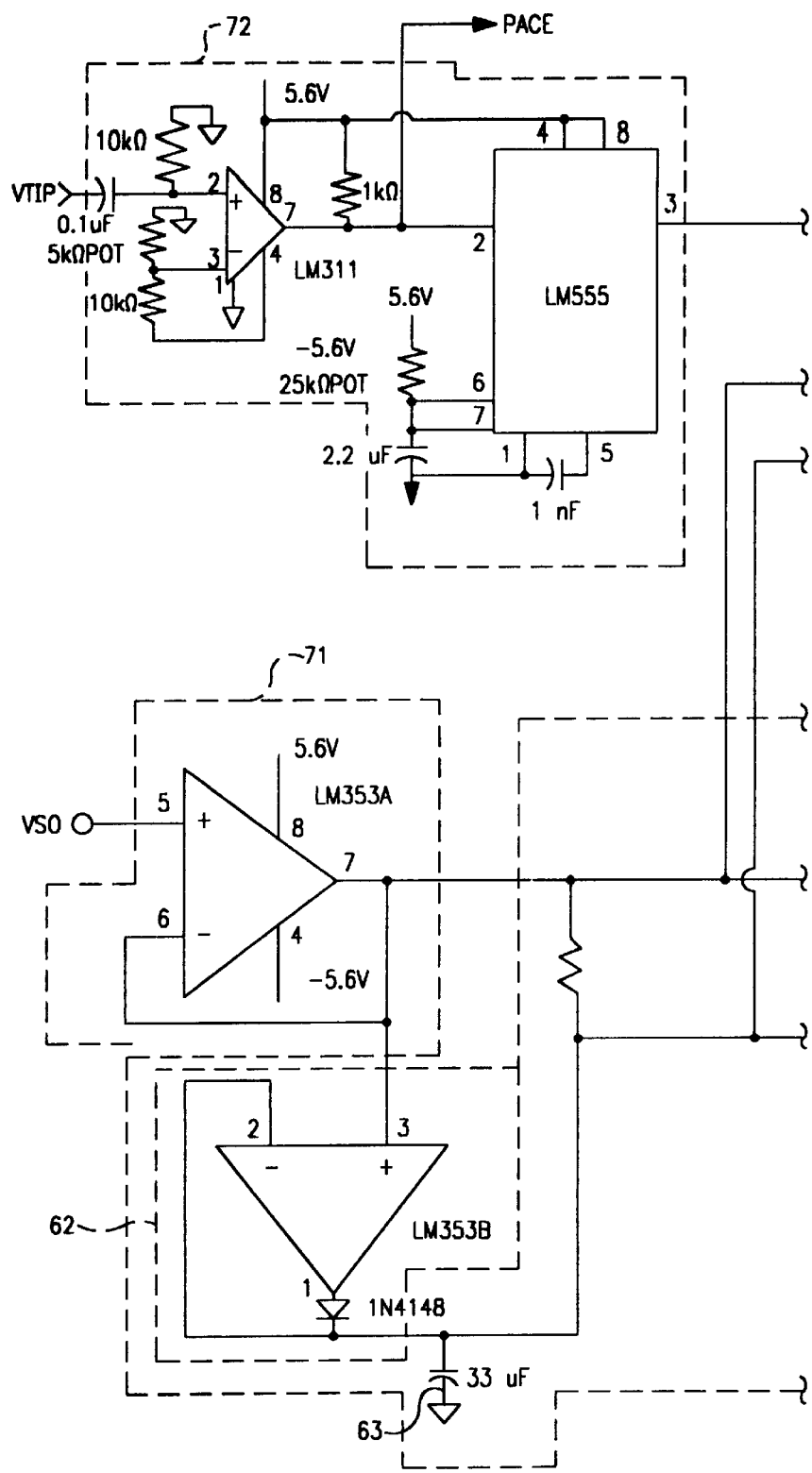
FIG. 23 shows further details of the various circuitry blocks shown in FIG. 22.
Figure 23B:
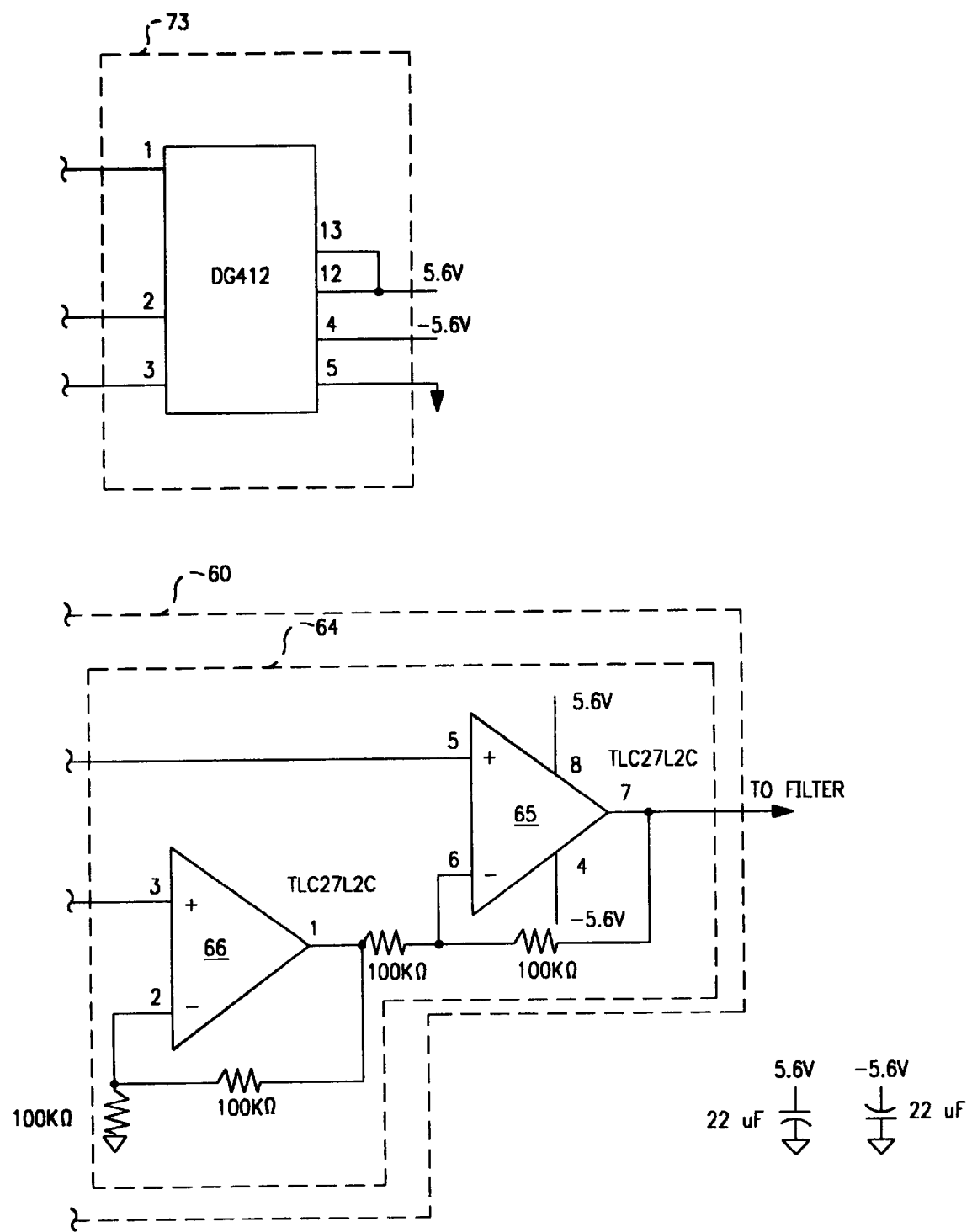

FIG. 23 shows more details of the circuitry shown in FIG. 22. Integrated circuit timers LM311 and LM555 in circuit block 72 generate synchronization and reset signals. Switch DG412 in reset timer circuit block 73 resets NPT 61 prior to the delivery of each pacing stimulus. IC LM353A in circuit block 71 forms the voltage buffer. Difference amplifier 64 comprises Two TLC27L2C ICs. Super diode 62 comprises a 1N4148 diode and IC LM353B. The output provided by super diode 62 is stored by peak storage capacitor 63 for subtraction from the VSO signal.

Figure 24:
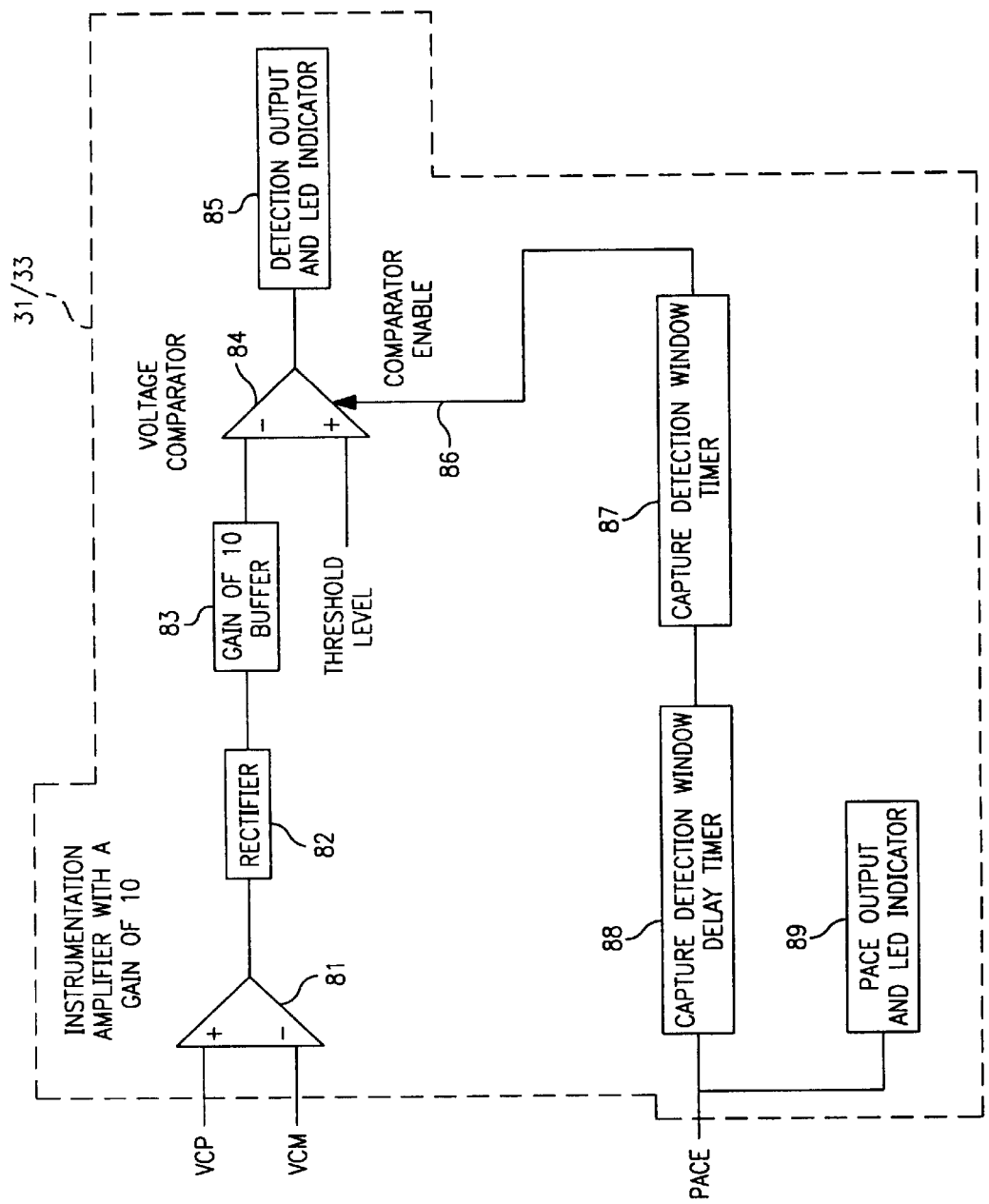
FIG. 24 shows circuit block 31/33 of FIG. 23 in further detail.

FIG. 24 shows circuit block 31/33 in more detail, and the external circuitry employed for generating a CDW and detecting when the capture threshold had been exceeded. The voltage generated across resistor 139 is recovered and amplified by instrumentation amplifier circuit 81 having a gain of ten. Rectifier circuit 82 then rectifies the signal output by amplifier circuit 81. Gain buffer circuit 83 has a gain of ten and amplifies the signal output by rectifier circuit 82. The rectified and twice-amplified signal is then routed into voltage comparator circuit 84 having an adjustable trip point.

The output signal provided by comparator circuit 84 is elongated in respect of the input signal provided to comparator circuit 84 by CDW timer circuit 87. The elongated signal provided by the output of comparator circuit 84 drives an LED in circuit block 85 to thereby provide a visual indication of capture. The CDW is generated by a cascade of timer circuits 88 and 87 whose final output-on line 86 controls the enable of threshold comparator circuit 84. Timer circuit 88 delays the start of the CDW for a predetermined period of time following delivery of a pacing pulse. Timer circuit 87 determines the duration of the CDW. The PACE signal input to timer circuit 88 and pace output and LED indicator circuit 89 originates in synchronization circuitry for triggering timer circuits 88 and 87. Like the output signal provided by comparator circuit 84, the PACE signal provided by the output of circuit block 89 is elongated and drives an LED to provide a visual indication of pacing pulse delivery.

Figure 25A:
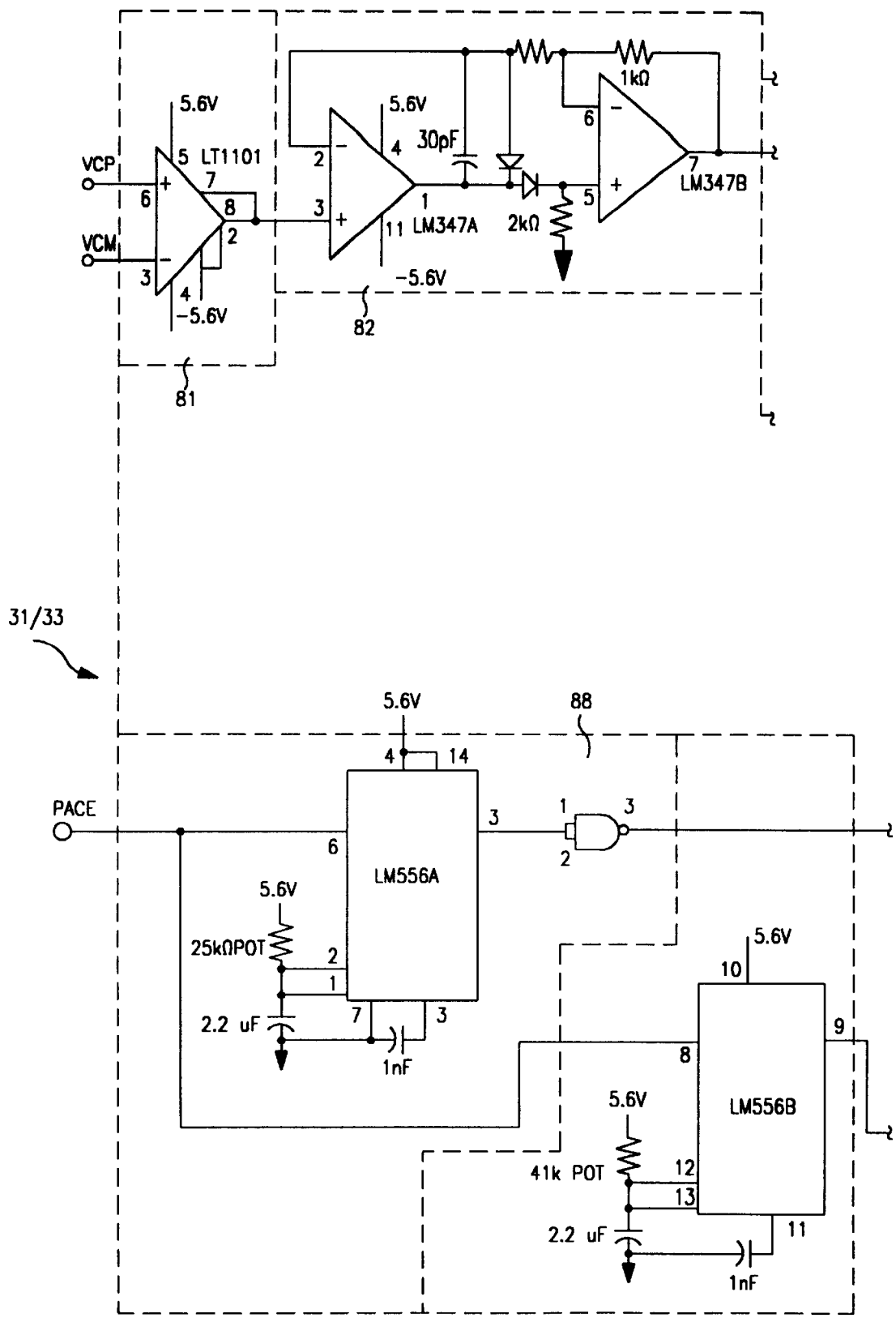
FIG. 25 shows a circuit for implementing blanking and comparator circuit 33 of FIG. 24.
Figure 25B:
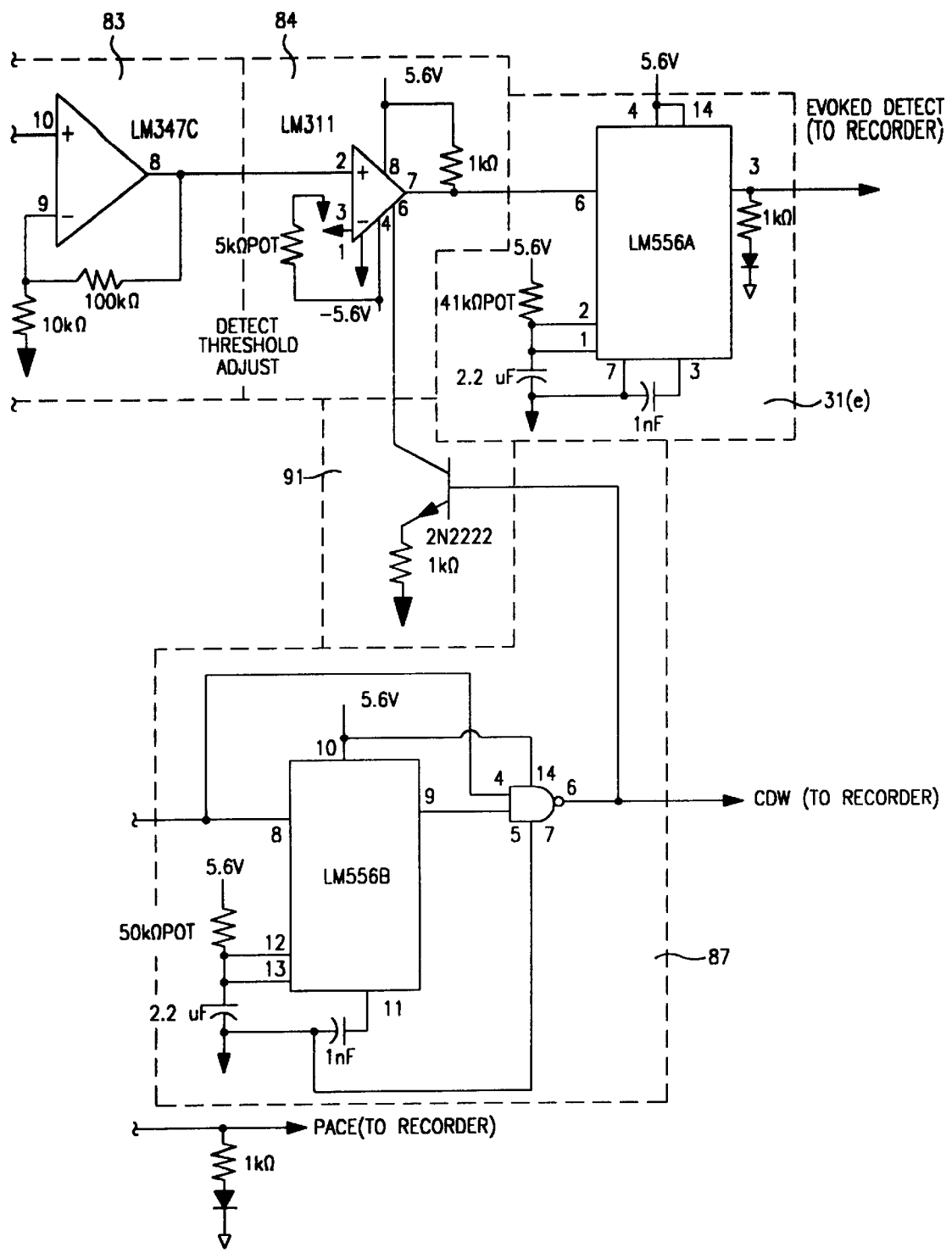

FIG. 25 shows the circuit employed to implement blanking and comparator circuit 31/33 of FIG. 24. In FIG. 25, instrumentation amplifier circuit 81 comprises an LT1101 IC. Cascaded LM347A and LM347B ICs and their associated diodes and resistors form rectifier circuit 82. Circuit block 83 comprises op-amp LM347C and its associated resistors for providing an approximate gain-of-ten buffer for the input to threshold comparator circuit 84 comprising an LM311 IC. The threshold of comparator circuit 84 may be adjusted using the 5 kΩ potentiometer. The duration of the output signal provided by comparator circuit 84 is controlled using one half of the LM556 timer IC in circuit block 87. The PACE signal provided by circuit block 89 is elongated in respect of the PACE signal input thereto by one half of an LM556 IC in circuit block 89. The PACE signal input to circuit block 31/33 also triggers the generation of a CDW by triggering the two halves of LM556 ICs in circuit blocks 88 and 87. The output signal provided by the LM556 timer in circuit block 87 controls the base of 2N2222 transistor 91 having a collector tied to threshold comparator circuit 84. When transistor 91 is turned on comparator circuit 84 is disabled.

The embodiment of the present invention shown in FIGS. 21 through 25 was tested in a canine subject treated in accordance with guidelines and requirements published by the American Association for the Advancement of Laboratory Animal Care. Because the present invention will be used in future medical device products that will be implanted in human subjects, such canine testing for the safety and efficacy of the present invention is required by USFDA rules.

Figure 26:
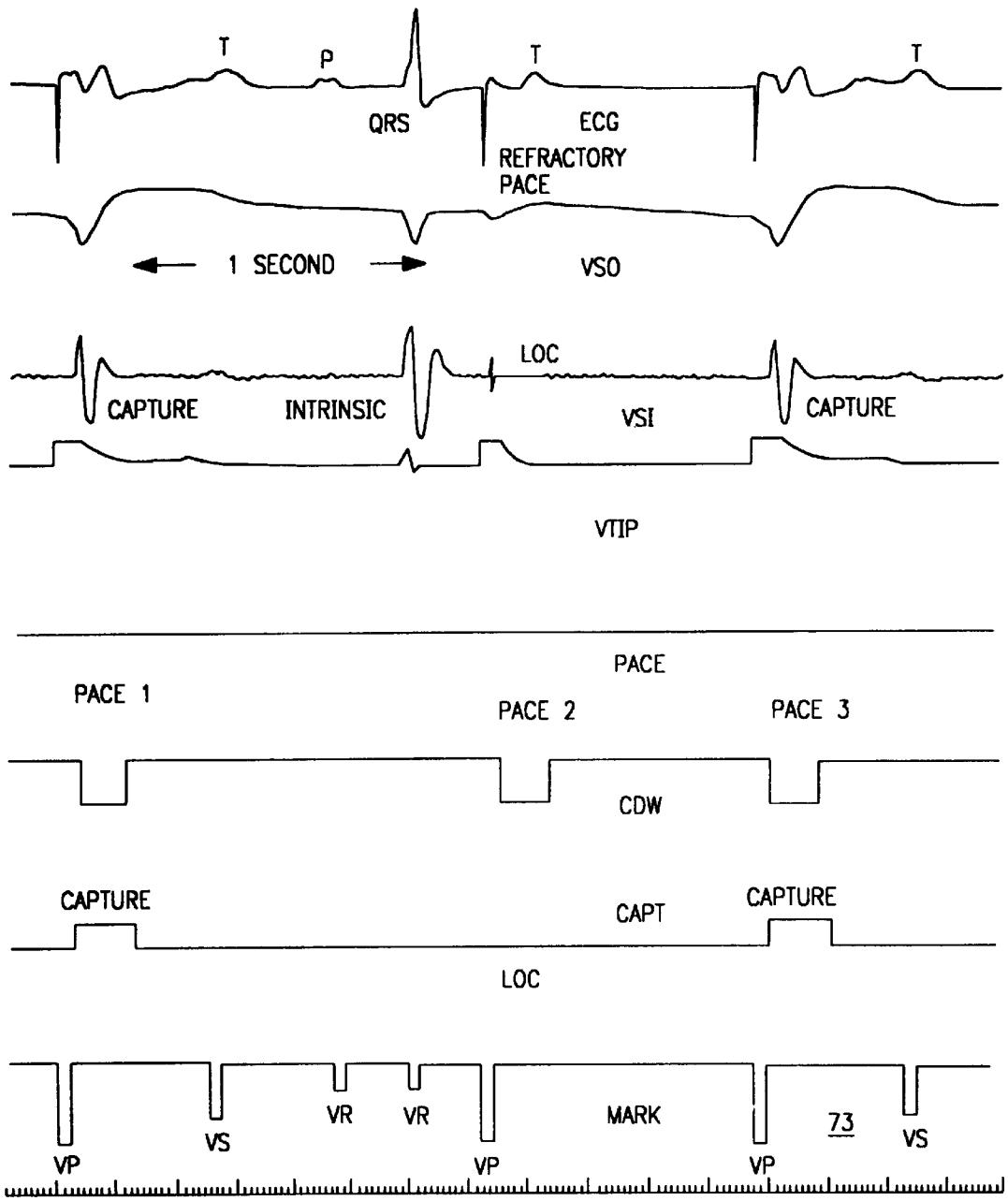
FIG. 26 shows a section of a strip chart recorded using one embodiment of the present invention.

The study was conducted using a MEDTRONIC® ventricular bipolar 5024 CAPSURE® lead, a MEDTRONIC ventricular bipolar 6962 ring-to-tip lead, and a MEDTRONIC THERA-i® IPG modified in accordance with the teachings of the present invention. Pacing was accomplished in both unipolar and bipolar modes. FIG. 26 shows examples of capture, intrinsic and loss of capture events recorded during the study. FIG. 26 shows a section of strip chart recorded during the study where pacing pulses having amplitudes of 3.0 volts durations of 1.5 ms were employed.

The first pacing pulse shown in FIG. 26 captures the myocardium. Note the large deflection caused by the pacing pulse on the VSI channel (which corresponds to the input signal provided to threshold comparator circuit 84). The VSI signal is approximately an order of magnitude larger than the threshold level for sense amplifier 23. The evoked T-wave event corresponding to the first pacing pulse is marked as a ventricular sense event, even though it is barely visible on the VSI channel. The CAPT channel shows that capture was accurately and reliably detected for the first pacing pulse.

The next event shown in FIG. 26 is an intrinsic P-wave event recorded as a refractory sense event. The intrinsic P-wave event is barely visible on the VSI channel. This is followed by an intrinsic QRS complex, which is again recorded as a refractory sense event. The CAPT channel accurately shows no capture event corresponding to the intrinsic event where no pacing pulse was delivered.

The second pacing pulse in FIG. 26 is delivered during an intrinsic refractory period, and therefore does not capture the myocardium. No signal corresponding to the second pacing pulse appears on the VSI channel. The CAPT channel accurately and reliably shows that no capture was detected.

The third pacing pulse captures the myocardium. Once again, the CAPT channel shows that capture was accurately and reliably detected.

FIG. 26 shows that the sensed signal (VTIP) does not change appearance significantly when captured and refractory pace events are compared. Nevertheless, the capture detection circuit of the present invention properly discriminates between captured and refractory events.

Table 1 below lists the channel numbers, recorder data channel settings and input ranges for data recorded on digital audio tape (DAT) in the study, where a TEAC RD-130TE DAT recorder was employed.

TABLE 1

DAT RECORDER SETTINGS

| Channel | Description | Input Range |
|---|---|---|
| 1 | ECG | 2 |
| 2 | VSO | 0.5 |
| 3 | VSI | 0.5 |
| 4 | VTIP | 5 |
| 5 | Pace indicator | 5 |
| 6 | CDW indicator | 5 |
| 7 | Capture indicator | 5 |
| 8 | 9760 marker channel output | 2 |
| 9 | Voice memo | — |

Table 2 below lists the types of events that were recorded on DAT for the study.

TABLE 2

DESCRIPTION OF DAT EVENTS

| Event | Description | Pace (U/B) | Sense (U/B) | Lead |
|---|---|---|---|---|
| 1 | Description, Tape settings, starting at 3.5 V/0.4 ms, 120 bpm, then sweeping to find intermittent capture at 1.0/0.21 | U | U | 5026 |
| 2 | Intermittent capture at 1.0/0.21, 130 bpm | U | U | 5026 |
| 3 | Sweep up to higher amplitudes with 0.4 ms, all the way up to 7.5/0.4 and 7.5/1.5, all at 130 bpm | U | U | 5026 |
| 4 | 0.4 ms, 130 bpm, rapid changes between 0.5 V and 7.5 V | U | U | 5026 |
| 5 | DDI mode, baseline response is so long that it is not a clean refractory period, no useful data was taken | U | U | 5026 |
| 6 | 130 bpm, 3.5 V/0.4 ms | B | B | 5026 |
| 7 | 130 bpm, sweep up with 0.4 ms, up to 7.5/1.5, performance degrades at 7.5/1.0 and above | B | B | 5026 |
| 8 | sweep amplitude at 1.5 ms, falls apart at 4.5 V | B | B | 5026 |
| 9 | sweep of high amplitude at 1.5 ms, falls apart at 4.5 V when bipolar sensing, switch to unipolar, then performance improves so that it works all the way | B | B, switched to U | 5026 |
| 10 | rapid changes from 0.5 V to 7.5 V at 0.4 ms | B | U | 5026 |
| 11 | rapid changes from 0.5 V to 7.5 V at 0.4 ms, 130 bpm | B | B | 5026 |
| 12 | 3.5 V/0.4 ms | U | U | 6962 |
| 13 | sweep of amplitude at 0.4 ms, works well up to 7.5 V, but fails at 7.5 V/ 1.5 ms | U | U | 6962 |
| 14 | 1.5 ms, sweep up in amplitude, begins to fail at 3.0 V | U | U | 6962 |
| 15 | ring to can sensing, at large and small amplitudes | U | ring-can | 6962 |
| 16 | 130 bpm rapid changes at 0.4 ms, 0.5 V to 7.5 V | U | U | 6962 |
| 17 | 130 bpm, 0.4 ms, sweep up in voltage, falls apart at 6.0 V | B | B | 6962 |
| 18 | 130 bpm, 0.4 ms, sweep up in voltage, OK up to 7.5 V, falls apart at 7.5 V/ 1.5 ms | B | U | 6962 |
| 19 | sweep amplitude down @ 1.5 ms, OK up to about 5.0 V | B | B | 6962 |
| 20 | rapid changes at 0.4 ms. 0.5 to 7.5 V | B | B | 6962 |
| 21 | Voice memo at the end of study | | | |
| 22 | Voice memo PGA L88EE05 RHD15 132 TH13 1 nF pulled out, 0.5 Hz front end | | | |

Table 3 below shows the results obtained with the capture detection circuit of the present invention in the study. In Table 3, a detailed count for each setting of each event recorded is shown. The first column in Table 3 lists the event index recorded on DAT tape. The second and third columns in Table 3 list pacing voltages and pulse widths employed for a given event. The fourth column in Table 3 lists the number of pacing pulses delivered for a given setting.

The fifth and six columns in Table 3 list the number of false positive capture events that occurred when a signal of substantial amplitude was observed on the VSI channel but no corresponding depolarization event appeared on the ECG channel. The most common manifestation of this kind of erroneous capture detection occurred when a pacing pulse was delivered during an intrinsic T wave. (As an aside, this could have been corrected by properly programming sensitivity and timing parameters to match canine characteristics.) The next most common type of erroneous capture detection was observed to occur when a subthreshold pacing pulse was delivered and an intrinsic depolarization event occurred within the CDW. Of the foregoing two types of erroneous capture detection, only those false positive capture events were counted where no depolarization occurred.

The seventh column indicates the number of false negative capture events, where a capture event was observed on the ECG channel but no corresponding event appeared on the VSI channel. There were two main causes of this kind of false negative capture event: (1) a pace was delivered near an intrinsic event (or fusion beat), or (2) the pacing energy was so large that detection of the evoked response signal was impossible.

The last column lists success rates for each setting defined as:

$$\text{Success Rate} = \frac{\text{Paces} - (\text{FalsePos}_{NoDepolarization} + \text{FalseNeg})}{\text{Paces}}$$

TABLE 3

CAPTURE DETECTION CIRCUIT PERFORMANCE

| Ev | Pacing Voltage (V) | Pulse Width (ms) | Number of Pacing Pulses Delivered | False Positive Capture Events No depol. | False Positive Capture Events Int. in CDW | False Negative Capture Events | Success Rate |
|---|---|---|---|---|---|---|---|
| 1 | 3.5 | 0.4 | 427 | 0 | 10 | 0 | 1.0 |
|   | 0.5 | 0.4 | 69 | 0 | 36 | 0 | 1.0 |
|   | 3.5 | 0.4 | 33 | 0 | 0 | 0 | 1.0 |
|   | 0.5 | 0.4 | 32 | 0 | 2 | 0 | 1.0 |
|   | 1.0 | 0.4 | 38 | 0 | 0 | 0 | 1.0 |
|   | 1.0 | 0.31 | 43 | 0 | 2 | 0 | 1.0 |
|   | 1.0 | 0.21 | 41 | 0 | 2 | 0 | 1.0 |
|   | 1.0 | 0.24 | 30 | 0 | 4 | 0 | 1.0 |
|   | 1.0 | 0.21 | 177 | 0 | 101 | 0 | 1.0 |
|   | 1.0 | 0.15 | 71 | 0 | 45 | 0 | 1.0 |
|   | 1.0 | 0.21 | 50 | 0 | 20 | 0 | 1.0 |
| 2 | 1.0 | 0.21 | 406 | 0 | 104 | 0 | 1.0 |
| 3 | 1.0 | 0.21 | 26 | 0 | 2 | 0 | 1.0 |
|   | 1.0 | 0.4 | 16 | 0 | 1 | 0 | 1.0 |
|   | 0.5 | 0.4 | 25 | 0 | 4 | 0 | 1.0 |
|   | 1.0 | 0.4 | 57 | 0 | 3 | 0 | 1.0 |
|   | 1.5 | 0.4 | 35 | 0 | 2 | 0 | 1.0 |
|   | 2.0 | 0.4 | 48 | 0 | 1 | 0 | 1.0 |
|   | 3.0 | 0.4 | 65 | 0 | 2 | 0 | 1.0 |
|   | 4.0 | 0.4 | 54 | 0 | 0 | 0 | 1.0 |
|   | 5.0 | 0.4 | 32 | 0 | 0 | 0 | 1.0 |
|   | 6.0 | 0.4 | 44 | 0 | 1 | 0 | 1.0 |
|   | 7.5 | 0.4 | 39 | 0 | 1 | 0 | 1.0 |
|   | 7.5 | 1.5 | 68 | 0 | 0 | 2 | 0.971 |
|   | 3.5 | 1.5 | 66 | 0 | 2 | 0 | 1.0 |
|   | 3.5 | 0.4 | 66 | 0 | 4 | 0 | 1.0 |
| 4 | 3.5 | 0.4 | 132 | 0 | 8 | 0 | 1.0 |
|   | 0.5 | 0.4 | 10 | 0 | 2 | 0 | 1.0 |
|   | 7.5 | 0.4 | 10 | 0 | 0 | 0 | 1.0 |
|   | 0.5 | 0.4 | 11 | 0 | 2 | 0 | 1.0 |
|   | 7.5 | 0.4 | 10 | 0 | 0 | 0 | 1.0 |
|   | 0.5 | 0.4 | 21 | 0 | 6 | 0 | 1.0 |
|   | 7.5 | 0.4 | 13 | 0 | 0 | 0 | 1.0 |
|   | 0.5 | 0.4 | 33 | 0 | 20 | 2 | 0.939 |
| 5 |  |  | no useful data taken |  |  |  |  |
| 6 | 3.5 | 0.4 | 279 | 0 | 0 | 2 | 0.993 |
| 7 | 3.5 | 0.4 | 54 | 0 | 0 | 0 | 1.0 |
|   | 0.5 | 0.4 | 72 | 0 | 29 | 0 | 1.0 |
|   | 1.0 | 0.4 | 114 | 0 | 4 | 0 | 1.0 |
|   | 1.5 | 0.4 | 32 | 0 | 1 | 0 | 1.0 |
|   | 2.0 | 0.4 | 54 | 0 | 5 | 0 | 1.0 |
|   | 3.0 | 0.4 | 41 | 0 | 0 | 0 | 1.0 |
|   | 4.0 | 0.4 | 27 | 0 | 0 | 0 | 1.0 |
|   | 5.0 | 0.4 | 38 | 0 | 0 | 0 | 1.0 |
|   | 7.5 | 0.4 | 37 | 0 | 0 | 0 | 1.0 |
|   | 7.5 | 1.5 | 41 | 0 | 0 | 41 | 0.000 |
|   | 7.5 | 0.4 | 48 | 0 | 0 | 0 | 1.0 |
|   | 7.5 | 1.0 | 50 | 0 | 0 | 50 | 0.000 |
| 8 | 7.5 | 1.0 | 23 | 0 | 0 | 23 | 0.000 |
|   | 3.5 | 1.0 | 22 | 0 | 0 | 0 | 1.0 |
|   | 3.5 | 1.5 | 35 | 0 | 0 | 0 | 1.0 |
|   | 4.0 | 1.5 | 17 | 0 | 0 | 0 | 1.0 |
|   | 5.0 | 1.5 | 51 | 0 | 0 | 51 | 0.000 |
|   | 4.5 | 1.5 | 28 | 0 | 0 | 8 | 0.714 |
|   | 5.0 | 1.5 | 33 | 0 | 0 | 33 | 0.000 |
| 9 | 4.0 | 1.5 | 142 | 0 | 0 | 0 | 1.0 |
|   | 4.5 | 1.5 | 83 | 0 | 0 | 32 | 0.614 |
|   | 5.0 | 1.5 | 149 | 0 | 0 | 110 | 0.262 |
|   | 5.0 | 1.5 | 343 | 0 | 0 | 0 | 1.0 |
|   | 7.5 | 1.5 | 262 | 0 | 0 | 0 | 1.0 |
| 10 | 7.5 | 1.5 | 34 | 0 | 0 | 0 | 1.0 |
|   | 7.5 | 0.4 | 54 | 0 | 0 | 0 | 1.0 |
|   | 0.5 | 0.4 | 18 | 0 | 3 | 0 | 1.0 |
|   | 7.5 | 0.4 | 33 | 0 | 0 | 0 | 1.0 |
|   | 0.5 | 0.4 | 14 | 0 | 1 | 0 | 1.0 |
|   | 7.5 | 0.4 | 9 | 0 | 0 | 0 | 1.0 |
|   | 0.5 | 0.4 | 19 | 0 | 0 | 0 | 1.0 |
|   | 7.5 | 0.4 | 43 | 0 | 0 | 0 | 1.0 |
| 11 | 7.5 | 1.5 | 77 | 0 | 0 | 0 | 1.0 |
|   | 0.5 | 1.5 | 10 | 0 | 1 | 0 | 1.0 |
|   | 7.5 | 1.5 | 10 | 0 | 0 | 0 | 1.0 |
|   | 0.5 | 1.5 | 23 | 0 | 1 | 0 | 1.0 |
|   | 7.5 | 1.5 | 12 | 0 | 0 | 0 | 1.0 |
|   | 0.5 | 1.5 | 11 | 0 | 4 | 0 | 1.0 |
|   | 7.5 | 1.5 | 19 | 0 | 0 | 0 | 1.0 |
|   | 3.5 | 0.4 | 21 | 0 | 0 | 0 | 1.0 |
|   | Total for 5026 | | 4780 | 0 | 436 | 354 | 0.9259 |
|   | Total for 5026, all paces @ 0.4 ms and <6.0 V and 1.5 ms and <4.0 V | | 3201 | 0 | 435 | 4 | 0.9988 |
| 12 | 3.5 | 0.4 | 106 | 0 | 5 | 0 | 1.0 |
| 13 | 3.5 | 0.4 | 18 | 0 | 0 | 0 | 1.0 |
|   | 0.5 | 0.4 | 30 | 0 | 7 | 0 | 1.0 |
|   | 1.0 | 0.4 | 14 | 0 | 0 | 0 | 1.0 |
|   | 1.5 | 0.4 | 30 | 0 | 2 | 0 | 1.0 |
|   | 2.0 | 0.4 | 14 | 0 | 0 | 0 | 1.0 |
|   | 3.0 | 0.4 | 82 | 0 | 4 | 0 | 1.0 |
|   | 4.0 | 0.4 | 21 | 0 | 1 | 0 | 1.0 |
|   | 5.0 | 0.4 | 128 | 0 | 0 | 0 | 1.0 |
|   | 6.0 | 0.4 | 18 | 0 | 0 | 0 | 1.0 |
|   | 7.5 | 0.4 | 35 | 0 | 0 | 0 | 1.0 |
|   | 7.5 | 1.5 | 17 | 0 | 0 | 17 | 0.000 |
|   | 0.5 | 1.5 | 2 | 0 | 0 | 0 | 1.0 |
| 14 | 0.5 | 1.5 | 39 | 0 | 6 | 0 | 1.0 |
|   | 1.0 | 1.5 | 15 | 0 | 2 | 0 | 1.0 |
|   | 1.5 | 1.5 | 14 | 0 | 0 | 0 | 1.0 |
|   | 2.0 | 1.5 | 16 | 0 | 0 | 0 | 1.0 |
|   | 3.0 | 1.5 | 23 | 0 | 0 | 0 | 1.0 |
|   | 4.0 | 1.5 | 55 | 0 | 0 | 0 | 1.0 |
|   | 3.0 | 1.5 | 117 | 0 | 0 | 0 | 1.0 |
|   | 4.0 | 1.5 | 145 | 0 | 0 | 0 | 1.0 |
|   | 5.0 | 1.5 | 25 | 0 | 0 | 25 | 0.000 |
|   | 6.0 | 1.5 | 41 | 0 | 0 | 41 | 0.000 |
| 15 | 6.0 | 1.5 | 45 | 3 | 0 | 1 | 0.911 |
|   | 0.5 | 1.5 | 22 | 0 | 0 | 0 | 1.0 |
|   | 7.5 | 1.5 | 49 | 6 | 0 | 0 | 0.878 |
|   | 0.5 | 1.5 | 29 | 0 | 0 | 0 | 1.0 |
|   | 1.0 | 0.4 | 25 | 0 | 1 | 1 | 0.960 |
|   | 1.5 | 0.4 | 45 | 0 | 0 | 0 | 1.0 |
| 16 | 0.5 | 0.4 | 15 | 0 | 0 | 0 | 1.0 |
|   | 7.5 | 0.4 | 6 | 0 | 0 | 0 | 1.0 |

TABLE 3-continued

CAPTURE DETECTION CIRCUIT PERFORMANCE

| Ev | Pacing Voltage (V) | Pulse Width (ms) | Number of Pacing Pulses Delivered | False Positive Capture Events | | False Negative Capture Events | Success Rate |
|---|---|---|---|---|---|---|---|
| | | | | No depol. | Int. in CDW | | |
| | 0.5 | 0.4 | 7 | 0 | 4 | 0 | 1.0 |
| | 7.5 | 0.4 | 9 | 0 | 0 | 0 | 1.0 |
| | 0.5 | 0.4 | 9 | 0 | 0 | 0 | 1.0 |
| | 7.5 | 0.4 | 9 | 0 | 0 | 0 | 1.0 |
| | 0.5 | 0.4 | 9 | 0 | 2 | 1 | 0.889 |
| | 7.5 | 0.4 | 7 | 0 | 0 | 0 | 1.0 |
| | 0.5 | 0.4 | 13 | 0 | 0 | 1 | 0.923 |
| 17 | 0.5 | 0.4 | 27 | 0 | 0 | 0 | 1.0 |
| | 1.0 | 0.4 | 11 | 0 | 0 | 0 | 1.0 |
| | 1.5 | 0.4 | 44 | 0 | 0 | 0 | 1.0 |
| | 2.0 | 0.4 | 32 | 0 | 0 | 0 | 1.0 |
| | 3.0 | 0.4 | 35 | 0 | 0 | 0 | 1.0 |
| | 4.0 | 0.4 | 79 | 0 | 0 | 0 | 1.0 |
| | 5.0 | 0.4 | 62 | 0 | 0 | 0 | 1.0 |
| | 6.0 | 0.4 | 64 | 0 | 0 | 64 | 0.000 |
| 18 | 0.5 | 0.4 | 13 | 0 | 1 | 0 | 1.0 |
| | 1.0 | 0.4 | 19 | 0 | 4 | 0 | 1.0 |
| | 1.4 | 0.4 | 85 | 0 | 0 | 0 | 1.0 |
| | 2.0 | 0.4 | 16 | 0 | 0 | 0 | 1.0 |
| | 3.0 | 0.4 | 35 | 0 | 0 | 0 | 1.0 |
| | 4.0 | 0.4 | 18 | 0 | 0 | 0 | 1.0 |
| | 5.0 | 0.4 | 16 | 0 | 0 | 0 | 1.0 |
| | 6.0 | 0.4 | 48 | 0 | 0 | 1 | 0.979 |
| | 7.5 | 0.4 | 92 | 0 | 0 | 0 | 1.0 |
| | 7.5 | 1.5 | 23 | 0 | 0 | 0 | 0.000 |
| 19 | 7.5 | 1.5 | 16 | 0 | 0 | 16 | 0.000 |
| | 6.0 | 1.5 | 15 | 0 | 0 | 15 | 0.000 |
| | 5.0 | 1.5 | 9 | 0 | 0 | 3 | 0.667 |
| | 4.0 | 1.5 | 12 | 0 | 0 | 1 | 0.917 |
| | 5.0 | 1.5 | 70 | 0 | 4 | 2 | 0.971 |
| | 5.5 | 1.5 | 43 | 3 | 1 | 39 | 0.023 |
| | 5.0 | 1.5 | 13 | 0 | 0 | 0 | 1.0 |
| | 4.0 | 1.5 | 10 | 0 | 0 | 0 | 1.0 |
| | 3.0 | 1.5 | 73 | 0 | 0 | 0 | 1.0 |
| | 2.0 | 1.5 | 31 | 0 | 0 | 0 | 1.0 |
| | 1.5 | 1.5 | 11 | 0 | 0 | 0 | 1.0 |
| | 1.0 | 1.5 | 70 | 0 | 0 | 1 | 0.986 |
| | 0.5 | 1.5 | 26 | 0 | 0 | 0 | 1.0 |
| 20 | 0.5 | 0.4 | 10 | 0 | 3 | 0 | 1.0 |
| | 7.5 | 0.4 | 6 | 0 | 0 | 0 | 1.0 |
| | 0.5 | 0.4 | 10 | 0 | 0 | 0 | 1.0 |
| | 7.5 | 0.4 | 7 | 0 | 0 | 1 | 0.857 |
| | 0.5 | 0.4 | 11 | 0 | 1 | 1 | 0.909 |
| | 7.5 | 0.4 | 7 | 0 | 0 | 2 | 0.714 |
| | 0.5 | 0.4 | 16 | 0 | 1 | 1 | 0.938 |
| | Total for 6962 | | 2489 | 12 | 49 | 234 | 0.9012 |
| | Total for 6962, all paces @ 0.4 ms and <6.0 V and 1.5 ms and <4.0 V | | 1833 | 0 | 44 | 7 | 0.9962 |

Table 3 above shows that the embodiment of the capture detection circuit of the present invention shown in FIGS. 21–26 hereof detected capture accurately and consistently when pacing pulse voltage settings were less than or equal to 6.0 volts for pacing pulse widths of 0.4 ms, or pacing pulse voltage settings were less than or equal to 4.0 volts for pacing pulse widths of 1.5 ms pulse widths when 5026 CapSure leads were employed in either unipolar or bipolar sensing configurations. The foregoing data were acquired over the lo delivery of more than 3200 pacing pulses having numerous voltage and pulse width settings.

Table 3 also shows that the embodiment of the capture detection circuit of the present invention shown in FIGS. 21–26 hereof detected capture accurately and consistently when pacing pulse voltage settings were less than or equal to 5.0 volts for pacing pulse widths of 0.4 ms, or pacing pulse voltage settings were less than or equal to 4.0 volts for pacing pulse widths of 1.5 ms pulse when a 6962 ring tip lead was employed in either unipolar or bipolar sensing configurations. The foregoing data were acquired over the delivery of more than 1800 pacing pulses having numerous voltage and pulse width settings.

Table 3 shows further that capture detection accuracy was enhanced when tip-to-can (i.e. unipolar) sensing configurations were employed instead of tip-to-ring (i.e. bipolar) sensing configurations were employed, regardless of pacing pulse polarity.

From the foregoing detailed description of specific embodiments of the invention, it should be apparent that a novel and efficacious sensing circuit for a cardiac stimulating device has been disclosed. The sensing circuit is capable of detecting strong and weak evoked responses to cardiac stimulating pulses. In one embodiment of the present invention, a first-order peak tracking circuit detects changes in the polarity of the slope of a cardiac sensed signal. A feedback circuit filters post-pacing pulse electrode-tissue-polarization artifacts from the sensed signal.

In another embodiment of the invention, a second-order peak tracking circuit is also employed to detect increases in or acceleration of the slope of the sensed signal. A feedback loop in the second-order peak tracking circuit adds current to the sensed signal in response to such detected acceleration.

Figure 27:
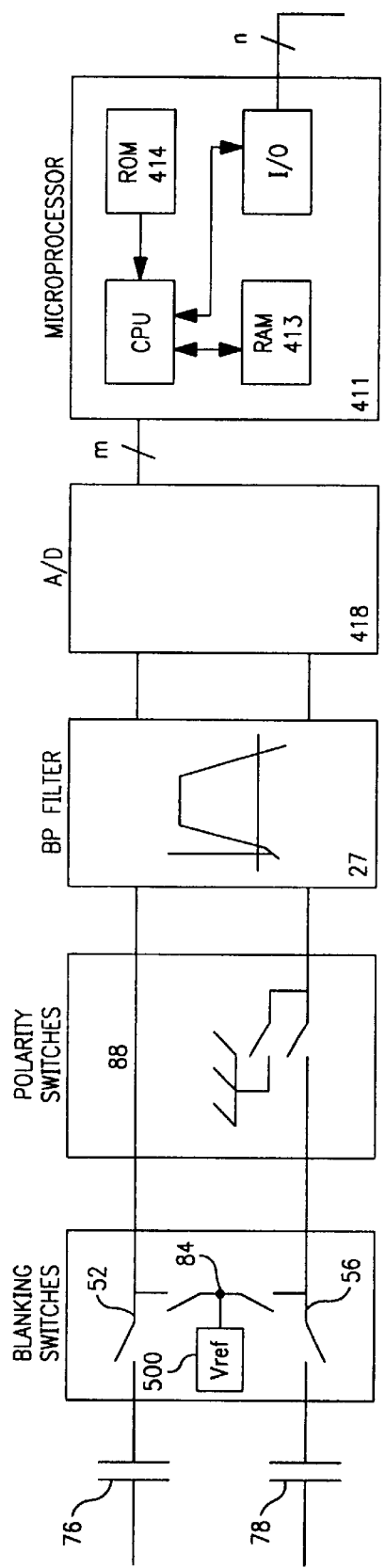
FIG. 27 shows a block diagram of one embodiment of a microprocessor capture detection circuit of the present invention.
Figure 28A:
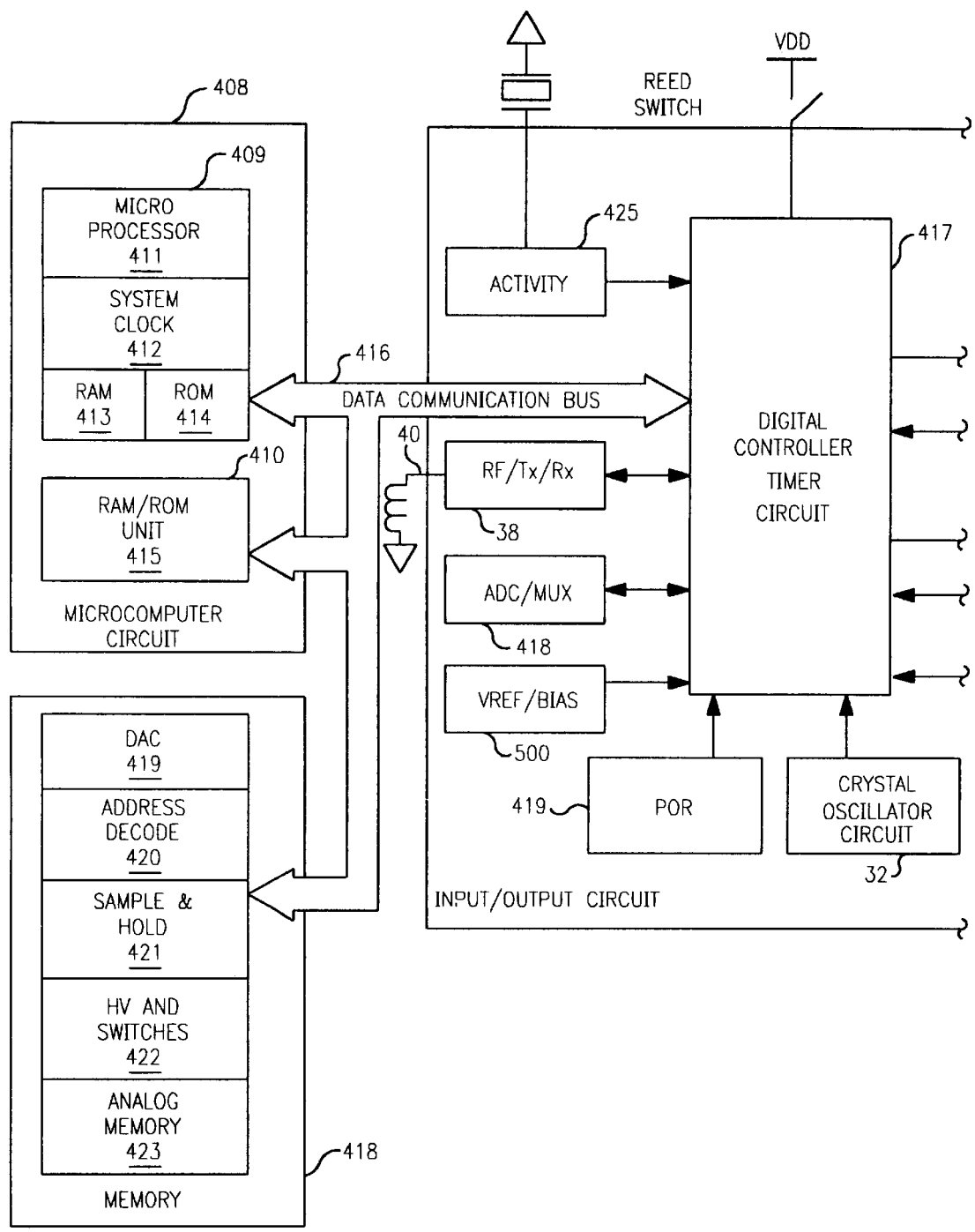
FIG. 28 shows a block diagram of another embodiment of a microprocessor capture detection circuit of the present invention.
Figure 28B:
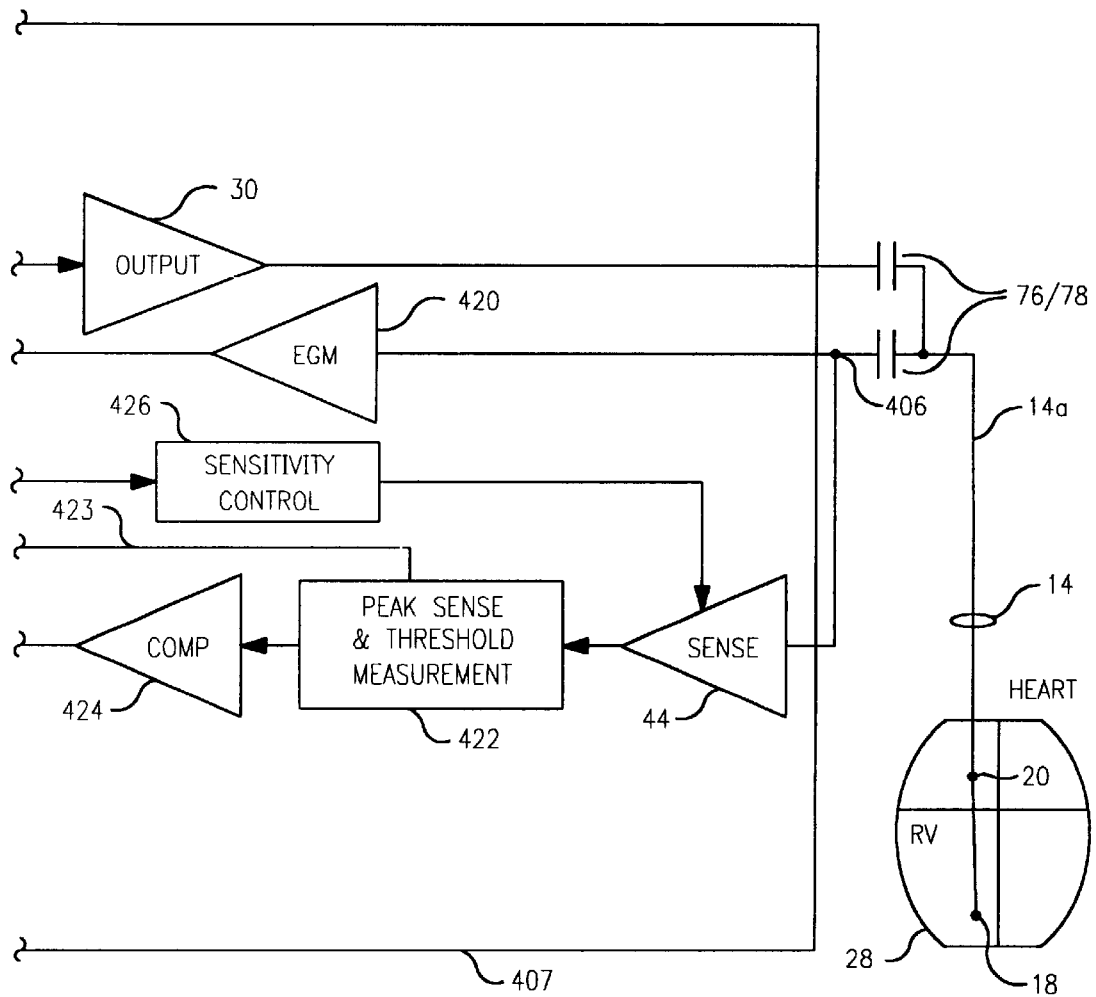

FIGS. 27 and 28 show software programmable device embodiments of the present invention, where each such embodiment has two preferred features: (1) a microprocessor, and (2) electronic interface circuitry.

FIG. 27 shows a block diagram of a microprocessor embodiment of the capture detection circuit of the present invention. Blanking switches 52 and 56 and polarity switches 88 are similar to those disclosed above in other embodiments of the present invention. Bandpass filter 27 provides anti-aliasing protection for signals input to analog-to-digital (A/D) converter 418. A/D converter 418 outputs m-bit wide words to be stored for subsequent processing. Suitable A/D converter architectures require sampling frequencies exceeding about 1 kHz, and include flash, delta-sigma, or successive approximation types of A/ND converters. Microprocessor 411 stores an incoming waveform into an array in RAM 413, performs negative peak tracking and/or second order peak tracking operations on the stored array, and provides an indication of capture or non-capture to readable I/O.

Following a test pace, a waveform of suitable length is sampled and stored in RAM 413 of microprocessor 411. A preferred time window over which to acquire the waveform has been found to be about 110 milliseconds after blanking switches 52/56 close following delivery of a stimulation pulse. In a fashion broadly similar to the techniques utilized in non-microprocessor embodiments of the present invention described hereinabove, microprocessor 411 peak tracks stored waveform arrays, and subtracts from them the post-pace polarization signal to yield an estimated evoked response signal. For second order peak tracking, microprocessor 411 may develop an estimate of the rate of change of the voltage of the input signal (or stored waveform arrays) by searching for waveform array segments where the slew rate shows, for example, a negatively accelerating rate of change in voltage of the input signal.

FIG. 28 shows a block diagram of a microprocessor capture detection circuit of the present invention. Pacemaker 10 is schematically shown in FIG. 28 to be electrically coupled via pacing lead 14 to a patient's heart 28. Lead 14 may include intracardiac electrodes 18 and 20, and a pressure sensor located near its distal end and positioned within the right ventricular (RV) chamber of heart 28. Lead 14 may be configured to have unipolar or bipolar electrodes, as is well known in the art. Lead 14 may also comprise a steroid-tipped, unipolar lead with an integral pressure transducer.

Electrode 18 may be coupled by lead 14 through input capacitor 52/56 to node 406 and to input/output terminals of input/output circuit 407. Input/output circuit 407 contains the analog circuits for interface to the heart 28, an activity sensor, a pressure sensor, and antenna 40, as well as for the application of stimulating pulses to heart 28 to control its rate as a function thereof under control of the software-implemented algorithms in microcomputer circuit 408.

Microcomputer circuit 408 comprises an on-board circuit 409 and an off-board circuit 410. On-board circuit 409 includes microprocessor 411, system clock circuit 412, and on-board RAM 413 and ROM 414. Off-board circuit 410 includes off-board RAM/ROM unit 415. Microcomputer circuit 408 is coupled by data communication bus 416 to digital controller/timer circuit 417. Microcomputer circuit 408 may be fabricated of custom integrated circuit devices augmented by standard RAM/ROM components. Data communication bus 416 may also be coupled to analog memory integrated circuit 418 which includes DAC 419, address decode circuit 420, sample and hold circuit 421, high voltage supply and associated switches 422 and EEPROM memory cells 423.

It will be understood that the electrical components represented in FIG. 28 are powered by an appropriate implantable battery power source 24, not shown, in accordance with common practice in the art.

Antenna 40 is connected to input/output circuit 407 for purposes of uplink/downlink telemetry through RF transmitter/receiver (RF TX/RX) unit 38. Telemetering both analog and digital data between antenna 40 and an external device, such as an external programmer (not shown), may be accomplished by means of all data first being digitally encoded and then pulse-position modulated on a damped RF carrier as described in U.S. Pat. No. 5,354,319 entitled "Telemetry System for an Implantable Medical Device" to Wyborny et al. issued Oct. 11, 1994, hereby incorporated by reference herein in its entirety.

Crystal oscillator circuit 32, typically a 32,768-Hz crystal-controlled oscillator, provides main timing clock signals to digital controller/timer circuit 417. Vref/Bias circuit 500 generates a stable voltage reference and bias currents for the analog circuits of input/output circuit 407. Analog-to-digital converter/multiplexer (ADC/MUX) unit 418 digitizes analog signals and voltages to provide "real-time" telemetry of pressure and intracardiac signals and battery end-of-life (EOL) replacement function. A power-on-reset (POR) circuit 419 functions as a means to reset circuitry and related functions to a default condition upon detection of a low battery condition, which will occur upon initial device power-up or will transiently occur in the presence of electromagnetic interference, for example.

Operating commands for controlling the timing of pacemaker 10 are coupled by bus 416 to digital controller/timer circuit 417 wherein digital timers and counters are employed to establish the overall escape interval of the pacemaker, as well as various refractory, blanking, and other timing windows for controlling the operation of the peripheral components within input/output circuit 407. Digital controller/timer circuit 417 is coupled to sense amplifier 44 and electrogram amplifier 420 for receiving amplified and processed signals picked up from electrodes 18 or 20 through lead conductor 14a and capacitor 76/78 representative of the electrical activity of the patient's heart 28. Sense amplifier 44 amplifies sensed electrical cardiac signals and provides this amplified signal to peak sense and threshold measurement circuitry 422, which provides an indication of peak sensed voltages and the measured sense amplifier threshold voltage on multiple conductor signal path 423 to digital controller/timer circuit 417. The amplified sense amplifier signal is also provided to comparator 424.

The electrogram signal developed by EGM amplifier 420 is used when the implanted device is interrogated by an external programmer, not shown, in order to transmit by uplink telemetry a representation of the analog electrogram of the patient's electrical heart activity as described in U.S. Pat. No. 4,556,063 to Thompson et al., hereby incorporated by reference herein in its entirety. Stimulating pulse output circuit 30 provides the pacing stimulus to the patient's heart 28 through coupling capacitor 76/78 in response to a pacing trigger signal developed by digital controller/timer circuit 417 each time the escape interval times out, or an externally transmitted pacing command has been received, or in response to other stored commands as is well known in the pacing art.

Digital controller/timer circuit 417 may also be coupled to an activity circuit 425 for receiving, processing, and amplifying signals received from an intracardiac or other activity sensor. Activity circuit 425 produces an activity signal which is representative of the patient's metabolic requirements. Similarly, digital controller/timer circuit 417 may be coupled to a pressure circuit for receiving, amplifying and processing sensor output from an intracardiac or other pressure sensor. A pressure circuit produces an amplified, filtered analog pressure signal which is received by digital controller/timer circuit 417. In conjunction with ADC/MUX 418, digital controller/timer circuit 417 may sample and digitize a pressure signal generated by a pressure circuit to obtain a digital representation of the peak value of intracardiac pressure during each cardiac cycle. This value could then be provided to microprocessor 409, which maintains a running average over a previous number of cardiac cycles (e.g. sixteen cycles) of the intracardiac pulse pressure.

FIG. 28 further shows input/output circuit 407 including sensitivity control circuitry 426 coupled between digital controller/timer circuit 417 and sense amplifier circuit 44. Sensitivity control circuit 426 controls the gain of sense amplifier 44 and thus the sensing threshold of sense amplifier 44 as instructed by digital controller/timer circuit 417.

In memory 418 in FIG. 28, digital to analog converter (DAC) 419 converts a digital representation of a signal into an analog signal. Address decode 420 controls the addressing of the row and column of analog memory 423 for both writing and reading data. Sample and hold circuit 421 samples an analog signal at a periodic rate to enable the storage of an analog signal in analog memory 423. High voltage (HV) and switch circuit 422 generates approximately 20 volts DC and, via the switches, stores a representation of an analog signal in analog memory 423. Analog memory 423 may be an EE-PROM memory suitable for the present application of storing analog signals.

In FIG. 28, a physiologic electrical signal or intracardiac electrical signal originating in heart 28 is processed by EGM 420. Microprocessor 409 samples the physiologic electrical signal through digital controller/timer circuit 417. The physiologic electrical signal is then stored as an array in RAM 413. The array in RAM 413 is post-processed using an algorithm such as that set forth in Table 5 below. A reference point is established in the array that corresponds to the minimum current value of the entire stored array (as measured from the beginning to the end of the array). The reference point is then continuously updated and decreased in value provided that an estimate of dV/dt around a local point in the array is assumed to be less than zero or substantially less than zero. When or if the estimate of dV/dt around a local point in the array becomes equal to zero, or substantially equal to zero, that reference point is held to the minimum or "negative peak" value it attained during the period of time when dV/dt of the local point in the array was less negative. When or if the estimate of dV/dt becomes positive or substantially positive thereafter, the difference between the local point and the minimum value obtained and tracked previously is amplified.

Once microprocessor 411 determines that a "negative peak" has been attained, an output signal corresponding or proportional to the difference between the largest amplitude signal measured after the "negative peak" and the "negative peak" value itself is processed for further discrimination and differentiation sensing techniques broadly similar to those described above respecting non-microprocessor embodiments of the present invention. Such further discrimination or differentiation processing may include minimum signal duration filtering, blanking during pace and recharge, masking during extended sensing, and masking for noise conditions.

For example, If a pacing pulse does not capture the myocardium, further discrimination or differentiation processing results in little or no signal being output that is insufficient in amplitude to trip one or a series of threshold level comparators. Conversely, if a pacing pulse does cause the myocardium to contract and capture therefore occurs, further discrimination or differentiation processing results in a relatively large amplitude signal being output that is sufficient in amplitude to trip one or a series of threshold level comparators. By properly selecting a threshold level for such comparators, the microprocessor circuit of the present invention may discriminate between captured and non-captured pacing pulses with a high degree of reliability and accuracy.

Those of ordinary skill will now appreciate that other topologies of the microprocessor embodiment of the capture detection circuit of the present invention not shown in FIGS. 27 and 28 also fall within the scope of the present invention.

Additionally, although only a few exemplary embodiments of the present invention have been described in detail above, those skilled in the art will appreciate readily that many modifications are possible in the exemplary embodiments without materially departing from the novel teachings and advantages of the invention. Accordingly, all such modifications are intended to be included within the scope of the present invention as defined in the following claims.

The scope of the present invention is not limited to pacing, monitoring or sensing applications, but extends to defibrillation, cardiac mapping and other medical and medical device applications and methods. The scope of the present invention is not limited to applications where a human heart is sensed, monitored, paced, or defibrillated, but includes similar applications in other mammalians and mammalian organs.

The preceding specific embodiments are illustrative of the practice of the invention. It is to be understood, therefore, that other expedients known to those skilled in the art or disclosed herein, may be employed without departing from the invention or the scope of the appended claims.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

All patents or printed publications listed in table 1 or elsewhere hereinabove are hereby incorporated by reference herein into the specification hereof, each in its respective entirety.

We claim:

1. A medical device capable of providing intra-cardiac electrical stimulating pulses to a patient's heart and detecting an evoked cardiac response to the stimulating pulses, comprising:

means for delivering electrical stimulating pulses to a patient's heart to evoke a cardiac contraction, each electrical stimulating pulse causing a post-delivery stimulation polarization artifact signal that decays from a starting potential to a quiescent potential over a post-delivery time period;

means for sensing a physiologic cardiac signal spontaneously originating in the patient's heart;

means for sensing a cardiac sensed signal comprising the decaying post-delivery stimulation polarization artifact signal and a physiologic evoked response signal of the heart signifying and accompanying an evoked cardiac contraction being operable during the post-delivery time period; and a programmable microprocessor means for processing the cardiac sensed signal for a predetermined time period following the delivery of the electrical stimulating pulse to detect the evoked response signal within the cardiac sensed signal, if present, by use of a peak tracking detection algorithm that detects a change in polarity of the cardiac sensed signal during its decay.

2. The device of claim 1 wherein the programmable microprocessor means is programmed to second order peak track the evoked response signal within the cardiac sensed signal by detecting an increase in the magnitude of the derivative cardiac sensed signal signifying the evoked response signal.

3. The device of claim 1 wherein the programmable microprocessor means is programmed to generate an estimate of a stimulation polarization artifact signal upon the detected change in polarity.

4. The device of claim 3, further comprising means for sampling the cardiac sensed signal and storing voltage samples as a waveform array, and wherein the programmable microprocessor means is programmed to develop an estimate of the rate of change of the voltage of the cardiac sensed signal by searching for waveform segments in the stored waveform array where the slew rate depicts an accelerating rate of change in voltage of the input signal.

5. The device of claim 3, wherein the programmable microprocessor means is programmed to subtract the estimate of the stimulation polarization artifact signal from the cardiac sensed signal to provide an estimate of an evoked response signal.

* * * * *